(12) United States Patent
Cogswell et al.

(10) Patent No.: US 10,266,596 B1
(45) Date of Patent: *Apr. 23, 2019

(54) CANCER IMMUNOTHERAPY BY DISRUPTING PD-1/PD-L1 SIGNALING

(71) Applicant: Bristol-Myers Squibb Company, Princeton, NJ (US)

(72) Inventors: John P. Cogswell, Yardley, PA (US); Stacie M. Goldberg, Potomac, MD (US); Ashok K. Gupta, Clarksburg, MD (US); Maria Jure-Kunkel, Plainsboro, NJ (US); Xi-Tao Wang, Wellesley, MA (US); Jon M. Wigginton, Collegeville, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/213,965

(22) Filed: Dec. 7, 2018

Related U.S. Application Data

(60) Continuation of application No. 16/006,365, filed on Jun. 12, 2018, which is a continuation of application No. 14/950,748, filed on Nov. 24, 2015, now Pat. No. 10,072,082, which is a division of application No. 13/892,671, filed on May 13, 2013, now Pat. No. 9,212,224.

(60) Provisional application No. 61/647,442, filed on May 15, 2012, provisional application No. 61/790,747, filed on Mar. 15, 2013.

(51) Int. Cl.
| | |
|---|---|
| C07K 16/28 | (2006.01) |
| A61K 39/395 | (2006.01) |
| G01N 33/574 | (2006.01) |
| C07K 16/18 | (2006.01) |
| A61K 39/00 | (2006.01) |

(52) U.S. Cl.
CPC ...... *C07K 16/2818* (2013.01); *A61K 39/3955* (2013.01); *C07K 16/18* (2013.01); *C07K 16/2803* (2013.01); *C07K 16/2827* (2013.01); *G01N 33/57492* (2013.01); *A61K 2039/505* (2013.01); *A61K 2039/507* (2013.01); *C07K 2317/76* (2013.01); *G01N 2333/70596* (2013.01); *G01N 2800/52* (2013.01); *Y02A 50/41* (2018.01); *Y02A 50/412* (2018.01)

(58) Field of Classification Search
None
See application file for complete search history.

(56) References Cited

U.S. PATENT DOCUMENTS

| | | |
|---|---|---|
| 6,803,192 B1 | 10/2004 | Chen |
| 6,808,710 B1 | 10/2004 | Wood et al. |
| 6,984,720 B1 | 1/2006 | Korman et al. |
| 7,595,048 B2 | 9/2009 | Honjo et al. |
| 7,635,757 B2 | 12/2009 | Freeman et al. |
| 7,943,743 B2 | 5/2011 | Korman et al. |
| 8,008,449 B2 | 8/2011 | Korman et al. |
| 8,168,757 B2 | 5/2012 | Finnefrock et al. |
| 8,217,149 B2 | 7/2012 | Irving et al. |
| 8,383,796 B2 | 2/2013 | Korman et al. |
| 8,728,474 B2 | 5/2014 | Honjo et al. |
| 8,779,105 B2 | 7/2014 | Korman et al. |
| 9,084,776 B2 | 7/2015 | Korman et al. |
| 9,102,725 B2 | 8/2015 | Korman et al. |
| 9,212,224 B2 * | 12/2015 | Cogswell ........... C07K 16/2827 |
| 9,273,135 B2 | 3/2016 | Korman et al. |
| 9,358,289 B2 | 6/2016 | Korman et al. |
| 9,387,247 B2 | 7/2016 | Korman et al. |
| 9,492,539 B2 | 11/2016 | Korman et al. |
| 9,492,540 B2 | 11/2016 | Korman et al. |
| 9,856,320 B2 | 1/2018 | Cogswell et al. |
| 10,072,082 B2 * | 9/2018 | Cogswell ........... C07K 16/2827 |
| 10,138,299 B2 * | 11/2018 | Cogswell ........... C07K 16/2827 |
| 2002/0102651 A1 | 8/2002 | Freeman |

(Continued)

FOREIGN PATENT DOCUMENTS

| | | |
|---|---|---|
| CN | 101215329 A | 7/2008 |
| CN | 102833441 A | 12/2012 |

(Continued)

OTHER PUBLICATIONS

Petrylak et al. BJU Int. (2010) 105(3): 317-321.*

(Continued)

*Primary Examiner* — Ilia I Osupenski

(74) *Attorney, Agent, or Firm* — Sterne, Kessler, Goldstein & Fox P.L.L.C.

(57) ABSTRACT

The disclosure provides a method for immunotherapy of a subject afflicted with cancer, comprises administering to the subject a composition comprising a therapeutically effective amount of an antibody that inhibits signaling from the PD-1/PD-L1 signaling pathway. This disclosure also provides a method for immunotherapy of a subject afflicted with cancer comprising selecting a subject that is a suitable candidate for immunotherapy based on an assessment that the proportion of cells in a test tissue sample from the subject that express PD-L1 on the cell surface exceeds a predetermined threshold level, and administering a therapeutically effective amount of an anti-PD-1 antibody to the selected subject. The invention additionally provides rabbit mAbs that bind specifically to a cell surface-expressed PD-L1 antigen in a FFPE tissue sample, and an automated IHC method for assessing cell surface expression in FFPE tissues using the provided anti-PD-L1 Abs.

30 Claims, 24 Drawing Sheets

Specification includes a Sequence Listing.

(56) References Cited

U.S. PATENT DOCUMENTS

| | | | |
|---|---|---|---|
| 2003/0039653 | A1 | 2/2003 | Chen |
| 2006/0110383 | A1 | 5/2006 | Honjo et al. |
| 2009/0055944 | A1 | 2/2009 | Korman et al. |
| 2009/0215812 | A1 | 8/2009 | Bedrosian |
| 2009/0217401 | A1 | 8/2009 | Korman et al. |
| 2009/0304711 | A1 | 12/2009 | Pardoll et al. |
| 2009/0317368 | A1 | 12/2009 | Chen |
| 2010/0015642 | A1 | 1/2010 | Kwon et al. |
| 2010/0151447 | A1 | 6/2010 | Ely |
| 2010/0203056 | A1 | 8/2010 | Irving et al. |
| 2011/0008369 | A1 | 1/2011 | Finnefrock et al. |
| 2011/0206701 | A1 | 8/2011 | Afar |
| 2011/0244546 | A1 | 10/2011 | Hansen et al. |
| 2011/0250201 | A1 | 10/2011 | Smith |
| 2011/0269948 | A1 | 11/2011 | Sanjuan |
| 2015/0125463 | A1 | 5/2015 | Cogswell et al. |
| 2015/0290316 | A1 | 10/2015 | Graziano et al. |
| 2016/0022814 | A1 | 1/2016 | Petit et al. |
| 2016/0075782 | A1 | 3/2016 | Korman et al. |
| 2016/0090417 | A1 | 3/2016 | Cogswell et al. |
| 2016/0362489 | A1 | 12/2016 | Yang |
| 2016/0362495 | A1 | 12/2016 | Korman et al. |
| 2017/0028040 | A1 | 2/2017 | Lan et al. |
| 2017/0088626 | A1 | 3/2017 | Jure-Kunkel et al. |
| 2018/0273624 | A1* | 9/2018 | Cogswell ............ C07K 16/2827 |
| 2018/0282413 | A1 | 10/2018 | Cogswell et al. |
| 2018/0282414 | A1* | 10/2018 | Cogswell ............ C07K 16/2827 |
| 2018/0312590 | A1* | 11/2018 | Cogswell ............ C07K 16/2827 |
| 2018/0319887 | A1* | 11/2018 | Cogswell ............ C07K 16/2827 |

FOREIGN PATENT DOCUMENTS

| | | |
|---|---|---|
| WO | WO 00/37504 | 3/2001 |
| WO | WO 01/14424 | 3/2001 |
| WO | WO 01/14556 | 3/2001 |
| WO | WO 01/14557 | 3/2001 |
| WO | WO 01/21631 | 6/2001 |
| WO | WO 01/39722 | 10/2002 |
| WO | WO 02/078731 | 10/2002 |
| WO | WO 02/079499 | 10/2002 |
| WO | WO 02/086083 | 5/2003 |
| WO | WO 03/042402 | 1/2004 |
| WO | WO 2004/004771 | 7/2004 |
| WO | WO 2004/056875 | 8/2004 |
| WO | WO 2004/072286 | 8/2004 |
| WO | WO 2006/042237 | 4/2006 |
| WO | WO 2006/121168 | 11/2006 |
| WO | WO 2006/133396 A2 | 12/2006 |
| WO | WO 2007/005874 | 1/2007 |
| WO | WO 2011/066389 | 6/2011 |
| WO | WO 2012/145493 | 10/2012 |

OTHER PUBLICATIONS

Roupret et al. European Urology (2011) 59: 584-594.*
Joung et al. International Journal of Urology (2011) 18: 350-357.*
U.S. Appl. No. 16/213,960, filed Dec. 2018, Cogswell; John P.*
U.S. Appl. No. 16/213,954, filed Dec. 2018, Cogswell; John P.*
Androsky, D.J. et al., "Programmed Death Ligand 1 is Expressed by Non-Hodgkin Lymphomas and Inhibits the Activity of Tumor-Associated T Cells", Clinical Cancer Research, vol. 17, No. 13, pp. 4232-4244 (2011).
Blank, C. et al., "Interaction of PO-L 1 on tumor cells with PD-1 on tumorspecific T cells as a mechanism of immune evasion: implications for tumor immunotherapy", Cancer Immunol. Immunother., vol. 54, pp. 307-314 (2005).
Blank, C. et al., "PO-L 1/B7H-1 Inhibits the Effector Phase of Tumor Rejection by T Cell Receptor (TCR) Transgenic CDS+ T Cells", Cancer Research, vol. 64, pp. 1140-1145 (2004).
Brahmer, J.R. et al., "Phase I Study of Single-Agent Anti-Programmed Death-1 (MDX-1106) in Refractory Solid Tumors: Safety, Clinical Activity, Pharmacodynamics, and Immunologic Correlates", Journal of Clinical Oncology, vol. 2S, No. 19, pp. 3167-3175 (2010).
Brahmer, J.R. et al., "Safety and Activity of Anti-PO-L 1 Antibody in Patients with Advanced Cancer", The New England Journal of Medicine, vol. 366, No. 26, pp. 2455-2465 (2012).
Brown, J.A. et al., "Blockade of Programmed Death-1 Ligands on Dendritic Cells Enhances T Cell Activation and Cytokine Production", The Journal of Immunology, vol. 170, pp. 1257-1266 (2003).
Carter, L.L. et al., "PD-1:PD-L inhibitory pathway affects both CD4+ and CDS+ T cells and is overcome by IL-2", Eur. J. Immunol., vol. 32, pp. 634-643 (2002).
Dasanu, C.A. et al., "Immune alterations and emerging immunotherapeutic approaches in lung cancer", Expert Opin. Bioi. Ther., vol. 12, No. 7, pp. 923-937 (2012).
Dodson, L.F. et al., "Potential targets for pancreatic cancer immunotherapeutics", Immunotherapy, vol. 3, No. 4, pp. 517-537 (2011).
Dong, H. et al., "B7-H1 pathway and its role in the evasion of tumor immunity", J. Mol. Med; vol. 31, pp. 231-237 (2003).
Dong, H. et al., "Tumor-associated B7-H1 promotes T-cell apoptosis: A potential mechanism of immune evasion", Nature Medicine, vol. S, No. S, pp. 793-SOO (2002).
Flies, D. B. et al., "Blockade of the B7-H1/PD-1 Pathway for Cancer Immunotherapy", Yale Journal of Biology and Medicine, vol. S4, pp. 409-421 (2011).
Freeman, G.J. et al., "Engagement of the PD-1 Immunoinhibitory Receptor by a Novel B7 Family Member Leads to Negative Regulation of Lymphocyte Activation", J. Exp. Med., vol. 192, No. 7, pp. 1027-1034 (2000).
Gadiot, J. et al., "Overall Survival and PO-L 1 Expression in Metastasized Malignant Melanoma", Cancer, vol. 117, pp. 2192-2201 (2011).
Gajewski, T.F. et al., "Gene Signature in Melanoma Associated with Clinical Activity: A Potential Clue to Unlock Cancer Immunotherapy", The Cancer Journal, vol. 16, No. 4, pp. 399-403 (2010).
Garbe, C. et al., "Diagnosis and treatment of melanoma. European consensus-based interdisciplinary guideline—Update 2012", European Journal of Cancer, vol. 48, pp. 2375-2390 (2012).
Hamanishi, J. et al., "Programmed cell death 1 ligand 1 and tumor-infiltrating cos+ T lymphocytes are prognostic factors of human ovarian cancer", Proc. Natl. Acad. Sci., vol. 104, No. 9, pp. 3360-3365 (2007).
Hamid, 0. et al., "Anti-programmed death-1 and anti-programmed deathligand 1 antibodies in cancer therapy", Expert Opin. Bioi. Ther., vol. 13, No. 6, pp. 847-861 (2013).
He, Y.-F. et al., "Blocking Programmed Death-1 Ligand-PD-1 Interactions by Local Gene Therapy Results in Enhancement of Antitumor Effect of Secondary Lymphoid Tissue Chemokine", The Journal of Immunology, vol. 173, pp. 4919-4928 (2004).
Hino, R. et al., "Tumor Cell Expression of Programmed Cell Death-1 Ligand 1 is a Prognostic Factor for Malignant Melanoma", Cancer, vol. 116, pp. 1757-1766 (2010).
Hirano, F. et al., "Blockade of B7-H1 and PD-1 by Monoclonal Antibodies Potentiates Cancer Therapeutic Immunity", Cancer Res., vol. 65, No. 3, pp. 1 089-1 096 (2005).
Holt, G. E. et al., "Immune Modulation as a Therapeutic Strategy for Non-Small-Cell Lung Cancer", Clinical Lung Cancer, vol. 9, Suppl. 1, pp. S13-S19 (2008).
Holt, G. E. et al., "Immunotherapy as a strategy for the treatment of nonsmall-cell lung cancer", Therapy, vol. 8, No. 1, pp. 43-54 (2011).
Iwai, Y. et al., "Involvement of PO-L 1 on tumor cells in the escape from host immune system and tumor immunotherapy by PO-L 1 blockade", Proc. Natl. Acad. Sci., vol. 99, No. 19, pp. 12293-12297 (2002).
Iwai, Y. et al., "PD-1 blockade inhibits hematogenous spread of poorly immunogenic tumor cells by enhanced recruitment of effector T cells", International Immunology, vol. 17, No. 2, pp. 133-144 (2004).
Kim, P.S. et al., "Features of responding T cells in cancer and chronic infection", Current Opinion in Immunology, vol. 22, pp. 223-230 (2010).

(56) References Cited

OTHER PUBLICATIONS

Konishi, J. et al., "B7-H1 Expression on Non-Small Cell Lung Cancer Cells and Its Relationship with Tumor-Infiltrating Lymphocytes and Their PD-1 Expression", Clinical Cancer Research, vol. 10, pp. 5094-5100 (2004).
Lipson, E.J. et al., "Durable Cancer Regression Off-Treatment and Effective Reinduction Therapy with an Anti-PD-1 Antibody", Clinical Cancer Research, vol. 19, No. 2, pp. 462-468 (2012).
Mellman, I. et al., "Cancer immunotherapy comes of age", Nature, vol. 480, pp. 480-489 (2011).
Pardoll, D.M., "The blockade of immune checkpoints in cancer immunotherapy", Nature Reviews: Cancer, vol. 12, pp. 252-264 (2012).
Parry, R.V. et al., "CTLA-4 and PD-1 Receptors Inhibit T-Cell Activation by Distinct Mechanisms", Molecular and Cellular Biology, vol. 25, No. 21, pp. 9543-9553 (2005).
Schreiber, R.D. et al., "Cancer Immunoediting: Integrating Immunity's Roles in Cancer Suppression and Promotion", Science, vol. 331, pp. 1565-1570 (2011).
Sharma, P. et al., "Novel cancer immunotherapy agents with survival benefit: recent successes and next steps", Nature Reviews: Cancer, vol. 11, pp. 805-812 (2011).
Shepherd, F.A. et al., "Immunotherapy for Non-small Cell Lung Cancer: Novel Approaches to Improve Patient Outcome", Journal of Thoracic Oncology, vol. 6, No. 10, pp. 1763-1773 (2011).
Sompuram, S.R. et al., "Antibodies Immunoreactive with Formalin-Fixed Tissue Antigens Recognize Linear Protein Epitopes", Am. J. Clin. Pathol., vol. 125, pp. 82-90 (2006).
Taube, J.M. et al., "Colocalization of Inflammatory Response with B7-H1 Expression in Human Melanocytic Lesions Supports an Adaptive Resistance Mechanism of Immune Escape", Science Translational Medicine, vol. 4, No. 127, 127ra37 (2012), and Supplementary Materials, http:l/stm.sciencemag.org/content/suppl/2012/03/26/4.127 .127ra37 .DC 1. Html.
Topalian, S.L. et al., "Cancer Immunotherapy Comes of Age", Journal of Clinical Oncology, vol. 29, No. 36, pp. 4828-4836 (2011).
Topalian, S.L. et al., "Safety, Activity, and Immune Correlates of Anti-PD-1 Antibody in Cancer", The New England Journal of Medicine, vol. 366, No. 26, pp. 2443-2454 (2012).
Topalian, S.L. et al. "Targeting the PD-1/B7-H1 (PO-L 1) pathway to activate anti-tumor immunity", Current Opinion in Immunology, vol. 24, pp. 207-212 (2012).
Wolchok, J.D. et al., "Ipilimumab monotherapy in patients with pretreated advanced melanoma: a randomised, double-blind, multicentre, phase 2, dose-ranging study", Lancet Oncol., vol. 11, pp. 155-164 (2010).
Wong, R.M. et al., "Programmed death-1 blockade enhances expansion and functional capacity of human melanoma antigen-specific CTLs", International Immunology, vol. 19, No. 10, pp. 1223-1234 (2007).
Zou, W. et al., "Inhibitory 87-family molecules in the tumour microenvironment", Nature Reviews: Immunology, vol. 8, pp. 467-477 (2008).
International Preliminary Report on Patentability and Written Opinion for International Application No. PCT/US2013/040764, The International Bureau of WIPO, Geneva, Switzerland, dated Nov. 18, 2014, 10 pages.
International Search Report for International Application No. PCT/US2013/040764, European Patent Office, Netherlands, dated Oct. 31, 2013, 8 pages.
Ascierto, P.A., et al., "Clinical experiences with anti-CD137 and anti-PD1 therapeutic antibodies," Semin Oncol 37(5):508-516, Elsevier Inc., United States (2010).
National Institutes of Health Clinical Center, Clinical Trial Identifier NCT01024231 entitled "Dose-escalation Study of Combination BMS-936558 (MDX-1106) and Ipilimumab in Subjects With Unresectable Stage III or Stage IV Malignant Melanoma," ClinicalTrials.gov, available at https://clinicaltrials.gov/ct2/show/NCT01024231?term=NCT01024231&rank=1, last accessed on Jun. 30, 2017, 7 pages (same clinical trial accessed on Apr. 27, 2017 in related U.S. Appl. No. 14/400,667, filed Nov. 12, 2014).
Curran, M.A., et al., "PD-1 and CTLA-4 combination blockade expands infiltrating T cells and reduces regulatory T and myeloid cells within B16 melanoma tumors," Proc Natl Acad Sci USA 107(9):4275-4280, National Academy of Sciences, United States (2010).
May Jr., K.F., et al., "Prostate Cancer Immunotherapy," Clinical Cancer Research 17(16):5233-5238, American Association of Cancer Research, United States (2011).
Natarajan, N., et al., "Novel immunotherapeutic agents and small molecule antagonists of signalling kinases for the treatment of metastatic melanoma," Drugs 71(10):1233-1250, Springer International, New Zealand (2011).
Office Action dated Nov. 9, 2017 in U.S. Appl. No. 14/950,748, inventor Cogswell, J.P., et al., filed Nov. 24, 2015, 11 pages.
Postow, M.A., et al., "Targeting Immune Checkpoints: Releasing the Restraints on Antitumor Immunity for Patients With Melanoma," Cancer Journal 18(2):153-159, Lippincott Williams & Wilkins, United States (2012).
Sznol, M., "Advances in the treatment of metastatic melanoma: new immunomodulatory agents," Semin Oncol. 39(2):192-203, Elsevier Inc., United States (2012).
Wolchok, J.D., "Immunobiology of immune checkpoints," Pigment Cell Research 24:1005, John Wiley & Sons A/S, United States (2011).
National Institutes of Health, "Dose-escalation Study of Combination BMS-936558 (MDX-1106) and Ipilimumab in Subjects With Unresectable Stage III or Stage IV Malignant Melanoma," ClinicalTrials.gov Identifier NCT01024231, accessed at https://web.archive.org/web/20111023232455/https://clinicaltrials.gov/ct2/show/NCT01024231, accessed on Sep. 22, 2017, 3 pages.
Shibayama, S. and Yoshida, T., "Development of ONO-4538, fully human anti-PD-1 antibody for malignant tumors," Medical Science Digest 36(12):1120-1123, New Science Co., Japan (2010).
Wang, G. et al., "A Therapeutic strategy of targeting PD1/PDL signal pathway," Chinese Bulletin of Life Sciences 23:86-89, (2011).
Gao, Q., et al., "Overexpression of PD-L1 Significantly Associates with Tumor Aggressiveness and Postoperative Recurrence in Human Hepatocellular Carcinoma," Clinical Cancer Research 15(3);971-979, American Association for Cancer Research, United States (2009).
Ghebeh, H., et al., The B7-H1 (PD-L1) T Lymphocyte-Inhibitory molecule Is Expressed in Breast cancer Patients with Infiltrating Ductal Carcinoma: Correlation with Important high-Risk Prognostic Factors Neoplasia 8(3):190-198, Elsevier, Netherlands (2006).
Roth, T., et al., "B7-H3 Ligand Expression by Prostate Cancer: A Novel Marker of Prognosis and Potential Target for Therapy," Cancer Res 67(16):7893-7900, American Association for Cancer, United States (2007).
National Institutes of Health Clinical Center, Clinical Trial Identifier NCT01024231 entitled "Dose-escalation Study of Combination BMS-936558 (MDX-1106) and Ipilimumab in Subjects With Unresectable Stage III or Stage IV Malignant Melanoma," ClinicalTrials.gov, available at https://clinicaltrials.gov/archive/NCT01024231/2012_04_30, last accessed on Jul. 18, 2017, 4 pages (same clinical trial accessed on Apr. 27, 2017 in same application).
Study NCT01024231 , "Dose-Escalation Study of Combination BMS-936558 (MDX-1106) and Ipilimumab in Subjects with Unresectable Stage III or Stage IV Malignant Melanoma," Apr. 18, 2012, 3 pages.
Simeone, E., et al., "Immunotreatment of metastatic melanoma: the experience with anti-CTLA-4," Journal of Immunotoxicology 9(3):21-247, Taylor & Francis, United Kingdom (2012).
Wolchok, J.D., et a., "Nivolumab Plus Ipilimumab in Advanced Melanoma," New England Journal of Medicine 369(2):122-133, Massachusetts Medical Society, United States (2012).
Phase 3 study of Nivolumab, or Nivolumab Plus Ipilimumab Versus Ipilimumab alone in Previously Untreated Advanced Melanoma (Checkmate 067), last updated Dec. 18, 2017.
Kuenen, B., et al., "A Phase 1 Pharmacologic Study of Necitumumab (IMC-11F8), a Fully Human IgG1 Monoclonal Antibody Directed Against EGFR in Patients with Advanced Solid Malignancies,"

(56) References Cited

OTHER PUBLICATIONS

Clinical Cancer Research 16:1915-1923, American Association for Cancer Research, United States (2010).
Seiwert, T.Y., et al., "Safety and clinical activity of pembrolizumab for treatment of recurrent or metastatic squamous cell carcinoma of the head and neck (KEYNOTE 0-12): an open-label, multicenter, phase 1b trial." Lancet Oncology 17:956-965, Elsevier, Netherlands (2016).
Wang, D., et al., "Fixed Dosing Versus Body Size-based Dosing of Monoclonal Antibodies in Adult Clinical Trials," J. Clin Pharmacol 49:1012-1024, John Wiley & Sons, United States (2009).
American Cancer Society, "What is Non-Small Cell Lung Cancer'?," retrieved from https://www.cancer.org/cancer/non-small-cell-lung-cancer/about/what-is-non-small-cell-lung- cancer.html, retrieved on Aug. 6, 2018. 5 pages.
Auperin, A., et al., "Meta-Analysis of Concomitant versus Sequential Radiochemotherapy in Locally Advanced Non-Small-Cell Lung Cancer," Journal of Clinical Oncology 28(13):2181-2190, American Society of Clinical Oncology Journal, United States (2010).
Clark, P., et al., "Bladder Cancer," Journal of the National Comprehensive Cancer Network 11(4):446-475, Harborside Press, United States (Apr. 2013).
Leighl, N.B., "Treatment paradigms for Patients with metastatic non-small-cell lung cancer: first-, second-, and third-line," Curr Oncol, 19:S52-S58, Multimed Inc., Canada (Jun. 2012).
Office Action dated Aug. 15, 2018, in U.S. Appl. No. 16/024,340, inventors Cogswell, et al., filed Jun. 29, 2018, 7 pages.
Office Action dated Oct. 18, 2018 in U.S. Appl. No. 16/024,340, inventors Cogswell, et al., filed Jun. 29, 2018, 5 pages.
Office Action dated Aug. 10, 2018, in U.S. Appl. No. 16/006,493, inventors Cogswell, et al., filed Jun. 12, 2018, 9 pages.
Office Action dated Aug. 15, 2018, in U.S. Appl. No. 16/024,333, inventors Cogswell, et al., filed Jun. 29, 2018, 10 pages.
Office Action dated Aug. 10, 2018, in U.S. Appl. No. 16/006,365, inventors Cogswell, et al., filed Jun. 12, 2018, 9 pages.
Office Action dated Dec. 14, 2018, in U.S. Appl. No. 16/006,365, inventors Cogswell, et al., filed Jun. 12, 2018, 8 pages.
Atmar, J., et al., "Review of the safety and feasibility of rapid infusion rituximab," Journal of Oncology Practice 6(2):91-93, American Society of Clinical Oncology, United States (2009).
Hawker, K., et al., "Safe Administration and Monitoring of Monoclonal Antibodies in Treatment of Multiple Sclerosis," International Journal of MS Care 9(2):1-23, Bentham Science Publishers, United States (2007).
Lenz, H-J., et al., "Management and Preparedness for Infusion and Hypersensitivity reactions," The Oncologist 12:601-609, AlphaMed Press, United States (2007).
Reiss, K.A., et al,. "Harnessing the power of the immune system via blockade of PD-1 and PD-L1: a promising new anticancer strategy," Immunotherapy 6(4):459-475, Future Medicine, United Kingdom (2014).
Vogel, W.H., "Infusion reactions: diagnosis, assessment, and management," Clin J. Oncol Nurs 14(2):E10-E21, Oncology Nursing Society, United States (2010).
Office Action dated Jan. 8, 2019, in U.S. Appl. No. 16/213,954, inventors Cogswell, et al., filed Dec. 7, 2018, 8 pages.
Office Action dated Jan. 8, 2019, in U.S. Appl. No. 16/213,960, inventors Cogswell, et al., filed Dec. 7, 2018, 8 pages.
Co-pending U.S. Appl. No. 16/213,954, inventors Cogswell, John, P., filed Dec. 7, 2018 (Not Published).
Co-pending U.S. Appl. No. 16/213,960, inventors Cogswell, John, P., filing date: To Be Assigned (Not Published).
Co-pending U.S. Appl. No. 16/230,657, inventors Cogswell, John, P., filed Dec. 21, 2018 (Not Published).
Co-pending U.S. Appl. No. 16/231,211, inventors Cogswell, John, P., filed Dec. 21, 2018 (Not Published).
Petrylak, P.P., et al., "Results of the Southwest Oncology Group phase II evaluation (study S0031) of ZD1839 for advanced transitional cell carcinoma of the urothelium," *BJU 105*:317-21, Southwest Oncology Group (2009).
Roupret, M., et al., "European Guidelines for the Diagnosis and Management of Upper Urinary Tract Urothelial Cell Carcinomas: 2011 Update," *European Urology 59*:584-94, European Association of Urology (2011).
Joung, J.Y., et al., "Paclitaxel and cisplatin chemotherapy for metastatic urothelial carcinoma after failure of two courses of platinum-based regimens," *Int'l J. Urology 18*:350-57, The Japanese Urological Association (2011).
Office Action dated Jan. 18, 2019, in U.S. Appl. No. 16/230,657, inventors Cogswell, et al., filed Dec. 21, 2018, 13 pages.
Office Action dated Jan. 22, 2019, in U.S. Appl. No. 16/231,211, inventors Cogswell, et al., filed Dec. 21, 2018, 15 pages.

\* cited by examiner

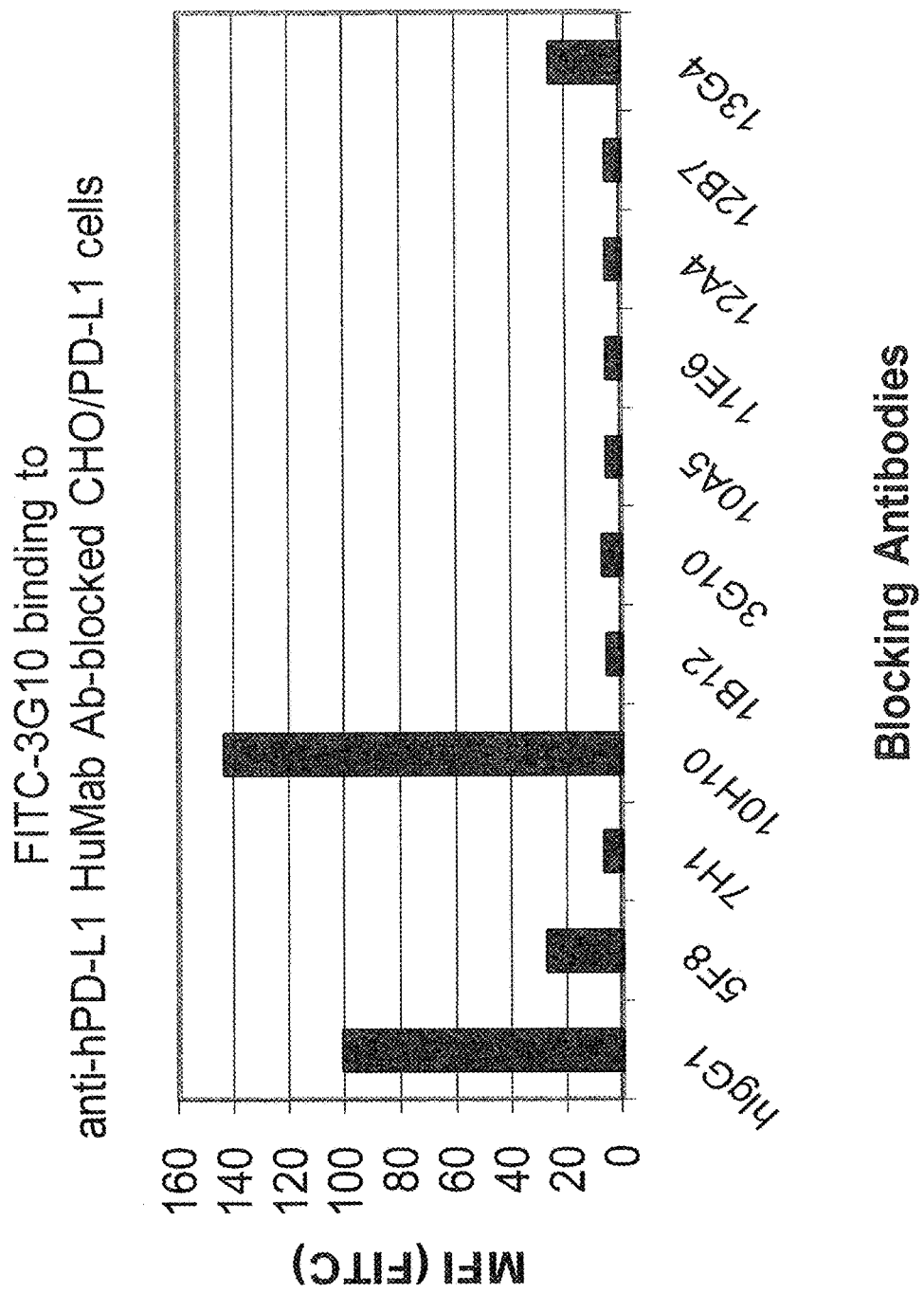

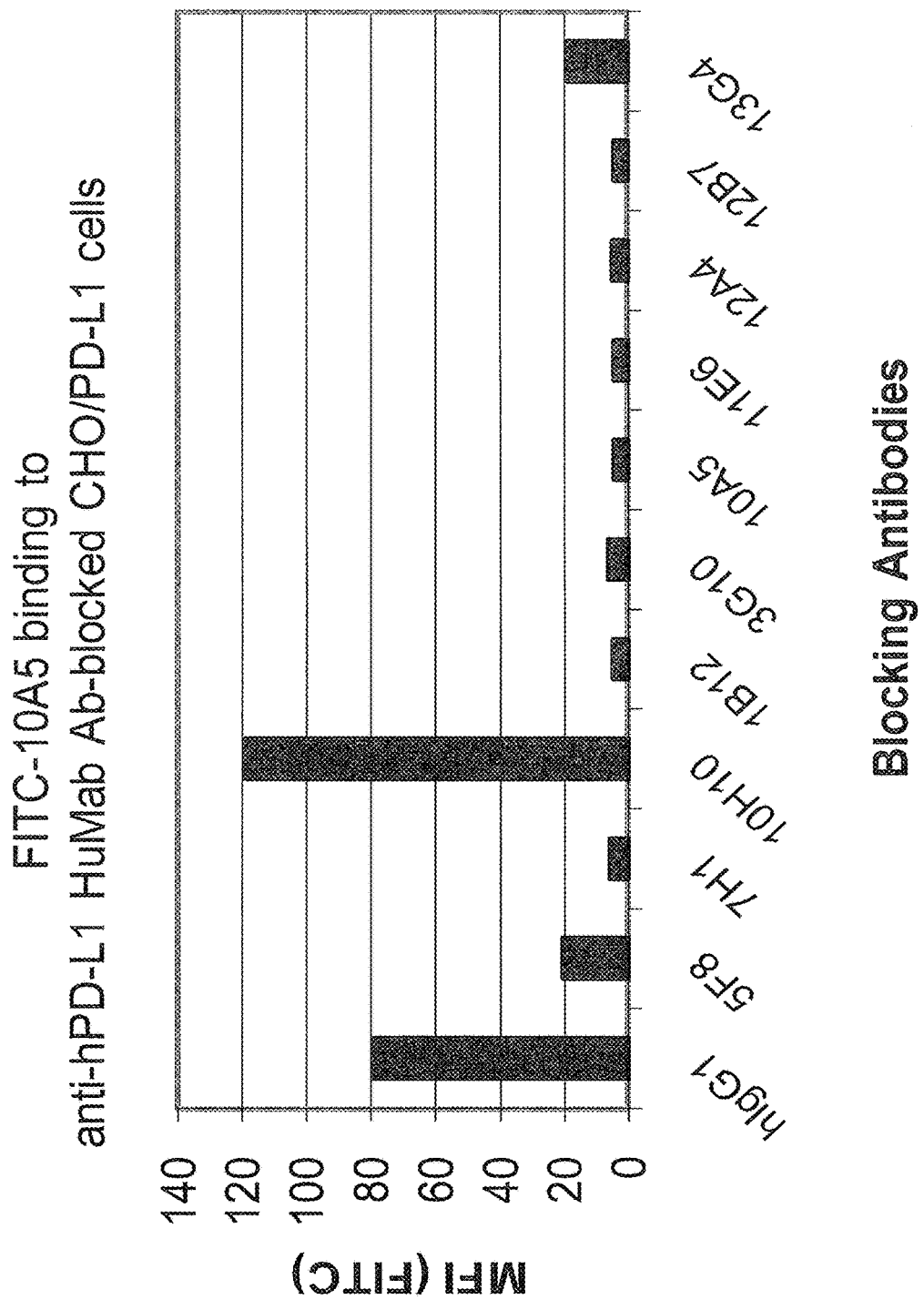

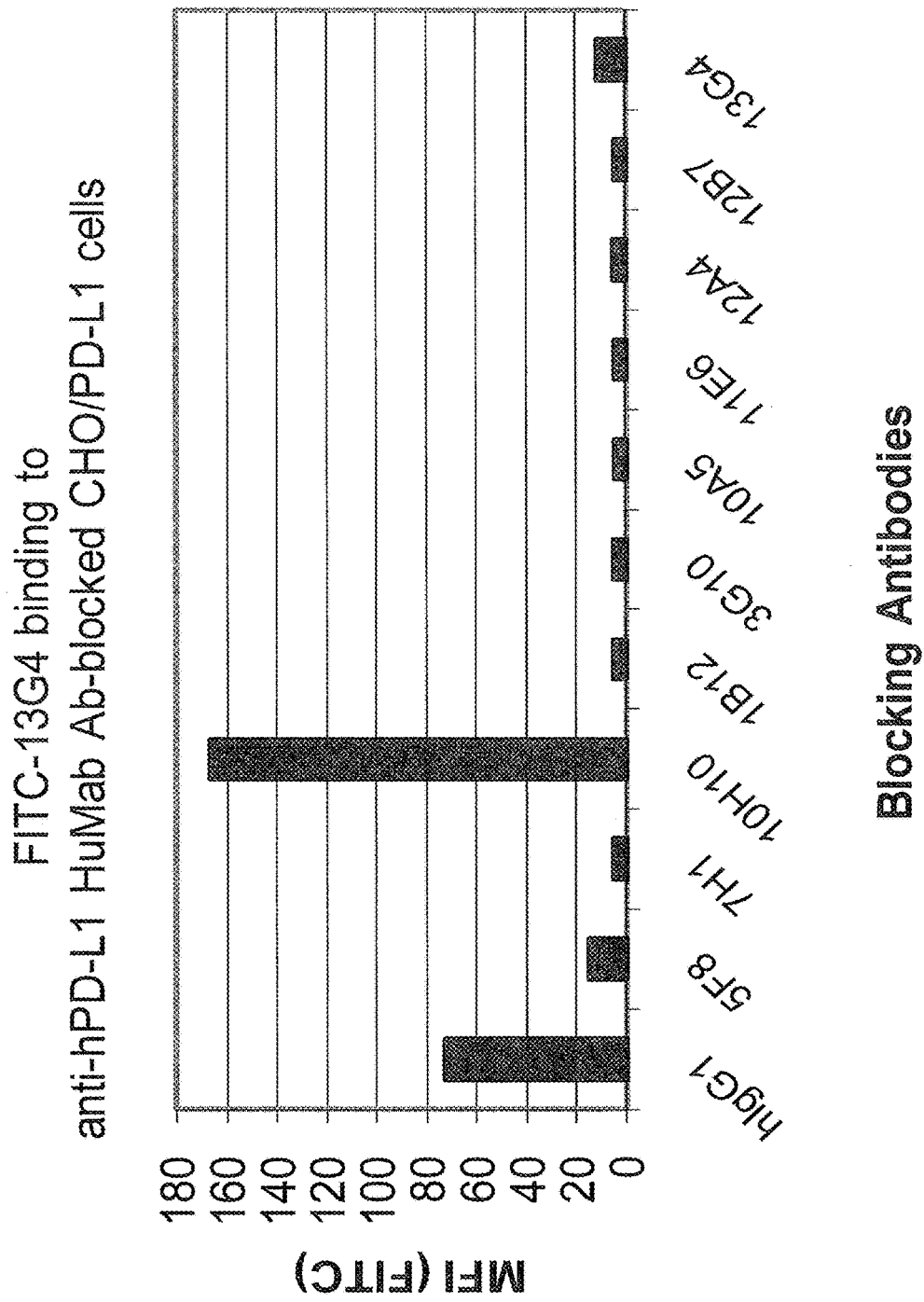

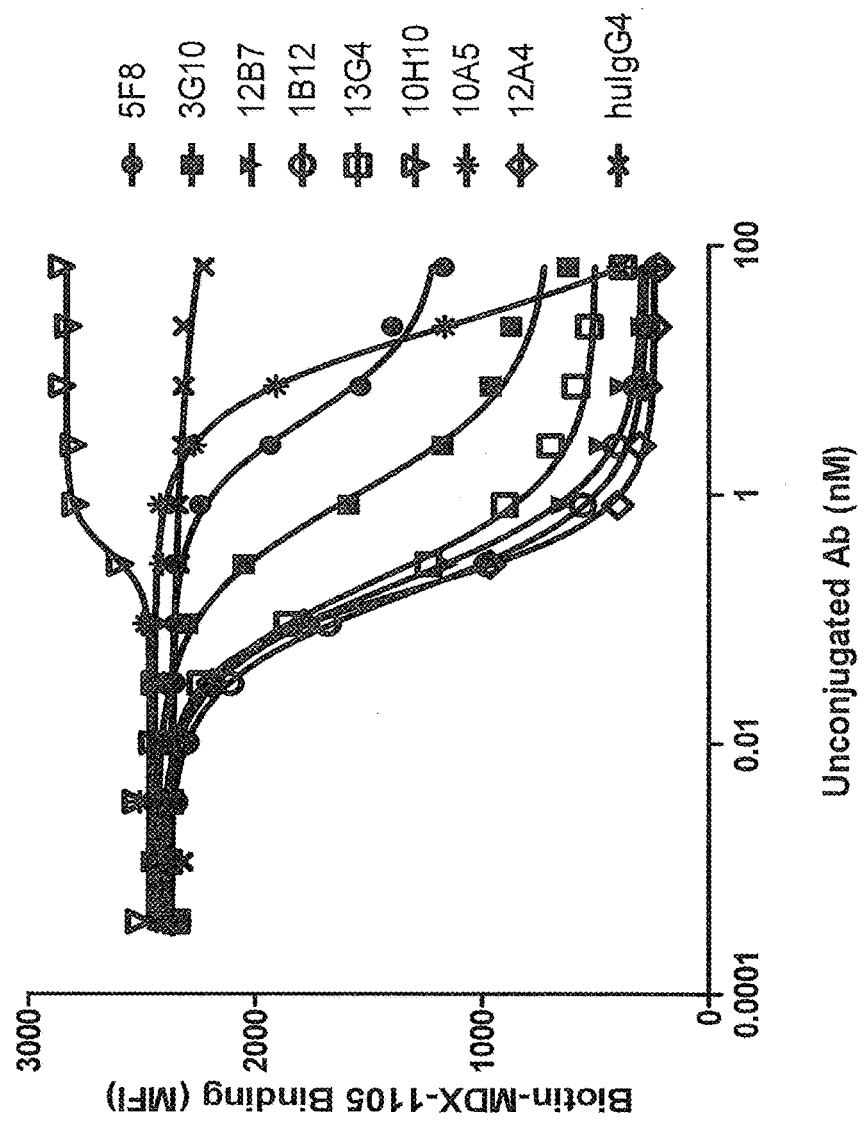

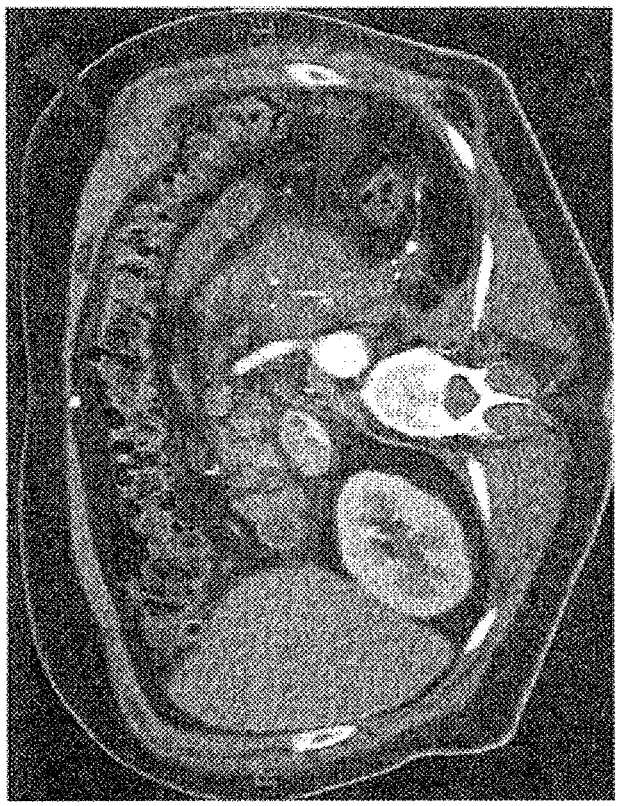
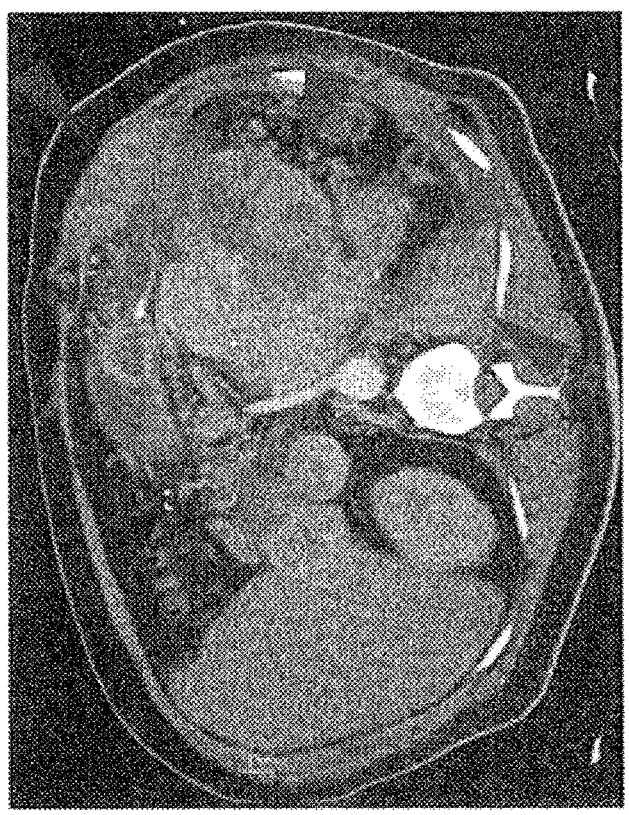
FIG. 5

| Association Between Pretreatment Tumor PD-L1 Expression and Clinical Response | | | |
|---|---|---|---|
| Response Status | PD-L1-Positive no. (%) | PD-L1-Negative no. (%) | Total no. (%) |
| CR/PR | 9 (36) | 0 | 9 (21) |
| Nonresponder | 16* (64) | 17 (100) | 33 (79) |
| All Patients | 25 | 17 | 42 |

Fisher's exact test for association P=0.006.

*Two patients categorized as nonresponders at the time of data analysis are still under evaluation.

CANCER IMMUNOTHERAPY BY DISRUPTING PD-1/PD-L1 SIGNALING

REFERENCE TO EARLIER FILED APPLICATIONS

This application is a continuation of U.S. application Ser. No. 16/006,365, filed Jun. 12, 2018, which is a continuation of U.S. application Ser. No. 14/950,748, filed Nov. 24, 2015, (issued as U.S. Pat. No. 10,072,082 on Sep. 11, 2018), which is a division of U.S. application Ser. No. 13/892,671, filed May 13, 2013 (issued as U.S. Pat. No. 9,212,224 on Dec. 15, 2015), which claims the benefit of U.S. Provisional Application No. 61/647,442, filed May 15, 2012, and U.S. Provisional Application No. 61/790,747, filed Mar. 15, 2013, all of which are incorporated herein by reference in their entireties.

REFERENCE TO SEQUENCE LISTING SUBMITTED ELECTRONICALLY VIA EFS-WEB

The content of the electronically submitted sequence listing (Name: 3338_063000D_SequenceListing_ST25.txt, Size: 37,964 bytes; and Date of Creation: Dec. 7, 2018) is incorporated herein by reference in its entirety.

Throughout this application, various publications are referenced in parentheses by author name and date, or by Patent No. or Patent Publication No. Full citations for these publications may be found at the end of the specification immediately preceding the claims. The disclosures of these publications are hereby incorporated in their entireties by reference into this application in order to more fully describe the state of the art as known to those skilled therein as of the date of the invention described and claimed herein. However, the citation of a reference herein should not be construed as an acknowledgement that such reference is prior art to the present invention.

FIELD OF THE INVENTION

This invention relates to methods for immunotherapy of a cancer patient comprising administering to the patient antibodies that disrupt the PD-1/PD-L1 signaling pathway. A biomarker may be used as part of this treatment for identifying suitable patients for immunotherapy and for predicting the efficacy of anti-PD-1 treatment.

BACKGROUND OF THE INVENTION

Human cancers harbor numerous genetic and epigenetic alterations, generating neoantigens potentially recognizable by the immune system (Sjoblom et al., 2006). Although an endogenous immune response to cancer is observed in preclinical models and patients, this response is ineffective, and established cancers are viewed as "self" and tolerated by the immune system. Contributing to this state of tolerance, tumors may exploit several distinct mechanisms to actively suppress the host immune response (Topalian et al., 2011; Mellman et al., 2011). Among these mechanisms, endogenous "immune checkpoints" that normally terminate immune responses to mitigate collateral tissue damage can be co-opted by tumors to evade immune destruction. Intensive efforts to develop specific immune checkpoint pathway inhibitors have begun to provide new immunotherapeutic approaches for treating cancer, including the development of the anti-CTLA-4 antibody (Ab), ipilimumab (YERVOY®), for the treatment of patients with advanced melanoma (Hodi et al., 2010).

Programmed Death-1 (PD-1) is a key immune checkpoint receptor expressed by activated T and B cells and mediates immunosuppression. PD-1 is a member of the CD28 family of receptors, which includes CD28, CTLA-4, ICOS, PD-1, and BTLA. Two cell surface glycoprotein ligands for PD-1 have been identified, Programmed Death Ligand-1 (PD-L1) and Programmed Death Ligand-2 (PD-L2), that are expressed on antigen-presenting cells as well as many human cancers and have been shown to downregulate T cell activation and cytokine secretion upon binding to PD-1 (Freeman et al., 2000; Latchman et al., 2001). Unlike CTLA-4, PD-1 primarily functions in peripheral tissues where activated T-cells may encounter the immunosuppressive PD-L1 (B7-H1) and PD-L2 (B7-DC) ligands expressed by tumor and/or stromal cells (Flies et al., 2011; Topalian et al., 2012a). Inhibition of the PD-1/PD-L1 interaction mediates potent antitumor activity in preclinical models (U.S. Pat. Nos. 8,008,449 and 7,943,743), and the use of Ab inhibitors of the PD-1/PD-L1 interaction for treating cancer has entered clinical trials (Brahmer et al., 2010; Flies et al., 2011; Topalian et al., 2012b; Brahmer et al., 2012).

The promise of the emerging field of personalized medicine is that advances in pharmacogenomics will increasing be used to tailor therapeutics to defined sub-populations, and ultimately, individual patients in order to enhance efficacy and minimize adverse effects. Recent successes include, for example, the development of imatinib mesylate (GLEEVEC®), a protein tyrosine kinase inhibitor that inhibits the bcr-abl tyrosine kinase, to treat Philadelphia chromosome-positive chronic myelogenous leukemia (CML); crizotinib (XALKORI®) to treat the 5% of patients with late-stage non-small cell lung cancers who express a mutant anaplastic lymphoma kinase (ALK) gene; and vemurafenib (ZELBORAF®), an inhibitor of mutated B-RAF protein (V600E-BRAF) which is expressed in around half of melanoma tumors. However, unlike the clinical development of small molecule agents that target discrete activating mutations found in select cancer populations, a particular challenge in cancer immunotherapy has been the identification of mechanism-based predictive biomarkers to enable patient selection and guide on-treatment management. Advances in validating PD-L1 expression as a biomarker for screening patients for anti-PD-1 immunotherapy are described herein.

SUMMARY OF THE INVENTION

The present disclosure provides a method for immunotherapy of a subject afflicted with cancer, which method comprises administering to the subject a composition comprising a therapeutically effective amount of an agent that reduces or suppresses signaling from an inhibitory immunoregulator. In preferred embodiments, the agent is an Ab. In other preferred embodiments, the inhibitory immunoregulator is a component of the PD-1/PD-L1 signaling pathway. In further preferred embodiments, the Ab disrupts the interaction between PD-1 and PD-L1. In certain embodiments, the Ab is an anti-PD-1 Ab of the invention or an anti-PD-L1 Ab of the invention. In preferred embodiments, the anti-PD-1 Ab of the invention is nivolumab (BMS-936558) and the anti-PD-L1 Ab of the invention is BMS-936559. In certain embodiments, the subject has been pre-treated for the cancer. In other embodiments, the cancer is an advanced, metastatic and/or refractory cancer. In preferred embodiments, the administration of the antibody or antigen-binding portion to the subject thereof induces a durable clinical response in the subject.

This disclosure also provides a method for immunotherapy of a subject afflicted with cancer, which method comprises: (a) selecting a subject that is a suitable candidate for immunotherapy, the selecting comprising (i) optionally providing a test tissue sample obtained from a patient with cancer of the tissue, the test tissue sample comprising tumor cells and tumor-infiltrating inflammatory cells, (ii) assessing the proportion of cells in the test tissue sample that express PD-L1 on the cell surface, and (iii) selecting the subject as a suitable candidate based on an assessment that the proportion of cells in the test tissue sample that express PD-L1 on the cell surface exceeds a predetermined threshold level; and (b) administering a composition comprising a therapeutically effective amount of an anti-PD-1 Ab to the selected subject.

The disclosure further provides a method for treatment of a subject afflicted with cancer, which method comprises: (a) selecting a subject that is not suitable for anti-PD-1 Ab immunotherapy, the selecting comprising (i) optionally providing a test tissue sample obtained from a patient with cancer of the tissue, the test tissue sample comprising tumor cells and tumor-infiltrating inflammatory cells; (ii) assessing the proportion of cells in the test tissue sample that express PD-L1 on the cell surface; and (iii) selecting the subject as not suitable for anti-PD-1 Ab immunotherapy based on an assessment that the proportion of cells in the test tissue sample that express PD-L1 on the cell surface is less than a predetermined threshold level; and (b) administering a standard-of-care therapeutic other than an anti-PD-1 Ab to the selected subject.

In addition, the disclosure provides a method for selecting a cancer patient for immunotherapy with an anti-PD-1 Ab, which method comprises: (a) optionally providing a test tissue sample obtained from a patient with cancer of the tissue, the test tissue sample comprising tumor cells and tumor-infiltrating inflammatory cells; (b) assaying the test tissue sample to determine the proportion of cells therein that express PD-L1 on the cell surface; (c) comparing the proportion of cells that express PD-L1 on the cell surface with a predetermined threshold proportion; and (d) selecting the patient for immunotherapy based on an assessment that PD-L1 is expressed in cells of the test tissue sample.

This disclosure further provides a method for predicting the therapeutic effectiveness of an anti-PD-1 Ab for treating a cancer patient, which method comprises: (a) optionally providing a test tissue sample obtained from a patient with cancer of the tissue, the test tissue sample comprising tumor cells and tumor-infiltrating inflammatory cells; (b) assaying the test tissue sample to determine the proportion of cells therein that express PD-L1 on the cell surface; (c) comparing the proportion of cells that express PD-L1 on the cell surface with a predetermined threshold value; and (d) predicting the therapeutic effectiveness of the anti-PD-1 Ab, wherein if the proportion of cells that express PD-L1 on the cell surface exceeds the threshold proportion the Ab is predicted to be effective in treating the patient, and wherein if the proportion of cells that express PD-L1 on the cell surface is below the threshold proportion the Ab is predicted to not be effective in treating the patient.

The present disclosure also provides a method for determining an immunotherapeutic regimen comprising an anti-PD-1 Ab for treating a cancer patient, which method comprises: (a) optionally providing a test tissue sample obtained from a patient with cancer of the tissue, the test tissue sample comprising tumor cells and tumor-infiltrating inflammatory cells; (b) assaying the test tissue sample to determine the proportion of cells therein that express PD-L1 on the cell surface; (c) comparing the proportion of cells that express PD-L1 on the cell surface with a predetermined threshold proportion; and (d) determining an immunotherapeutic regimen comprising an anti-PD-1 Ab based on the determination that the proportion of cells that express PD-L1 on the cell surface exceeds the predetermined threshold proportion.

In certain embodiments of the methods described herein, the test tissue sample is a formalin-fixed and paraffin-embedded (FFPE) sample. In certain other embodiments, assessing the proportion of cells in the test tissue sample that express PD-L1 on the cell surface is achieved by immunohistochemical (IHC) staining of the FFPE sample. In preferred embodiments, the mAb 28-8 is used in an automated IHC assay to bind to PD-L1 on the surface of cells in the test tissue sample. In preferred embodiments of any of the methods disclosed herein, the cancer is melanoma (MEL), renal cell carcinoma (RCC), squamous non-small cell lung cancer (NSCLC), non-squamous NSCLC, colorectal cancer (CRC), castration-resistant prostate cancer (CRPC), hepatocellular carcinoma (HCC), squamous cell carcinoma of the head and neck, carcinomas of the esophagus, ovary, gastrointestinal tract and breast, or a hematologic malignancy such as multiple myeloma, B-cell lymphoma, T-cell lymphoma, Hodgkin's lymphoma/primary mediastinal B-cell lymphoma, and chronic myelogenous leukemia.

This invention additionally provides a mAb or antigen-binding portion thereof that binds specifically to a cell surface-expressed human PD-L1 antigen in a FFPE tissue sample. In preferred embodiments, the mAb or antigen-binding portion thereof does not bind to a cytoplasmic PD-L1 antigen in the FFPE tissue sample. In other preferred embodiments, the monoclonal Ab (mAb) is the rabbit mAb designated 28-8, 28-1, 28-12, 29-8 or 20-12.

Other features and advantages of the instant invention will be apparent from the following detailed description and examples which should not be construed as limiting. The contents of all cited references, including scientific articles, newspaper reports, GENBANK® entries, patents and patent applications cited throughout this application are expressly incorporated herein by reference.

BRIEF DESCRIPTION OF THE FIGURES

FIGS. 2A-2F. Cross-competition of FITC-conjugated human anti-hPD-L1 mAbs for binding to hPD-L1 expressed on CHO cells. A, Binding of labeled 10H10 was partially blocked by 10A5, 11E6 and 13G4 and was significantly blocked by itself; B, Binding of labeled 3G10 was significantly blocked by each of the tested anti-PD-L1 Abs except 10H10; C, Binding of labeled 10A5 was significantly blocked by each of the tested anti-PD-L1 Abs except 10H10; D, Binding of labeled 11E6 was significantly blocked by each of the tested anti-PD-L1 Abs except 10H10; and E, Binding of labeled 12A4 was significantly blocked by each of the tested anti-PD-L1 Abs except 10H10; and F, Binding of labeled 13G4 was significantly blocked by each of the tested anti-PD-L1 Abs except 10H10.

FIG. 3. Cross-competitive inhibition of binding of biotinylated mAb 12A4 to ES-2 cells by human anti-hPD-L1 mAbs. Fluorescence of bound biotin-12A4 is plotted against the concentration of unlabeled hPD-L1 HuMabs.

FIG. 5. Activity of anti-PD-1 mAb in patient with metastatic RCC. Partial regression of metastatic RCC in a 57-year-old patient treated with 5C4 at 1 mg/kg is illustrated. This patient had previously undergone radical surgery and had developed progressive disease after receiving sunitinib, temsirolimus, sorafenib, and pazopanib. Arrows show regression of recurrent tumor in the operative field.

DETAILED DESCRIPTION OF THE INVENTION

Figure 1A:
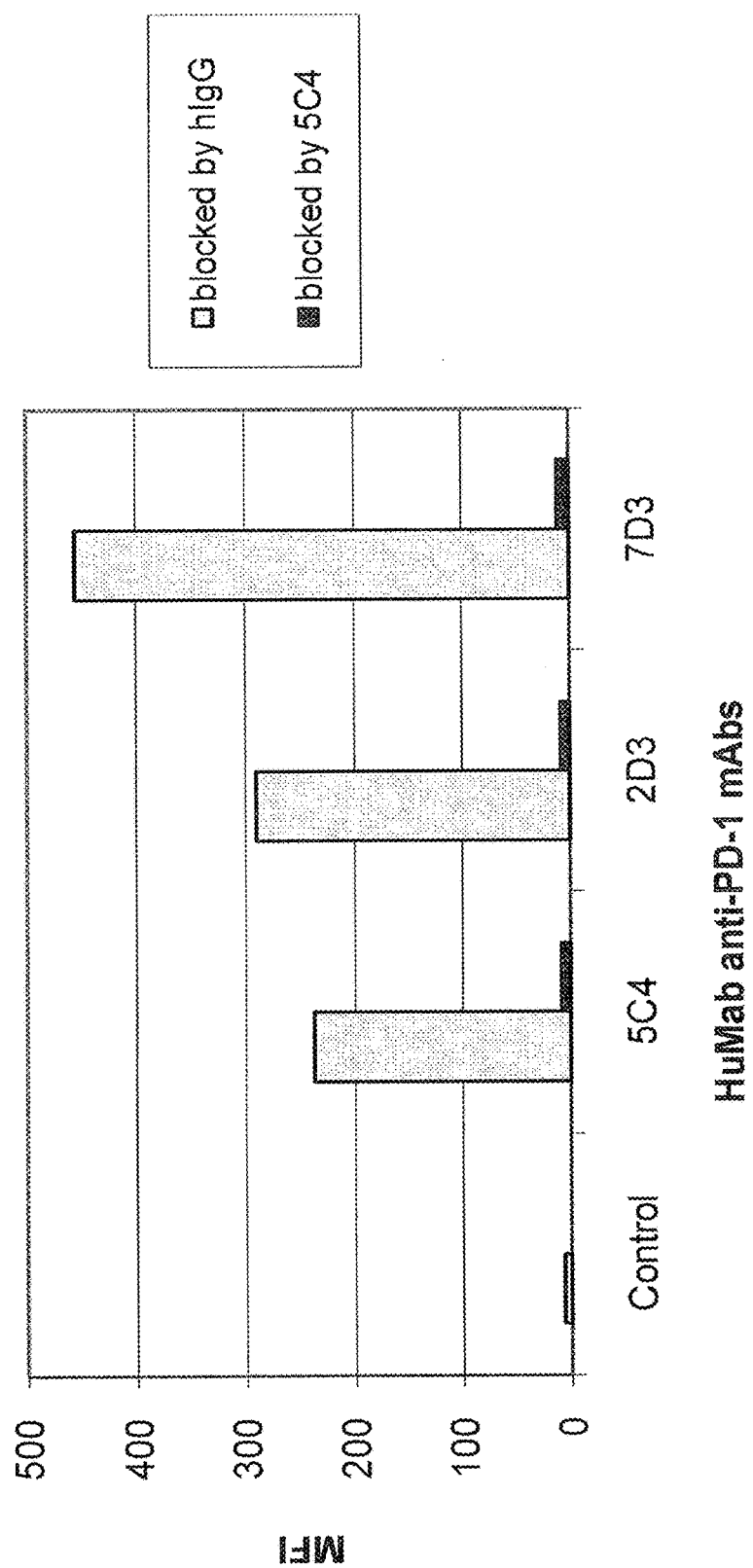
FIGS. 1A-1C. Cross-competition between 5C4 and other HuMab anti-PD-1 mAbs for binding to hPD-1 expressed on CHO cells. A, the 5C4 Fab fragment substantially blocked the binding of mAbs 5C4 itself, as well as the binding of 2D3 and 7D3; B, the 5C4 Fab fragment substantially blocked the binding of mAb 4H1; C, the 5C4 mAb substantially blocked the binding of mAb 17D8.

The present invention relates to methods for immunotherapy of a subject afflicted with diseases such as cancer or an infectious disease, which methods comprise administering to the subject a composition comprising a therapeutically effective amount of a compound or agent that potentiates an endogenous immune response, either stimulating the activation of the endogenous response or inhibiting the suppression of the endogenous response. More specifically, the disclosure provides methods for potentiating an endogenous immune response in a subject afflicted with cancer so as to thereby treat the patient, which method comprises administering to the subject a therapeutically effective amount of an Ab or an antigen-binding portion thereof that inhibits signaling from an inhibitory immunoregulator. In certain embodiments, the inhibitory immunoregulator is a component of the PD-1/PD-L1 signaling pathway. Accordingly, certain embodiments of the invention provide methods for immunotherapy of a subject afflicted with cancer, which methods comprise administering to the subject a therapeutically effective amount of an Ab or an antigen-binding portion thereof that disrupts the interaction between the PD-1 receptor and its ligand, PD-L1. In certain preferred embodiments, the Ab or antigen-binding portion thereof binds specifically to PD-1. In other preferred embodiments, the Ab or antigen-binding portion thereof binds specifically to PD-L1. In certain other embodiments, the subject is selected as suitable for immunotherapy in a method comprising measuring the surface expression of PD-L1 in a test tissue sample obtained from a patient with cancer of the tissue, for example, determining the proportion of cells in the test tissue sample that express PD-L1 on the cell surface, and selecting the patient for immunotherapy based on an assessment that PD-L1 is expressed on the surface of cells in the test tissue sample.

Terms

In order that the present disclosure may be more readily understood, certain terms are first defined. As used in this application, except as otherwise expressly provided herein, each of the following terms shall have the meaning set forth below. Additional definitions are set forth throughout the application.

"Administering" refers to the physical introduction of a composition comprising a therapeutic agent to a subject, using any of the various methods and delivery systems known to those skilled in the art. Preferred routes of administration for Abs of the invention include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. Alternatively, an Ab of the invention can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

An "adverse event" (AE) as used herein is any unfavorable and generally unintended or undesirable sign (including an abnormal laboratory finding), symptom, or disease associated with the use of a medical treatment. For example, an adverse event may be associated with activation of the immune system or expansion of immune system cells (e.g., T cells) in response to a treatment. A medical treatment may have one or more associated AEs and each AE may have the same or different level of severity. Reference to methods capable of "altering adverse events" means a treatment regime that decreases the incidence and/or severity of one or more AEs associated with the use of a different treatment regime.

An "antibody" (Ab) shall include, without limitation, a glycoprotein immunoglobulin which binds specifically to an antigen and comprises at least two heavy (H) chains and two light (L) chains interconnected by disulfide bonds, or an antigen-binding portion thereof. Each H chain comprises a heavy chain variable region (abbreviated herein as $V_H$) and a heavy chain constant region. The heavy chain constant region comprises three constant domains, $C_{H1}$, $C_{H2}$ and $C_{H3}$. Each light chain comprises a light chain variable region (abbreviated herein as $V_L$) and a light chain constant region. The light chain constant region is comprises one constant domain, $C_L$. The $V_H$ and $V_L$ regions can be further subdivided into regions of hypervariability, termed complementarity determining regions (CDRs), interspersed with regions that are more conserved, termed framework regions (FR). Each $V_H$ and $V_L$ comprises three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the Abs may mediate the binding of the immunoglobulin to host tissues or factors, including various cells of the immune system (e.g., effector cells) and the first component (C1q) of the classical complement system.

Antibodies typically bind specifically to their cognate antigen with high affinity, reflected by a dissociation constant ($K_D$) of $10^{-5}$ to $10^{-11}$ $M^{-1}$ or less. Any $K_D$ greater than about $10^{-4}$ $M^{-1}$ is generally considered to indicate nonspecific binding. As used herein, an Ab that "binds specifically" to an antigen refers to an Ab that binds to the antigen and substantially identical antigens with high affinity, which means having a $K_D$ of $10^{-7}$ M or less, preferably $10^{-8}$ M or less, even more preferably $5 \times 10^{-9}$ M or less, and most preferably between $10^{-8}$ M and $10^{-10}$ M or less, but does not bind with high affinity to unrelated antigens. An antigen is "substantially identical" to a given antigen if it exhibits a high degree of sequence identity to the given antigen, for example, if it exhibits at least 80%, at least 90%, preferably at least 95%, more preferably at least 97%, or even more preferably at least 99% sequence identity to the sequence of the given antigen. By way of example, an Ab that binds specifically to human PD-1 may also have cross-reactivity with PD-1 antigens from certain primate species but may not cross-react with PD-1 antigens from certain rodent species or with an antigen other than PD-1, e.g., a human PD-L1 antigen.

An immunoglobulin may derive from any of the commonly known isotypes, including but not limited to IgA, secretory IgA, IgG and IgM. IgG subclasses are also well known to those in the art and include but are not limited to human IgG1, IgG2, IgG3 and IgG4. "Isotype" refers to the Ab class or subclass (e.g., IgM or IgG1) that is encoded by the heavy chain constant region genes. The term "antibody" includes, by way of example, both naturally occurring and non-naturally occurring Abs; monoclonal and polyclonal Abs; chimeric and humanized Abs; human or nonhuman Abs; wholly synthetic Abs; and single chain Abs. A nonhuman Ab may be humanized by recombinant methods to reduce its immunogenicity in man. Where not expressly stated, and unless the context indicates otherwise, the term "antibody" also includes an antigen-binding fragment or an antigen-binding portion of any of the aforementioned immunoglobulins, and includes a monovalent and a divalent fragment or portion, and a single chain Ab.

An "isolated antibody" refers to an Ab that is substantially free of other Abs having different antigenic specificities (e.g., an isolated Ab that binds specifically to PD-1 is substantially free of Abs that bind specifically to antigens other than PD-1). An isolated Ab that binds specifically to PD-1 may, however, have cross-reactivity to other antigens, such as PD-1 molecules from different species. Moreover, an isolated Ab may be substantially free of other cellular material and/or chemicals. By comparison, an "isolated" nucleic acid refers to a nucleic acid composition of matter that is markedly different, i.e., has a distinctive chemical identity, nature and utility, from nucleic acids as they exist in nature. For example, an isolated DNA, unlike native DNA, is a free-standing portion of a native DNA and not an integral part of a larger structural complex, the chromosome, found in nature. Further, an isolated DNA, unlike native genomic DNA, can typically be used in applications or methods for which native genomic DNA is unsuited, e.g., as a PCR primer or a hybridization probe for, among other things, measuring gene expression and detecting biomarker genes or mutations for diagnosing disease or assessing the efficacy of a therapeutic. An isolated nucleic acid may be purified so as to be substantially free of other cellular components or other contaminants, e.g., other cellular nucleic acids or proteins, using standard techniques well known in the art. Examples of isolated nucleic acids include fragments of genomic DNA, PCR-amplified DNA, cDNA and RNA.

The term "monoclonal antibody" ("mAb") refers to a preparation of Ab molecules of single molecular composition, i.e., Ab molecules whose primary sequences are essentially identical, and which exhibits a single binding specificity and affinity for a particular epitope. A mAb is an example of an isolated Ab. MAbs may be produced by hybridoma, recombinant, transgenic or other techniques known to those skilled in the art.

A "human" antibody (HuMAb) refers to an Ab having variable regions in which both the framework and CDR regions are derived from human germline immunoglobulin sequences. Furthermore, if the Ab contains a constant region, the constant region also is derived from human germline immunoglobulin sequences. The human Abs of the invention may include amino acid residues not encoded by human germline immunoglobulin sequences (e.g., mutations introduced by random or site-specific mutagenesis in vitro or by somatic mutation in vivo). However, the term "human antibody," as used herein, is not intended to include Abs in which CDR sequences derived from the germline of another mammalian species, such as a mouse, have been grafted onto human framework sequences. The terms "human" Abs and "fully human" Abs and are used synonymously.

A "humanized" antibody refers to an Ab in which some, most or all of the amino acids outside the CDR domains of a non-human Ab are replaced with corresponding amino acids derived from human immunoglobulins. In one embodiment of a humanized form of an Ab, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the Ab to bind to a particular antigen. A "humanized" Ab retains an antigenic specificity similar to that of the original Ab.

A "chimeric antibody" refers to an Ab in which the variable regions are derived from one species and the constant regions are derived from another species, such as an Ab in which the variable regions are derived from a mouse Ab and the constant regions are derived from a human Ab.

An "antigen-binding portion" of an Ab (also called an "antigen-binding fragment") refers to one or more fragments of an Ab that retain the ability to bind specifically to the antigen bound by the whole Ab.

A "cancer" refers a broad group of various diseases characterized by the uncontrolled growth of abnormal cells in the body. Unregulated cell division and growth divide and grow results in the formation of malignant tumors that invade neighboring tissues and may also metastasize to distant parts of the body through the lymphatic system or bloodstream.

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

An "immunoregulator" refers to a substance, an agent, a signaling pathway or a component thereof that regulates an immune response. "Regulating," "modifying" or "modulating" an immune response refers to any alteration in a cell of the immune system or in the activity of such cell. Such regulation includes stimulation or suppression of the immune system which may be manifested by an increase or decrease in the number of various cell types, an increase or decrease in the activity of these cells, or any other changes which can occur within the immune system. Both inhibitory and stimulatory immunoregulators have been identified, some of which may have enhanced function in the cancer microenvironment.

The term "immunotherapy" refers to the treatment of a subject afflicted with, or at risk of contracting or suffering a recurrence of, a disease by a method comprising inducing, enhancing, suppressing or otherwise modifying an immune response. "Treatment" or "therapy" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication, condition or biochemical indicia associated with a disease.

"Potentiating an endogenous immune response" means increasing the effectiveness or potency of an existing immune response in a subject. This increase in effectiveness and potency may be achieved, for example, by overcoming mechanisms that suppress the endogenous host immune response or by stimulating mechanisms that enhance the endogenous host immune response.

A "predetermined threshold value," relating to cell surface PD-L1 expression, refers to the proportion of cells in a test tissue sample comprising tumor cells and tumor-infiltrating inflammatory cells above which the sample is scored as being positive for cell surface PD-L1 expression. For cell surface expression assayed by IHC with the mAb 28-8, the predetermined threshold value for cells expressing PD-L1 on the cell surface ranges from at least about 0.01% to at least about 20% of the total number of cells. In preferred embodiments, the predetermined threshold value for cells expressing PD-L1 on the cell surface ranges from at least about 0.1% to at least about 10% of the total number of cells. More preferably, the predetermined threshold value is at least about 5%. Even more preferably, the predetermined threshold value is at least about 1%.

The "Programmed Death-1 (PD-1)" receptor refers to an immunoinhibitory receptor belonging to the CD28 family. PD-1 is expressed predominantly on previously activated T cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1. The complete hPD-1 sequence can be found under GENBANK® Accession No. U64863.

"Programmed Death Ligand-1 (PD-L1)" is one of two cell surface glycoprotein ligands for PD-1 (the other being PD-L2) that downregulate T cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1. The complete hPD-L1 sequence can be found under GENBANK® Accession No. Q9NZQ7.

A "signal transduction pathway" or "signaling pathway" refers to the biochemical relationship between a variety of signal transduction molecules that play a role in the transmission of a signal from one portion of a cell to another portion of the cell. A "cell surface receptor" includes, for example, molecules and complexes of molecules that are located on the surface of a cell and are capable of receiving a signal and transmitting such a signal across the plasma membrane of a cell. An example of a cell surface receptor of the present invention is the PD-1 receptor, which is located on the surface of activated B cells, activated T cells and myeloid cells, and transmits a signal that results in a decrease in tumor-infiltrating lymphocytes and a decrease in T cell proliferation. An "inhibitor" of signaling refers to a compound or agent that antagonizes or reduces the initiation, reception or transmission of a signal, be that signal stimulatory or inhibitory, by any component of a signaling pathway such as a receptor or its ligand.

A "subject" includes any human or nonhuman animal. The term "nonhuman animal" includes, but is not limited to, vertebrates such as nonhuman primates, sheep, dogs, cats, rabbits, ferrets, rodents such as mice, rats and guinea pigs, avian species such as chickens, amphibians, and reptiles. In preferred embodiments, the subject is a mammal such as a nonhuman primate, sheep, dog, cat, rabbit, ferret or rodent. In more preferred embodiments, the subject is a human. The terms, "subject," "patient" and "individual" are used interchangeably herein.

A "therapeutically effective amount" or "therapeutically effective dosage" of a drug or therapeutic agent, such as an Ab of the invention, is any amount of the drug that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

By way of example, an anti-cancer agent promotes cancer regression in a subject. In preferred embodiments, a therapeutically effective amount of the drug promotes cancer regression to the point of eliminating the cancer. "Promoting cancer regression" means that administering an effective amount of the drug, alone or in combination with an anti-neoplastic agent, results in a reduction in tumor growth or size, necrosis of the tumor, a decrease in severity of at least one disease symptom, an increase in frequency and duration of disease symptom-free periods, or a prevention of impairment or disability due to the disease affliction. In addition, the terms "effective" and "effectiveness" with regard to a treatment includes both pharmacological effectiveness and physiological safety. Pharmacological effectiveness refers to the ability of the drug to promote cancer regression in the patient. Physiological safety refers to the level of toxicity, or other adverse physiological effects at the cellular, organ and/or organism level (adverse effects) resulting from administration of the drug.

By way of example for the treatment of tumors, a therapeutically effective amount of the drug preferably inhibits cell growth or tumor growth by at least about 20%, more preferably by at least about 40%, even more preferably by at least about 60%, and still more preferably by at least about 80% relative to untreated subjects. In other preferred embodiments of the invention, tumor regression may be observed and continue for a period of at least about 20 days, more preferably at least about 40 days, or even more preferably at least about 60 days. Notwithstanding these ultimate measurements of therapeutic effectiveness, evaluation of immunotherapeutic drugs must also make allowance for "immune-related" response patterns.

An "immune-related" response pattern refers to a clinical response pattern often observed in cancer patients treated with immunotherapeutic agents that produce antitumor effects by inducing cancer-specific immune responses or by modifying native immune processes. This response pattern is characterized by a beneficial therapeutic effect that follows an initial increase in tumor burden or the appearance of new lesions, which in the evaluation of traditional chemotherapeutic agents would be classified as disease progression and would be synonymous with drug failure. Accordingly, proper evaluation of immunotherapeutic agents may require long-term monitoring of the effects of these agents on the target disease.

A therapeutically effective amount of a drug includes a "prophylactically effective amount," which is any amount of the drug that, when administered alone or in combination with an anti-neoplastic agent to a subject at risk of developing a cancer (e.g., a subject having a pre-malignant condition) or of suffering a recurrence of cancer, inhibits the development or recurrence of the cancer. In preferred embodiments, the prophylactically effective amount prevents the development or recurrence of the cancer entirely. "Inhibiting" the development or recurrence of a cancer means either lessening the likelihood of the cancer's development or recurrence, or preventing the development or recurrence of the cancer entirely.

A "tumor-infiltrating inflammatory cell" is any type of cell that typically participates in an inflammatory response in a subject and which infiltrates tumor tissue. Such cells include tumor-infiltrating lymphocytes (TILs), macrophages, monocytes, eosinophils, histiocytes and dendritic cells.

The use of the alternative (e.g., "or") should be understood to mean either one, both, or any combination thereof of the alternatives. As used herein, the indefinite articles "a" or "an" should be understood to refer to "one or more" of any recited or enumerated component.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 20%. Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

As described herein, any concentration range, percentage range, ratio range or integer range is to be understood to include the value of any integer within the recited range and, when appropriate, fractions thereof (such as one tenth and one hundredth of an integer), unless otherwise indicated.

Various aspects of the invention are described in further detail in the following subsections.

Antibodies of the Invention

Abs of the present invention include a variety of Abs having structural and functional properties described herein, including high-affinity binding to PD-1 or PD-L1, respectively. These Abs may be used, for example, as therapeutic Abs to treat subjects afflicted with disease or as reagents in diagnostic assays to detect their cognate antigens. Human mAbs (HuMAbs) that bind specifically to PD-1 (e.g., bind to human PD-1 and may cross-react with PD-1 from other species, such as cynomolgus monkey) with high affinity have been disclosed in U.S. Pat. No. 8,008,449, and HuMAbs that bind specifically to PD-L1 with high affinity have been disclosed in U.S. Pat. No. 7,943,743. The Abs of the invention include, but are not limited to, all of the anti-PD-1 and anti-PD-L1 Abs disclosed in U.S. Pat. Nos. 8,008,449 and 7,943,743, respectively. Other anti-PD-1 mAbs have been described in, for example, U.S. Pat. Nos. 7,488,802 and 8,168,757, and anti-PD-L1 mAbs have been described in, for example, U.S. Pat. Nos. 7,635,757 and 8,217,149, and U.S. Publication No. 2009/0317368. To the extent these anti-PD-1 and anti-PD-L1 mAbs exhibit the structural and functional properties disclosed herein for antibodies of the invention, they too are included as antibodies of the invention.

Anti-PD-1 Antibodies of the Invention

Each of the anti-PD-1 HuMAbs disclosed in U.S. Pat. No. 8,008,449 has been demonstrated to exhibit one or more of the following characteristics: (a) binds to human PD-1 with a $K_D$ of $1 \times 10^{-7}$ M or less, as determined by surface plasmon resonance using a BIACORE® biosensor system; (b) does not substantially bind to human CD28, CTLA-4 or ICOS; (c) increases T-cell proliferation in a Mixed Lymphocyte Reaction (MLR) assay; (d) increases interferon-γ production in an MLR assay; (e) increases IL-2 secretion in an MLR assay; (f) binds to human PD-1 and cynomolgus monkey PD-1; (g) inhibits the binding of PD-L1 and/or PD-L2 to PD-1; (h) stimulates antigen-specific memory responses; (i) stimulates Ab responses; and (j) inhibits tumor cell growth in vivo. Anti-PD-1 Abs of the present invention include mAbs that bind specifically to human PD-1 and exhibit at least one, preferably at least five, of the preceding characteristics.

U.S. Pat. No. 8,008,449 exemplifies seven anti-PD-1 HuMAbs: 17D8, 2D3, 4H1, 5C4 (also referred to herein as nivolumab or BMS-936558), 4A11, 7D3 and 5F4. Isolated DNA molecules encoding the heavy and light chain variable regions of these Abs have been sequenced, from which the amino acid sequences of the variable regions were deduced. The $V_H$ amino acid sequences of 17D8, 2D3, 4H1, 5C4, 4A11, 7D3 and 5F4 are provided herein as SEQ ID NOs. 1, 2, 3, 4, 5, 6 and 7, respectively. The $V_L$ amino acid sequences of 17D8, 2D3, 4H1, 5C4, 4A11, 7D3 and 5F4 are provided herein as SEQ ID NOs. 8, 9, 10, 11, 12, 13 and 14, respectively.

Preferred anti-PD-1 Abs of the present invention include the anti-PD-1 HuMAbs 17D8, 2D3, 4H1, 5C4, 4A11, 7D3 and 5F4. These preferred Abs bind specifically to human PD-1 and comprise: (a) a human heavy chain variable region comprising consecutively linked amino acids having the sequence set forth in SEQ ID NO: 1 and a human light chain variable region comprising consecutively linked amino acids having the sequence set forth in SEQ ID NO: 8; (b) a human heavy chain variable region comprising consecutively linked amino acids having the sequence set forth in SEQ ID NO: 2 and a human light chain variable region comprising consecutively linked amino acids having the sequence set forth in SEQ ID NO: 9; (c) a human heavy chain variable region comprising consecutively linked amino acids having the sequence set forth in SEQ ID NO: 3 and a human light chain variable region comprising consecutively linked amino acids having the sequence set forth in SEQ ID NO: 10; (d) a human heavy chain variable region comprising consecutively linked amino acids having the sequence set forth in SEQ ID NO: 4 and a human light chain variable region comprising consecutively linked amino acids having the sequence set forth in SEQ ID NO: 11; (e) a human heavy chain variable region comprising consecutively linked amino acids having the sequence set forth in SEQ ID NO: 5 and a human light chain variable region comprising consecutively linked amino acids having the sequence set forth in SEQ ID NO: 12; (f) a human heavy chain variable region comprising consecutively linked amino acids having the sequence set forth in SEQ ID NO: 6 and a human light chain variable region comprising consecutively linked amino acids having the sequence set forth in SEQ ID NO: 13; or (g) a human heavy chain variable region comprising consecutively linked amino acids having the sequence set forth in SEQ ID NO: 7 and a human light chain variable region comprising consecutively linked amino acids having the sequence set forth in SEQ ID NO: 14.

Given that each of these Abs can bind to PD-1, the $V_H$ and $V_L$ sequences can be "mixed and matched" to create other anti-PD-1 Abs of the invention. PD-1 binding of such "mixed and matched" Abs can be tested using binding assays, e.g., enzyme-linked immunosorbent assays (ELISAs), western blots, radioimmunoassays and BIACORE® analysis that are well known in the art (see, e.g., U.S. Pat. No. 8,008,449). Preferably, when $V_H$ and $V_L$ chains are mixed and matched, a $V_H$ sequence from a particular $V_H N_L$ pairing is replaced with a structurally similar $V_H$ sequence. Likewise, preferably a $V_L$ sequence from a particular $V_H N_L$ pairing is replaced with a structurally similar $V_L$ sequence. Accordingly, anti-PD-1 Abs of the invention include an isolated mAb or antigen-binding portion thereof comprising: (a) a heavy chain variable region comprising an amino acid sequence selected from the group consisting of SEQ ID NOs. 1, 2, 3, 4, 5, 6 and 7, and (b) a light chain variable region comprising an amino acid sequence selected from the group consisting of SEQ ID NOs. 8, 9, 10, 11, 12, 13 and 14, wherein the Ab specifically binds PD-1, preferably human PD-1.

The CDR domains of the above Abs have been delineated using the Kabat system, and these Abs may also be defined by combinations of their 3 heavy chain and 3 light chain CDRs (see U.S. Pat. No. 8,008,449). Since each of these Abs can bind to PD-1 and antigen-binding specificity is provided primarily by the CDR1, CDR2, and CDR3 regions, the $V_H$ CDR1, CDR2, and CDR3 sequences and $V_\kappa$ CDR1, CDR2, and CDR3 sequences can be "mixed and matched" (i.e., CDRs from different Abs can be mixed and match, although each Ab must contain a $V_H$ CDR1, CDR2, and CDR3 and a $V_\kappa$ CDR1, CDR2, and CDR3) to create other anti-PD-1 Abs that also constitute Abs of the invention. PD-1 binding of such "mixed and matched" Abs can be tested using the binding assays described above (e.g., ELISAs, western blots, radioimmunoassays and BIACORE® analysis).

Abs of the invention also include isolated Abs that bind specifically to PD-1 and comprise a heavy chain variable region derived from a particular germline heavy chain immunoglobulin and/or a light chain variable region derived from a particular germline light chain immunoglobulin. Specifically, in certain embodiments, Abs of the invention include isolated Abs comprising: (a) a heavy chain variable region that comprises consecutively linked amino acids having a sequence derived from a human $V_H$ 3-33 or 4-39 germline sequence, and/or a light chain variable region that comprises consecutively linked amino acids having a sequence derived from a human $V_\kappa$ L6, or L15 germline sequence. The amino acid sequences of the $V_H$ and $V_\kappa$ regions encoded by the $V_H$ 3-33, $V_H$ 4-39, $V_\kappa$ L6 and $V_\kappa$ L15 germline genes are provided in U.S. Pat. No. 8,008,449.

As used herein, an Ab can be identified as comprising a heavy or a light chain variable region that is "derived from" a particular human germline immunoglobulin by comparing the amino acid sequence of the human Ab to the amino acid sequences encoded by human germline immunoglobulin genes, and selecting the human germline immunoglobulin sequence that is closest in sequence (i.e., greatest percentage of sequence identity) to the sequence of the human Ab. A human Ab that is "derived from" a particular human germline immunoglobulin may contain amino acid differences as compared to the germline sequence, due to, for example, naturally-occurring somatic mutations or intentional introduction of site-directed mutation. However, a selected human Ab is generally at least 90% identical in amino acids sequence to an amino acid sequence encoded by a human germline immunoglobulin gene and contains amino acid residues that identify the human Ab as being human when compared to the germline immunoglobulin amino acid sequences of other species (e.g., murine germline sequences). In certain cases, a human Ab may be at least 95%, or even at least 96%, 97%, 98%, or 99% identical in amino acid sequence to the amino acid sequence encoded by the germline immunoglobulin gene.

In certain embodiments, the sequence of a human Ab derived from a particular human germline sequence will display no more than 10 amino acid differences from the amino acid sequence encoded by the human germline immunoglobulin gene. In other embodiments, the human Ab may display no more than 5, or even no more than 4, 3, 2, or 1 amino acid differences from the amino acid sequence encoded by the germline immunoglobulin gene.

Preferred Abs of the invention also include isolated Abs or antigen-binding portions thereof comprising: (a) a heavy chain variable region that comprises consecutively linked amino acids having a sequence derived from a human $V_H$ 3-33 germline sequence, and a light chain variable region that comprises consecutively linked amino acids having a sequence derived from a human $V_\kappa$ L6 germline sequence; or (b) a heavy chain variable region that comprises consecutively linked amino acids having a sequence derived from a human $V_H$ 4-39 germline sequence, and a light chain variable region that comprises consecutively linked amino acids having a sequence derived from a human $V_\kappa$ L15 germline sequence. Examples of Abs having a $V_H$ and a $V_\kappa$ derived from $V_H$ 3-33 and $V_\kappa$ L6 germline sequences, respectively, include 17D8, 2D3, 4H1, 5C4, and 7D3. Examples of Abs having $V_H$ and $V_\kappa$ regions derived from $V_H$ 4-39 and $V_\kappa$ L15 germline sequences, respectively, include 4A11 and 5F4.

In yet other embodiments, anti-PD-1 Abs of the invention comprise heavy and light chain variable regions having amino acid sequences that are highly similar or homologous to the amino acid sequences of the preferred anti-PD-1 Abs described herein, wherein the Ab retains the functional properties of the preferred anti-PD-1 Abs of the invention. For example, Abs of the invention include mAbs comprising a heavy chain variable region and a light chain variable region, wherein the heavy chain variable region comprises consecutively linked amino acids having a sequence that is at least 80% identical to an amino acid sequence selected from the group consisting of SEQ ID NOs. 1, 2, 3, 4, 5, 6 and 7, and the light chain variable region comprises consecutively linked amino acids having a sequence that is at least 80% identical to an amino acid sequence selected from the group consisting of SEQ ID NOs. 8, 9, 10, 11, 12, 13 and 14. In other embodiments, the $V_H$ and/or $V_L$ amino acid sequences may exhibit at least 85%, 90%, 95%, 96%, 97%, 98% or 99% identity to the sequences set forth above.

As used herein, the percent sequence identity (also referred to as the percent sequence homology) between two sequences (amino acid or nucleotide sequences) is a function of the number of identical positions shared by the sequences relative to the length of the sequences compared (i.e., % identity=number of identical positions/total number of positions being compared×100), taking into account the number of any gaps, and the length of each such gap, introduced to maximize the degree of sequence identity between the two sequences. The comparison of sequences and determination of percent identity between two sequences can be accomplished using mathematical algorithms that are well know to those of ordinary skill in the art (see, e.g., U.S. Pat. No. 8,008,449).

Antibodies having very similar amino acid sequences are likely to have essentially the same functional properties where the sequence differences are conservative modifications. As used herein, "conservative sequence modifications" refer to amino acid modifications that do not significantly affect the binding characteristics of the Ab containing the amino acid sequence. Such conservative modifications include amino acid substitutions, additions and deletions. Conservative amino acid substitutions are substitutions in which the amino acid residue is replaced with an amino acid residue having a similar side chain. Thus, for example, one or more amino acid residues within the CDR regions of an Ab of the invention can be replaced with other amino acid residues from the same side chain family and the altered Ab can be tested for retained function using functional assays that are well known in the art. Accordingly, certain embodiments of the anti-PD-1 Abs of the invention comprise heavy and light chain variable regions each comprising CDR1, CDR2 and CDR3 domains, wherein one or more of these CDR domains comprise consecutively linked amino acids having sequences that are the same as the CDR sequences of the preferred anti-PD-1 Abs described herein (e.g., 17D8, 2D3, 4H1, 5C4, 4A11, 7D3 or 5F4), or conservative modifications thereof, and wherein the Abs retain the desired functional properties of the preferred anti-PD-1 Abs of the invention.

Further, it is well known in the art that the heavy chain CDR3 is the primary determinant of binding specificity and affinity of an Ab, and that multiple Abs can predictably be generated having the same binding characteristics based on a common CDR3 sequence (see, e.g., Klimka et al., 2000; Beiboer et al., 2000; Rader et al., 1998; Barbas et al., 1994; Barbas et al., 1995; Ditzel et al., 1996; Berezov et al., 2001; Igarashi et al., 1995; Bourgeois et al., 1998; Levi et al., 1993; Polymenis et al., 1994; and Xu et al., 2000). The foregoing publications demonstrate that, in general, once the heavy chain CDR3 sequence of a given Ab is defined, variability in the other five CDR sequences will not greatly affect the binding specificity of that Ab. Thus, Abs of the invention comprising 6 CDRs can be defined by specifying the sequence of the heavy chain CDR3 domain.

Anti-PD-1 Abs of the invention also include isolated Abs that bind specifically to human PD-1 and cross-compete for binding to human PD-1 with any of HuMAbs 17D8, 2D3, 4H1, 5C4, 4A11, 7D3 and 5F4. Thus, anti-PD-1 Abs of the invention include isolated Abs or antigen-binding portions thereof that cross-compete for binding to PD-1 with a reference Ab or a reference antigen-binding portion thereof comprising: (a) a human heavy chain variable region comprising consecutively linked amino acids having the sequence set forth in SEQ ID NO: 1 and a human light chain variable region comprising consecutively linked amino acids having the sequence set forth in SEQ ID NO: 8; (b) a human heavy chain variable region comprising consecutively linked amino acids having the sequence set forth in SEQ ID NO: 2 and a human light chain variable region comprising consecutively linked amino acids having the sequence set forth in SEQ ID NO: 9; (c) a human heavy chain variable region comprising consecutively linked amino acids having the sequence set forth in SEQ ID NO: 3 and a human light chain variable region comprising consecutively linked amino acids having the sequence set forth in SEQ ID NO: 10; (d) a human heavy chain variable region comprising consecutively linked amino acids having the sequence set forth in SEQ ID NO: 4 and a human light chain variable region comprising consecutively linked amino acids having the sequence set forth in SEQ ID NO: 11; (e) a human heavy chain variable region comprising consecutively linked amino acids having the sequence set forth in SEQ ID NO: 5 and a human light chain variable region comprising consecutively linked amino acids having the sequence set forth in SEQ ID NO: 12; (f) a human heavy chain variable region comprising consecutively linked amino acids having the sequence set forth in SEQ ID NO: 6 and a human light chain variable region comprising consecutively linked amino acids having the sequence set forth in SEQ ID NO: 13; or (g) a human heavy chain variable region comprising consecutively linked amino acids having the sequence set forth in SEQ ID NO: 7 and a human light chain variable region comprising consecutively linked amino acids having the sequence set forth in SEQ ID NO: 14.

Figure 1B:
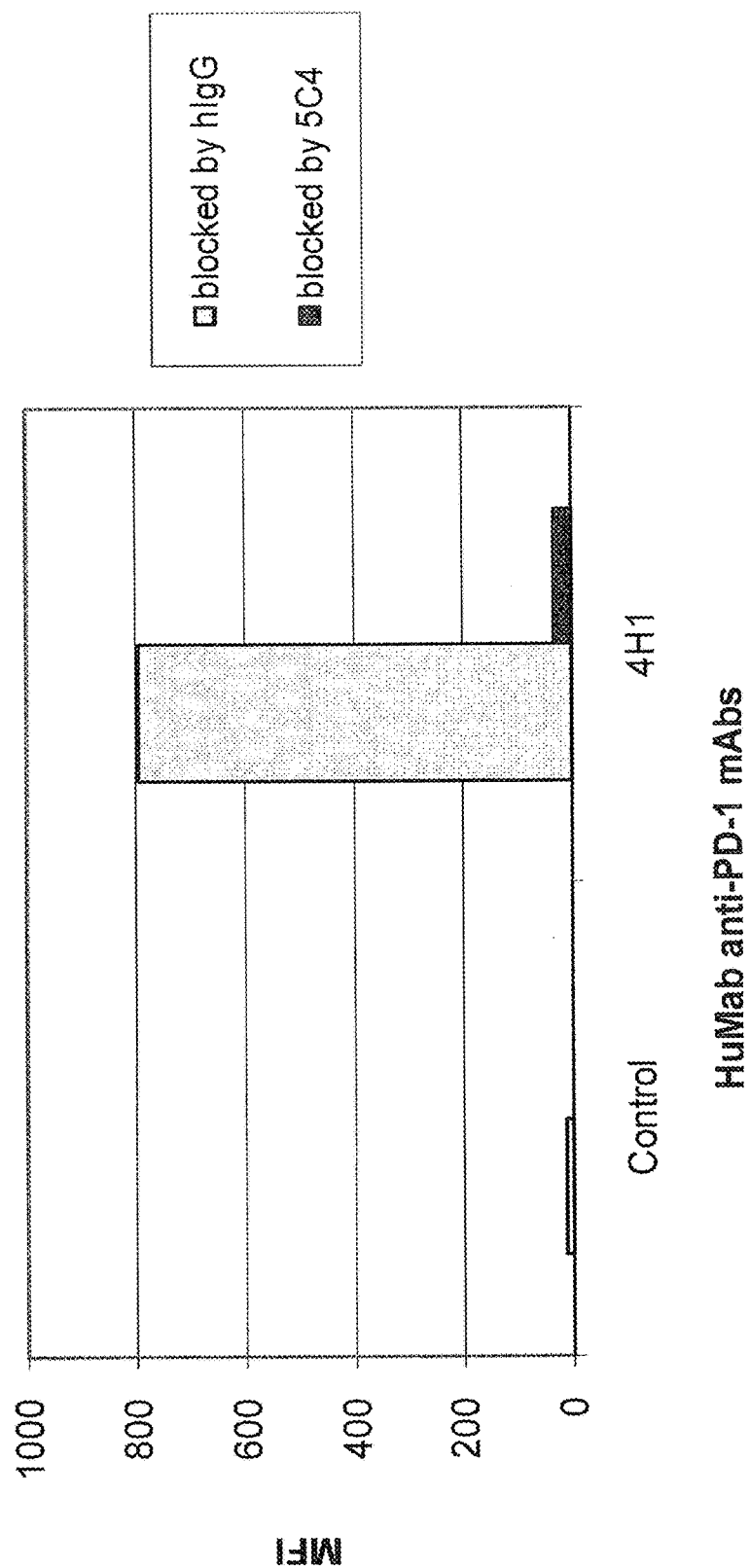
Figure 1C:
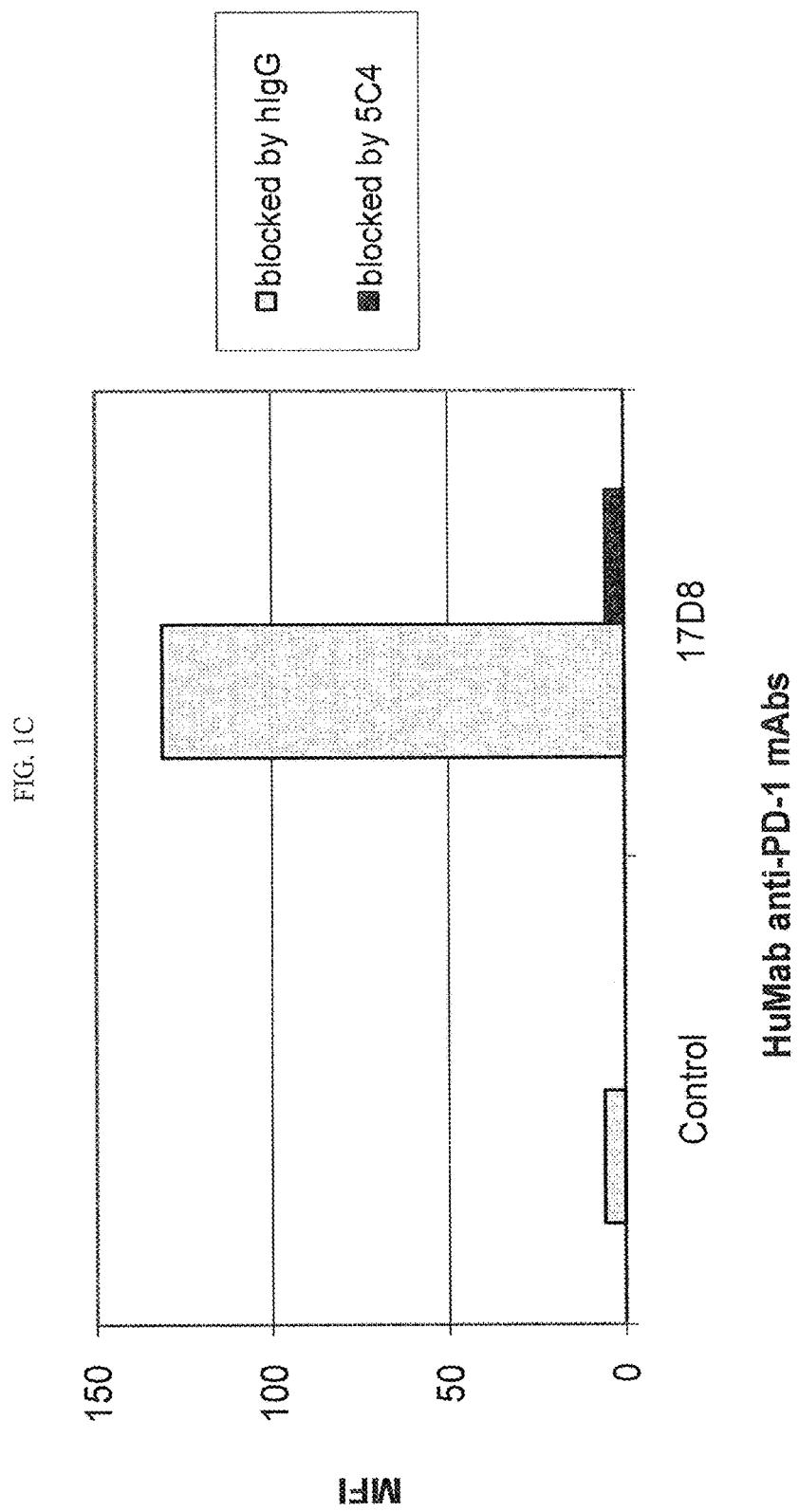

The ability of Abs to cross-compete for binding to an antigen indicates that these Abs bind to the same epitope region (i.e., the same or an overlapping epitope) of the antigen and sterically hinder the binding of other cross-competing Abs to that particular epitope region. Thus, the ability of a test Ab to competitively inhibit the binding of, for example, 17D8, 2D3, 4H1, 5C4, 4A11, 7D3 or 5F4, to human PD-1 demonstrates that the test Ab binds to the same epitope region of human PD-1 as 17D8, 2D3, 4H1, 5C4, 4A11, 7D3 or 5F4, respectively. All isolated Abs that bind to the same epitope region of human PD-1 as does HuMAb 17D8, 2D3, 4H1, 5C4, 4A11, 7D3 or 5F4 are included among the Abs of the invention. These cross-competing Abs are expected to have very similar functional properties by virtue of their binding to the same epitope region of PD-1. For example, cross-competing anti-PD-1 mAbs 5C4, 2D3, 7D3, 4H1 and 17D8 have been shown to have similar functional properties (see U.S. Pat. No. 8,008,449 at Examples 3-7). The higher the degree of cross-competition, the more similar will the functional properties be. Further, cross-competing Abs can be readily identified based on their ability to cross-compete with 17D8, 2D3, 4H1, 5C4, 4A11, 7D3 or 5F4 in standard PD-1 binding assays. For example, BIACORE® analysis, ELISA assays or flow cytometry may be used to demonstrate cross-competition with the Abs of the invention (see, e.g., Examples 1 and 2). In preferred embodiments, the Abs that cross-compete for binding to human PD-1 with, or bind to the same epitope region of human PD-1 as, 17D8, 2D3, 4H1, 5C4, 4A11, 7D3 or 5F4 are mAbs, preferably chimeric Abs, or more preferably humanized or human Abs. Such human mAbs can be prepared and isolated as described in U.S. Pat. No. 8,008,449. Data provided in Example 1 show that 5C4 or a Fab fragment thereof cross-competes with each of 2D3, 7D3, 4H1 or 17D8 for binding to hPD-1 expressed on the surface of a cell, indicating that all five anti-PD-1 mAbs bind to the same epitope region of hPD-1 (FIGS. 1A-1C).

An anti-PD-1 Ab of the invention further can be prepared using an Ab having one or more of the $V_H$ and/or $V_L$ sequences disclosed herein as starting material to engineer a modified Ab, which modified Ab may have altered properties from the starting Ab. An Ab can be engineered by modifying one or more residues within one or both variable regions (i.e., $V_H$ and/or $V_L$), for example within one or more CDR regions and/or within one or more framework regions. Additionally or alternatively, an Ab can be engineered by modifying residues within the constant region(s), for example, to alter the effector function(s) of the Ab. Specific modifications to Abs include CDR grafting, site-specific mutation of amino acid residues within the $V_H$ and/or $V_\kappa$ CDR1, CDR2 and/or CDR3 regions to thereby improve one or more binding properties (e.g., affinity) of the Ab, site-specific mutation of amino acid residues within the $V_H$ and/or $V_\kappa$ framework regions to decrease the immunogenicity of the Ab, modifications within the Fc region, typically to alter one or more functional properties of the Ab, such as serum half-life, complement fixation, Fc receptor binding, and/or antigen-dependent cellular cytotoxicity, and chemical modification such as pegylation or alteration in glycosylation patterns to increase or decrease the biological (e.g., serum) half life of the Ab. Specific examples of such modifications and methods of engineering Abs are described in detail in U.S. Pat. No. 8,008,449. Anti-PD-1 Abs of the invention include all such engineered Abs that bind specifically to human PD-1 and are obtained by modification of any of the above-described anti-PD-1 Abs.

Anti-PD-1 Abs of the invention also include antigen-binding portions of the above Abs. It has been amply demonstrated that the antigen-binding function of an Ab can be performed by fragments of a full-length Ab. Examples of binding fragments encompassed within the term "antigen-binding portion" of an Ab include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; and (iv) a Fv fragment consisting of the $V_L$ and $V_H$ domains of a single arm of an Ab.

These fragments, obtained initially through proteolysis with enzymes such as papain and pepsin, have been subsequently engineered into monovalent and multivalent antigen-binding fragments. For example, although the two domains of the Fv fragment, $V_L$ and $V_H$, are coded for by separate genes, they can be joined, using recombinant methods, by a synthetic linker peptide that enables them to be made as a single protein chain in which the $V_L$ and $V_H$ regions pair to form monovalent molecules known as single chain variable fragments (scFv). Divalent or bivalent scFvs (di-scFvs or bi-scFvs) can be engineered by linking two scFvs in within a single peptide chain known as a tandem scFv which contains two $V_H$ and two $V_L$ regions. ScFv dimers and higher multimers can also be created using linker peptides of fewer than 10 amino acids that are too short for the two variable regions to fold together, which forces the scFvs to dimerize and produce diabodies or form other multimers. Diabodies have been shown to bind to their cognate antigen with much higher affinity than the corresponding scFvs, having dissociation constants up to 40-fold lower than the $K_D$ values for the scFvs. Very short linkers (≤3 amino acids) lead to the formation of trivalent triabodies or tetravalent tetrabodies that exhibit even higher affinities for to their antigens than diabodies. Other variants include minibodies, which are scFv-$C_{H3}$ dimers, and larger scFv-Fc fragments (scFv-$C_{H2}$-$C_{H3}$ dimers), and even an isolated CDR may exhibit antigen-binding function. These Ab fragments are engineered using conventional recombinant techniques known to those of skill in the art, and the fragments are screened for utility in the same manner as are intact Abs. All of the above proteolytic and engineered fragments of Abs and related variants (see Hollinger et al., 2005; Olafsen et al., 2010, for further details) are intended to be encompassed within the term "antigen-binding portion" of an Ab.

Anti-PD-L1 Antibodies of the Invention

Each of the anti-PD-L1 HuMAbs disclosed in U.S. Pat. No. 7,943,743 has been demonstrated to exhibit one or more of the following characteristics (a) binds to human PD-L1 with a $K_D$ of $1 \times 10^{-7}$ M or less; (b) increases T-cell proliferation in a Mixed Lymphocyte Reaction (MLR) assay; (c) increase interferon-γ production in an MLR assay; (d) increase IL-2 secretion in an MLR assay; (e) stimulates Ab responses; (f) inhibits the binding of PD-L1 to PD-1; and (g) reverses the suppressive effect of T regulatory cells on T cell effector cells and/or dendritic cells. Anti-PD-L1 Abs of the present invention include mAbs that bind specifically to human PD-L1 and exhibit at least one, preferably at least four, of the preceding characteristics.

U.S. Pat. No. 7,943,743 exemplifies ten anti-PD-1 HuMAbs: 3G10, 12A4 (also referred to herein as BMS-936559), 10A5, 5F8, 10H10, 1B12, 7H1, 11E6, 12B7, and 13G4. Isolated DNA molecules encoding the heavy and light chain variable regions of these Abs have been sequenced, from which the amino acid sequences of the variable regions were deduced. The $V_H$ amino acid sequences of 3G10, 12A4, 10A5, 5F8, 10H10, 1B12, 7H1, 11E6, 12B7, and 13G4 are shown in SEQ ID NOs. 15, 16, 17, 18, 19, 20, 21, 22, 23 and 24, respectively, whereas their $V_L$ amino acid sequences are shown in SEQ ID NOs. 25, 26, 27, 28, 29, 30, 31, 32, 33 and 34, respectively.

Preferred anti-PD-L1 Abs of the present invention include the anti-PD-L1 HuMAbs 3G10, 12A4, 10A5, 5F8, 10H10, 1B12, 7H1, 11E6, 12B7, and 13G4. These preferred Abs bind specifically to human PD-L1 and comprise: (a) a human heavy chain variable region comprising consecutively linked amino acids having the sequence set forth in SEQ ID NO: 15 and a human light chain variable region comprising consecutively linked amino acids having the sequence set forth in SEQ ID NO: 25; (b) a human heavy chain variable region comprising consecutively linked amino acids having the sequence set forth in SEQ ID NO: 16 and a human light chain variable region comprising consecutively linked amino acids having the sequence set forth in SEQ ID NO: 26; (c) a human heavy chain variable region comprising consecutively linked amino acids having the sequence set forth in SEQ ID NO: 17 and a human light chain variable region comprising consecutively linked amino acids having the sequence set forth in SEQ ID NO: 27; (d) a human heavy chain variable region comprising consecutively linked amino acids having the sequence set forth in SEQ ID NO: 18 and a human light chain variable region comprising consecutively linked amino acids having the sequence set forth in SEQ ID NO: 28; (e) a human heavy chain variable region comprising consecutively linked amino acids having the sequence set forth in SEQ ID NO: 19 and a human light chain variable region comprising consecutively linked amino acids having the sequence set forth in SEQ ID NO: 29; (f) a human heavy chain variable region comprising consecutively linked amino acids having the sequence set forth in SEQ ID NO: 20 and a human light chain variable region comprising consecutively linked amino acids having the sequence set forth in SEQ ID NO: 30; (g) a human heavy chain variable region comprising consecutively linked amino acids having the sequence set forth in SEQ ID NO: 21 and a human light chain variable region comprising consecutively linked amino acids having the sequence set forth in SEQ ID NO: 31; (h) a human heavy chain variable region comprising consecutively linked amino acids having the sequence set forth in SEQ ID NO: 22 and a human light chain variable region comprising consecutively linked amino acids having the sequence set forth in SEQ ID NO: 32; (i) a human heavy chain variable region comprising consecutively linked amino acids having the sequence set forth in SEQ ID NO: 23 and a human light chain variable region comprising consecutively linked amino acids having the sequence set forth in SEO ID NO: 33; or (j) a human heavy chain variable region comprising consecutively linked amino acids having the sequence set forth in SEQ ID NO: 24 and a human light chain variable region comprising consecutively linked amino acids having the sequence set forth in SEQ ID NO: 34.

Given that each of these Abs can bind to PD-L1, the $V_H$ and $V_L$ sequences can be "mixed and matched" to create other anti-PD-L1 Abs of the invention. PD-L1 binding of such "mixed and matched" Abs can be tested using binding assays e.g., ELISAs, western blots, radioimmunoassays and BIACORE® analysis that are well known in the art (see, e.g., U.S. Pat. No. 7,943,743). Preferably, when $V_H$ and $V_L$ chains are mixed and matched, a $V_H$ sequence from a particular $V_H/V_L$ pairing is replaced with a structurally similar $V_H$ sequence. Likewise, preferably a $V_L$ sequence from a particular $V_H/V_L$ pairing is replaced with a structurally similar $V_L$ sequence. Accordingly, Abs of the invention also include a mAb, or antigen binding portion thereof, comprising a heavy chain variable region comprising consecutively linked amino acids having the sequence set forth in any of SEQ ID NOs. 15, 16, 17, 18, 19, 20, 21, 22, 23 or 24, and a light chain variable region comprising consecutively linked amino acids having the sequence set forth in any of SEQ ID NOs. 25, 26, 27, 28, 29, 30, 31, 32, 33 or 34, wherein the Ab binds specifically to PD-L1, preferably human PD-L1.

The CDR domains of the above anti-PD-L1 HuMAbs have been delineated using the Kabat system, and these Abs may also be defined by combinations of their 3 heavy chain and 3 light chain CDRs (see U.S. Pat. No. 7,943,743). Since each of these Abs can bind to PD-L1 and antigen-binding specificity is provided primarily by the CDR1, CDR2, and CDR3 regions, the $V_H$ CDR1, CDR2, and CDR3 sequences and $V_\kappa$ CDR1, CDR2, and CDR3 sequences can be "mixed and matched" (i.e., CDRs from different Abs can be mixed and match, although each Ab must contain a $V_H$ CDR1, CDR2, and CDR3 and a $V_\kappa$ CDR1, CDR2, and CDR3) to create other anti-PD-1 Abs that also constitute Abs of the invention. PD-L1 binding of such "mixed and matched" Abs can be tested using, for example, ELISAs, western blots, radioimmunoassays and BIACORE® analysis.

Antibodies of the invention also include Abs that bind specifically to PD-L1 and comprise a heavy chain variable region derived from a particular germline heavy chain immunoglobulin and/or a light chain variable region derived from a particular germline light chain immunoglobulin. Specifically, in certain embodiments, Abs of the invention include Abs comprising: (a) a heavy chain variable region that comprises consecutively linked amino acids having a sequence derived from a human $V_H$ 1-18, 1-69, 1-3 or 3-9 germline sequence, and/or a light chain variable region that comprises consecutively linked amino acids having a sequence derived from a human $V_\kappa$ L6, L15, A27 or L18 germline sequence. The amino acid sequences of the $V_H$ and $V_\kappa$ regions encoded by the $V_H$ 1-18, $V_H$ 1-3, $V_H$ 1-69, $V_H$ 3-9, $V_\kappa$ L6, $V_\kappa$ L15 and $V_\kappa$ A27 germline genes are provided in U.S. Pat. No. 7,943,743.

Preferred Abs of the invention include isolated Abs or antigen-binding portions thereof comprising: (a) a heavy chain variable region that comprises consecutively linked amino acids having a sequence derived from a human $V_H$ 1-18 germline sequence, and a light chain variable region that comprises consecutively linked amino acids having a sequence derived from a human $V_\kappa$ L6 germline sequence; (b) a heavy chain variable region that comprises consecutively linked amino acids having a sequence derived from a human $V_H$ 1-69 germline sequence, and a light chain variable region that comprises consecutively linked amino acids having a sequence derived from a human $V_\kappa$ L6 germline sequence; (c) a heavy chain variable region that comprises consecutively linked amino acids having a sequence derived from a human $V_H$ 1-3 germline sequence, and a light chain variable region that comprises consecutively linked amino acids having a sequence derived from a human $V_\kappa$ L15 germline sequence; (d) a heavy chain variable region that comprises consecutively linked amino acids having a sequence derived from a human $V_H$ 1-69 germline sequence, and a light chain variable region that comprises consecutively linked amino acids having a sequence derived from a human $V_\kappa$ A27 germline sequence; (e) a heavy chain variable region that comprises consecutively linked amino acids having a sequence derived from a human $V_H$ 3-9 germline sequence, and a light chain variable region that comprises consecutively linked amino acids having a sequence derived from a human $V_\kappa$ L15germline sequence; or (f) a heavy chain variable region that comprises consecutively linked amino acids having a sequence derived from a human $V_H$ 3-9 germline sequence, and a light chain variable region that comprises consecutively linked amino acids having a sequence derived from a human $V_\kappa$ L18germline sequence.

An example of an Ab having a $V_H$ and a $V_\kappa$ derived from $V_H$ 1-18 and $V_\kappa$ L6 germline sequences, respectively, is 3G10. Examples of Abs having $V_H$ and $V_\kappa$ regions derived from $V_H$ 1-69 and $V_\kappa$ L6 germline sequences, respectively, include 12A4, 1B12, 7H1 and 12B7. An example of an Ab having a $V_H$ and a $V_\kappa$ derived from $V_H$ 1-3 and $V_\kappa$ L15 germline sequences, respectively, is 10A5. Examples of Abs having $V_H$ and $V_\kappa$ regions derived from $V_H$ 1-69 and $V_\kappa$ A27 germline sequences, respectively, include 5F8, 11E6 and 11E6a. An example of an Ab having a $V_H$ and a $V_K$ derived from $V_H$ 3-9 and $V_\kappa$ L15 germline sequences, respectively, is 10H10. An example of an Ab having a $V_H$ and a $V_\kappa$ derived from $V_H$ 1-3 and $V_\kappa$ L15 germline sequences, respectively, is 10A5. An example of an Ab having a $V_H$ and a $V_\kappa$ derived from $V_H$ 3-9 and $V_\kappa$ L18 germline sequences, respectively, is 13G4.

In certain embodiments, anti-PD-L1 Abs of the invention comprise heavy and light chain variable regions having amino acid sequences that are highly similar or homologous to the amino acid sequences of the preferred anti-PD-L1 Abs described herein, wherein the Ab retains the functional properties of the aforementioned anti-PD-L1 Abs of the invention. For example, Abs of the invention include mAbs comprising a heavy chain variable region and a light chain variable region, wherein the heavy chain variable region comprises consecutively linked amino acids having a sequence that is at least 80% identical to an amino acid sequence selected from the group consisting of SEQ ID NOs. 15, 16, 17, 18, 19, 20, 21, 22, 23, and 24, and the light chain variable region comprises consecutively linked amino acids having a sequence that is at least 80% identical to an amino acid sequence selected from the group consisting of SEQ ID NOs. 25, 26, 27, 28, 29, 30, 31, 32, 33, and 34. In other embodiments, the $V_H$ and/or $V_L$ amino acid sequences may exhibit at least 85%, 90%, 95%, 96%, 97%, 98% or 99% identity to the sequences set forth above.

Certain embodiments of the anti-PD-L1 Abs of the invention comprise heavy and light chain variable regions each comprising CDR1, CDR2 and CDR3 domains, wherein one or more of these CDR domains comprise consecutively linked amino acids having sequences that are the same as the CDR sequences of the preferred anti-PD-L1 Abs described herein (e.g., 3G10, 12A4, 10A5, 5F8, 10H10, 1B12, 7H1, 11E6, 12B7 and 13G4), or conservative modifications thereof, and wherein the Abs retain the desired functional properties of the preferred anti-PD-L1 Abs of the invention.

On the basis of the evidence that the heavy chain CDR3 is the primary determinant of binding specificity and affinity of an Ab, it is generally true that once the heavy chain CDR3 sequence of a given Ab is defined, variability in the other five CDR sequences does not greatly affect the binding specificity of that Ab. Accordingly, anti-PD-L1 Abs of the invention include isolated Abs comprising 6 CDRs, wherein the Abs are defined by specifying the sequence of the heavy chain CDR3 domain.

Anti-PD-L1 Abs of the invention also include isolated Abs that bind specifically to human PD-L1 and cross-compete for binding to human PD-L1 with any of HuMAbs 3G10, 12A4, 10A5, 5F8, 10H10, 1B12, 7H1, 11E6, 12B7 and 13G4. Thus, anti-PD-L1 Abs of the invention include isolated Abs or antigen-binding portions thereof that cross-compete for binding to PD-L1 with a reference Ab or a reference antigen-binding portion thereof comprising: (a) a human heavy chain variable region comprising consecutively linked amino acids having the sequence set forth in SEQ ID NO: 15 and a human light chain variable region comprising consecutively linked amino acids having the sequence set forth in SEQ ID NO: 25; (b) a human heavy chain variable region comprising consecutively linked amino acids having the sequence set forth in SEQ ID NO: 16 and a human light chain variable region comprising consecutively linked amino acids having the sequence set forth in SEQ ID NO: 26; (c) a human heavy chain variable region comprising consecutively linked amino acids having the sequence set forth in SEQ ID NO: 17 and a human light chain variable region comprising consecutively linked amino acids having the sequence set forth in SEQ ID NO: 27; (d) a human heavy chain variable region comprising consecutively linked amino acids having the sequence set forth in SEQ ID NO: 18 and a human light chain variable region comprising consecutively linked amino acids having the sequence set forth in SEQ ID NO: 28; (e) a human heavy chain variable region comprising consecutively linked amino acids having the sequence set forth in SEQ ID NO: 19 and a human light chain variable region comprising consecutively linked amino acids having the sequence set forth in SEQ ID NO: 29; (f) a human heavy chain variable region comprising consecutively linked amino acids having the sequence set forth in SEQ ID NO: 20 and a human light chain variable region comprising consecutively linked amino acids having the sequence set forth in SEQ ID NO: 30; (g) a human heavy chain variable region comprising consecutively linked amino acids having the sequence set forth in SEQ ID NO: 21 and a human light chain variable region comprising consecutively linked amino acids having the sequence set forth in SEQ ID NO: 31; (h) a human heavy chain variable region comprising consecutively linked amino acids having the sequence set forth in SEQ ID NO: 22 and a human light chain variable region comprising consecutively linked amino acids having the sequence set forth in SEQ ID NO: 32; (i) a human heavy chain variable region comprising consecutively linked amino acids having the sequence set forth in SEQ ID NO: 23 and a human light chain variable region comprising consecutively linked amino acids having the sequence set forth in SEO ID NO: 33; or (j) a human heavy chain variable region comprising consecutively linked amino acids having the sequence set forth in SEQ ID NO: 24 and a human light chain variable region comprising consecutively linked amino acids having the sequence set forth in SEQ ID NO: 34.

The ability of an Ab to cross-compete with any of 3G10, 12A4, 10A5, 5F8, 10H10, 1B12, 7H1, 11E6, 12B7 and 13G4 for binding to human PD-L1 demonstrates that such Ab binds to the same epitope region of each of 3G10, 12A4, 10A5, 5F8, 10H10, 1B12, 7H1, 11E6, 12B7 and 13G4, respectively. All isolated Abs that bind to the same epitope region of human PD-L1 as does HuMAb 3G10, 12A4, 10A5, 5F8, 10H10, 1B12, 7H1, 11E6, 12B7 or 13G4 are included among the Abs of the invention. These cross-competing Abs are expected to have very similar functional properties by virtue of their binding to the same epitope region of PD-L1. For example, cross-competing anti-PD-L1 mAbs 3G10, 1B12, 13G4, 12A4 (BMS-936559), 10A5, 12B7, 11E6 and 5F8 have been shown to have similar functional properties (see U.S. Pat. No. 7,943,743 at Examples 3-11), whereas mAb 10H10, which binds to a different epitope region, behaves differently (U.S. Pat. No. 7,943,743 at Example 11). The higher the degree of cross-competition, the more similar will the functional properties be. Further, cross-competing Abs can be identified in standard PD-L1 binding assays, e.g., BIACORE® analysis, ELISA assays or flow cytometry, that are well known to persons skilled in the art. In preferred embodiments, the Abs that cross-compete for binding to human PD-1 with, or bind to the same epitope region of human PD-L1 as, 3G10, 12A4, 10A5, 5F8, 10H10, 1B12, 7H1, 11E6, 12B7 or 13G4 are mAbs, preferably chimeric Abs, or more preferably humanized or human Abs. Such human mAbs can be prepared and isolated as described in U.S. Pat. No. 7,943,743.

Data provided in Example 2 show that each of the anti-PD-L1 HuMAbs 5F8, 7H1, 1B12, 3G10, 10A5, 11E6, 12A4, 12B7 and 13G4, i.e., all of the HuMAbs tested except 10H10, substantially blocked binding of mAbs 3G10, 10A5, 11E6, 12A4 and 13G4 to Chinese Hamster Ovary (CHO) cells expressing PD-L1 cells. HuMAb 10H10 substantially blocked the binding only of itself to CHO/PD-L1 cells. These data show that 3G10, 10A5, 11E6, 12A4 and 13G4 cross-compete with all of the HuMAbs tested, except for 10H10, for binding to the same epitope region of human PD-L1 (FIGS. 2A-F).

Data provided in Example 3 show that the binding of HuMAb 12A4 to ES-2 ovarian carcinoma cells expressing PD-L1 cells was substantially blocked by 12A4 itself and by 1B12 and 12B7, and was moderately to significantly blocked by mAbs 5F8, 10A5, 13G4 and 3G10, but was not blocked by mAb 10H10. These data, largely consistent with the data in Example 2, show that 12A4 itself, and 2 other HuMabs, 12B7 and 1B12, substantially cross-compete with 12A4 for binding to the same epitope region, possibly the same epitope, of human PD-L1; 5F8, 10A5, 13G4 and 3G10, exhibit a significant but lower level of cross-competition with 12A4, suggesting that these mAbs may bind to epitopes that overlap the 12A4 epitope; whereas 10H10 does not cross-compete at all with 12A4 (FIG. 3), suggesting that this mAb binds to a different epitope region from 12A4.

Anti-PD-L1 Abs of the invention also include Abs engineered starting from Abs having one or more of the $V_H$ and/or $V_L$ sequences disclosed herein, which engineered Abs may have altered properties from the starting Abs. An anti-PD-L1 Ab can be engineered by a variety of modifications as described above for the engineering of modified anti-PD-1 Abs of the invention.

Anti-PD-L1 Abs of the invention also include isolated Abs selected for their ability to bind to PD-L1 in formalin-fixed, paraffin-embedded (FFPE) tissue specimens. The use of FFPE samples is essential for the long-term follow-up analysis of the correlation between PD-L1 expression in tumors and disease prognosis or progression. Yet, studies on measuring PD-L1 expression have often been conducted on frozen specimens because of the difficulty in isolating anti-human PD-L1 Abs that can be used to stain PD-L1 in FFPE specimens by IHC in general (Hamanishi et al., 2007) and, in particular, Abs that bind specifically to membranous PD-L1 in these tissues. The use of different Abs to stain PD-L1 in frozen versus FFPE tissues, and the ability of certain Abs to distinguish membranous and/or cytoplasmic forms of PD-L1, may account for some of the disparate data reported in the literature correlating PD-L1 expression with disease prognosis (Hamanishi et al., 2007; Gadiot et al., 2011). This disclosure provides several rabbit mAbs that bind with high affinity specifically to membranous human PD-L1 in FFPE tissue samples comprising tumor cells and tumor-infiltrating inflammatory cells.

Rabbit and mouse anti-hPD-L1 mAbs were produced as described in the Examples. Out of almost 200 rabbit Ab multiclones and purified mouse subclones screened, only ten rabbit multiclone Abs were found to specifically detect the membranous form of PD-L1, and the top five multiclones (designated Nos. 13, 20, 28, 29 and 49) were subsequently subcloned. The clone that produced the most robust detection specifically of membranous PD-L1, rabbit clone 28-8, was selected for the IHC assays. The sequences of the variable regions of mAb 28-8 are set forth in SEQ ID NOs. 35 and 36, respectively. Rabbit clones 28-1, 28-12, 29-8 and 20-12 were the next best mAbs in terms of robust detection of membranous PD-L1 in FFPE tissues.

Anti-PD-L1 Abs of the invention also include antigen-binding portions of the above Abs, including Fab, F(ab')$_2$ Fd, Fv, and scFv, di-scFv or bi-scFv, and scFv-Fc fragments, diabodies, triabodies, tetrabodies, and isolated CDRs (see Hollinger et al., 2005; Olafsen et al., 2010, for further details).

Nucleic Acid Molecules Encoding Antibodies of the Invention

Another aspect of the present disclosure pertains to isolated nucleic acid molecules that encode any of the Abs of the invention. These nucleic acids may be present in whole cells, in a cell lysate, or in a partially purified or substantially pure form. A nucleic acid of the invention can be, for example, DNA or RNA, and may or may not contain intronic sequences. In a preferred embodiment, the nucleic acid is a cDNA.

Nucleic acids of the invention can be obtained using standard molecular biology techniques. For Abs expressed by hybridomas (e.g., hybridomas prepared from transgenic mice carrying human immunoglobulin genes as described further below), cDNAs encoding the light and heavy chains of the Ab made by the hybridoma can be obtained by standard PCR amplification or cDNA cloning techniques. Nucleic acids encoding Abs obtained from an immunoglobulin gene library (e.g., using phage display techniques) can be recovered from the library.

Preferred nucleic acids molecules of the invention are those encoding the $V_H$ and $V_\kappa$ sequences of the anti-PD-1 HuMAbs, 17D8, 2D3, 4H1, 5C4, 4A11, 7D3 and 5F4 (disclosed in U.S. Pat. No. 8,008,449), and those encoding the $V_H$ and $V_\kappa$ sequences of the anti-PD-L1 HuMAbs, 3G10, 12A4, 10A5, 5F8, 10H10, 1B12, 7H1, 11E6, 12B7, and 13G4 (disclosed in U.S. Pat. No. 7,943,743). An isolated DNA encoding the $V_H$ region can be converted to a full-length heavy chain gene by operatively linking the $V_H$-encoding DNA to another DNA molecule encoding heavy chain constant regions ($C_{H1}$, $C_{H2}$ and $C_{H3}$), the sequences of which are known in the art and can be obtained by standard PCR amplification. The heavy chain constant region can be an IgG1, IgG2, IgG3, IgG4, IgA, IgE, IgM or IgD constant region, but is preferably an IgG1 or IgG4 constant region. Similarly, an isolated DNA encoding the $V_L$ region can be converted to a full-length light chain gene by operatively linking the $V_L$-encoding DNA to another DNA molecule encoding the light chain constant region ($C_L$), the sequence of which is known in the art and can be obtained by standard PCR amplification. The light chain constant region can be a kappa or lambda constant region, but most preferably is a kappa constant region.

Pharmaceutical Compositions

Antibodies of the present invention may be constituted in a composition, e.g., a pharmaceutical composition, containing one Ab or a combination of Abs, or an antigen-binding portion(s) thereof, and a pharmaceutically acceptable carrier. As used herein, a "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). A pharmaceutical composition of the invention may include one or more pharmaceutically acceptable salts, anti-oxidant, aqueous and nonaqueous carriers, and/or adjuvants such as preservatives, wetting agents, emulsifying agents and dispersing agents.

Dosage regimens are adjusted to provide the optimum desired response, e.g., a therapeutic response or minimal adverse effects. For administration of an anti-PD-1 or anti-PD-L1 Ab, the dosage ranges from about 0.0001 to about 100 mg/kg, usually from about 0.001 to about 20 mg/kg, and more usually from about 0.01 to about 10 mg/kg, of the subject's body weight. Preferably, the dosage is within the range of 0.1-10 mg/kg body weight. For example, dosages can be 0.1, 0.3, 1, 3, 5 or 10 mg/kg body weight, and more preferably, 0.3, 1, 3, or 10 mg/kg body weight. The dosing schedule is typically designed to achieve exposures that result in sustained receptor occupancy (RO) based on typical pharmacokinetic properties of an Ab. An exemplary treatment regime entails administration once per week, once every two weeks, once every three weeks, once every four weeks, once a month, once every 3 months or once every three to 6 months. The dosage and scheduling may change during a course of treatment. For example, dosing schedule may comprise administering the Ab: (i) every two weeks in 6-week cycles; (ii) every four weeks for six dosages, then every three months; (iii) every three weeks; (iv) 3-10 mg/kg body weight once followed by 1 mg/kg body weight every 2-3 weeks. Considering that an IgG4 Ab typically has a half-life of 2-3 weeks, a preferred dosage regimen for an anti-PD-1 or anti-PD-L1 Ab of the invention comprises 0.3-10 mg/kg body weight, preferably 3-10 mg/kg body weight, more preferably 3 mg/kg body weight via intravenous administration, with the Ab being given every 14 days in up to 6-week or 12-week cycles until complete response or confirmed progressive disease.

In some methods, two or more mAbs with different binding specificities are administered simultaneously, in which case the dosage of each Ab administered falls within the ranges indicated. Antibody is usually administered on multiple occasions. Intervals between single dosages can be, for example, weekly, every 2 weeks, every 3 weeks, monthly, every three months or yearly. Intervals can also be irregular as indicated by measuring blood levels of Ab to the target antigen in the patient. In some methods, dosage is adjusted to achieve a plasma Ab concentration of about 1-1000 µg/ml and in some methods about 25-300 µg/ml.

Alternatively, the Ab can be administered as a sustained release formulation, in which case less frequent administration is required. Dosage and frequency vary depending on the half-life of the Ab in the patient. In general, human Abs show the longest half-life, followed by humanized Abs, chimeric Abs, and nonhuman Abs. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being unduly toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A composition of the present invention can be administered via one or more routes of administration using one or more of a variety of methods well known in the art. As will be appreciated by the skilled artisan, the route and/or mode of administration will vary depending upon the desired results.

Uses and Methods of the Invention

The Abs, Ab compositions, nucleic acids and methods of the present invention have numerous in vitro and in vivo utilities including, for example, methods to determine and quantify the expression of PD-1 or PD-L1 comprising binding of the Abs to the target polypeptides or measuring the amount of nucleic acid encoding these polypeptides, and a method for immunotherapy of a subject afflicted with a disease comprising administering to the subject a composition comprising a therapeutically effective amount of a therapeutic agent that inhibits signaling from an inhibitory immunoregulator. In preferred embodiments of the latter method, the inhibitory immunoregulator is a component of the PD-1/PD-L1 signaling pathway, and the therapeutic agent disrupts signaling of this pathway. More preferably, the therapeutic agent is an Ab that interferes with the interaction between PD-1 and PD-L1. In certain preferred embodiments of this method, the Ab binds specifically to PD-1 and blocks the interaction of PD-1 with PD-L1 and/or PD-L2. In other preferred embodiments, the therapeutic agent is an Ab that binds specifically to PD-L1 and blocks the interaction of PD-L1 with PD-1 and/or B7-1 (CD80). Thus, the disclosure provides methods for potentiating an immune response in a subject comprising administering an anti-PD-1 and/or an anti-PD-L1 Ab in order to disrupt the interaction between PD-1 and PD-L1, and methods of treating diseases mediated by such a potentiation of the immune response. When Abs to PD-1 and PD-L1 are administered together, the two can be administered sequentially in either order or simultaneously. In certain aspects, this disclosure provides methods of modifying an immune response in a subject comprising administering to the subject an anti-PD-1 and/or an anti-PD-L1 Ab of the invention, or antigen-binding portion thereof, such that the immune response in the subject is modified. Preferably, the immune response is potentiated, enhanced, stimulated or up-regulated. In preferred embodiments, the Abs of the present invention are human Abs.

Preferred subjects include human patients in need of enhancement of an immune response. The immunotherapeutic methods disclosed herein are particularly suitable for treating human patients having a disorder that can be treated by potentiating a T-cell mediated immune response. In certain embodiments, the methods are employed for treatment of subjects afflicted with a disease caused by an infectious agent. In preferred embodiments, the methods are employed for treatment of subjects afflicted with, or at risk of being afflicted with, a cancer.

Cancer Immunotherapy

Blockade of PD-1/PD-L1 interaction has been shown to potentiate immune responses in vitro (U.S. Pat. Nos. 8,008,449 and 7,943,743; Fife et al., 2009) and mediate preclinical antitumor activity (Dong et al., 2002; Iwai et al., 2002). However, the molecular interactions potentially blocked by these two Abs are not identical: anti-PD-1 Abs of the invention disrupt PD-1/PD-L1 and potentially PD-1/PD-L2 interactions; in contrast, whereas anti-PD-L1 Abs of the invention also disrupt PD-1/PD-L1 interactions, they do not block PD-1/PD-L2 interactions but instead may disrupt the PD-1-independent PD-L1/CD80 interaction, which has also been shown to down-modulate T-cell responses in vitro and in vivo (Park et al., 2010; Paterson et al., 2011; Yang et al., 2011; Butte et al., 2007; Butte et al., 2008). Thus, it is possible that among these varied ligand-receptor pairings, different interactions may dominate in different cancer types, contributing to dissimilar activity profiles for the two Abs.

Disruption of the PD-1/PD-L1 interaction by antagonistic Abs can enhance the immune response to cancerous cells in a patient. PD-L1 is not expressed in normal human cells, but is abundant in a variety of human cancers (Dong et al., 2002). The interaction between PD-1 and PD-L1 impairs T cell responses as manifested by a decrease in tumor-infiltrating lymphocytes (TILs) and a decrease in T-cell receptor mediated proliferation, resulting in T cell anergy, exhaustion or apoptosis, and immune evasion by the cancerous cells (Zou et al., 2008; Blank et al., 2005; Konishi et al., 2004; Dong et al., 2003; Iwai et al., 2002) Immune suppression can be reversed by inhibiting the local interaction between PD-L1 and PD-1 using an anti-PD-1 and/or an anti-PD-L1 Ab. These Abs may be used alone or in combination to inhibit the growth of cancerous tumors. In addition, either or both of these Abs may be used in conjunction with other immunogenic agents including cytokines, standard cancer chemotherapies, vaccines, radiation, surgery, or other Abs.

Immunotherapy of Cancer Patients Using an Anti-PD-1 Antibody

This disclosure provides a method for immunotherapy of a subject afflicted with cancer, which method comprises administering to the subject a composition comprising a therapeutically effective amount of an Ab or an antigen-binding portion thereof that disrupts the interaction of PD-1 with PD-L1 and/or PD-L2. The disclosure also provides a method of inhibiting growth of tumor cells in a subject, comprising administering to the subject an Ab or an antigen-binding portion thereof that disrupts the interaction of PD-1 with PD-L1 and/or PD-L2 in an amount effective to inhibit growth of the tumor cells. In preferred embodiments, the subject is a human. In other preferred embodiments, the Ab or antigen-binding portion thereof is an anti-PD-1 Ab of the invention or an antigen-binding portion thereof. In certain embodiments, the Ab or antigen-binding portion thereof is of an IgG1 or IgG4 isotype. In certain embodiments, the Ab or antigen-binding portion thereof is a mAb or an antigen-binding portion thereof. In certain other embodiments, the Ab or antigen-binding portion thereof is a chimeric, humanized or human Ab or an antigen-binding portion thereof. In preferred embodiments for treating human subjects, the Ab or antigen-binding portion thereof is a human Ab or an antigen-binding portion thereof.

The clinical trials described in the Examples employed the anti-PD-1 HuMAb, nivolumab (designated 5C4 in U.S. Pat. No. 8,008,449), to treat cancer. While 5C4 was selected as the lead Ab for entering the clinic, it is notable that several anti-PD-1 Abs of the invention share with 5C4 functional properties that are important to the therapeutic activity of 5C4, including high affinity binding specifically to human PD-1, increasing T-cell proliferation, IL-2 secretion and interferon-γ production in an MLR assay, inhibiting the binding of PD-L1 and/or PD-L2 to PD-1, and inhibiting tumor cell growth in vivo. Moreover, certain of the anti-PD-1 Abs of the invention, 17D8, 2D3, 4H1 and 7D3 are structurally related to 5C4 in comprising $V_H$ and $V_\kappa$ regions that have sequences derived from $V_H$ 3-33 and $V_\kappa$ L6 germline sequences, respectively. In addition, 5C4, 2D3, 7D3, 4H1 and 17D8 all cross-compete for binding to the same epitope region of hPD-1 (Example 1). Thus, the preclinical characterization of nivolumab and other anti-PD-1 HuMabs indicate that the methods of treating cancer provided herein may be performed using different Abs selected from the broad genus of anti-PD-1 Abs of the invention.

Accordingly, certain embodiments of the immunotherapy methods disclosed herein comprise administering to a patient an anti-PD-1 Ab or antigen-binding portion thereof comprising: (a) a heavy chain variable region that comprises consecutively linked amino acids having a sequence derived from a human $V_H$ 3-33 germline sequence, and a light chain variable region that comprises consecutively linked amino acids having a sequence derived from a human $V_\kappa$ L6 germline sequence, or (b) a heavy chain variable region that comprises consecutively linked amino acids having a sequence derived from a human $V_H$ 4-39 germline sequence, and a light chain variable region that comprises consecutively linked amino acids having a sequence derived from a human $V_\kappa$ L15 germline sequence.

In certain other embodiments, the Ab or antigen-binding portion thereof that is administered to the patient cross-competes for binding to PD-1 with a reference Ab or a reference antigen-binding portion thereof comprising: (a) a human heavy chain variable region comprising consecutively linked amino acids having the sequence set forth in SEQ ID NO: 1 and a human light chain variable region comprising consecutively linked amino acids having the sequence set forth in SEQ ID NO: 8; (b) a human heavy chain variable region comprising consecutively linked amino acids having the sequence set forth in SEQ ID NO: 2 and a human light chain variable region comprising consecutively linked amino acids having the sequence set forth in SEQ ID NO: 9; (c) a human heavy chain variable region comprising consecutively linked amino acids having the sequence set forth in SEQ ID NO: 3 and a human light chain variable region comprising consecutively linked amino acids having the sequence set forth in SEQ ID NO: 10; (d) a human heavy chain variable region comprising consecutively linked amino acids having the sequence set forth in SEQ ID NO: 4 and a human light chain variable region comprising consecutively linked amino acids having the sequence set forth in SEQ ID NO: 11; (e) a human heavy chain variable region comprising consecutively linked amino acids having the sequence set forth in SEQ ID NO: 5 and a human light chain variable region comprising consecutively linked amino acids having the sequence set forth in SEQ ID NO: 12; (f) a human heavy chain variable region comprising consecutively linked amino acids having the sequence set forth in SEQ ID NO: 6 and a human light chain variable region comprising consecutively linked amino acids having the sequence set forth in SEQ ID NO: 13; or (g) a human heavy chain variable region comprising consecutively linked amino acids having the sequence set forth in SEQ ID NO: 7 and a human light chain variable region comprising consecutively linked amino acids having the sequence set forth in SEO ID NO: 14. In preferred embodiments, the Ab or antigen-binding portion thereof cross-competes for binding to PD-1 with nivolumab.

In certain preferred embodiments of the immunotherapy methods disclosed herein, the anti-PD-1 Ab or antigen-binding portion thereof administered to the patient comprises: (a) a human heavy chain variable region comprising consecutively linked amino acids having the sequence set forth in SEQ ID NO: 1 and a human light chain variable region comprising consecutively linked amino acids having the sequence set forth in SEQ ID NO: 8; (b) a human heavy chain variable region comprising consecutively linked amino acids having the sequence set forth in SEQ ID NO: 2 and a human light chain variable region comprising consecutively linked amino acids having the sequence set forth in SEQ ID NO: 9; (c) a human heavy chain variable region comprising consecutively linked amino acids having the sequence set forth in SEQ ID NO: 3 and a human light chain variable region comprising consecutively linked amino acids having the sequence set forth in SEQ ID NO: 10; (d) a human heavy chain variable region comprising consecutively linked amino acids having the sequence set forth in SEQ ID NO: 4 and a human light chain variable region comprising consecutively linked amino acids having the sequence set forth in SEQ ID NO: 11; (e) a human heavy chain variable region comprising consecutively linked amino acids having the sequence set forth in SEQ ID NO: 5 and a human light chain variable region comprising consecutively linked amino acids having the sequence set forth in SEQ ID NO: 12; (f) a human heavy chain variable region comprising consecutively linked amino acids having the sequence set forth in SEQ ID NO: 6 and a human light chain variable region comprising consecutively linked amino acids having the sequence set forth in SEQ ID NO: 13; or (g) a human heavy chain variable region comprising consecutively linked amino acids having the sequence set forth in SEQ ID NO: 7 and a human light chain variable region comprising consecutively linked amino acids having the sequence set forth in SEO ID NO: 14. In more preferred embodiments, the anti-PD-1 Ab or antigen-binding portion comprises a human heavy chain variable region comprising consecutively linked amino acids having the sequence set forth in SEQ ID NO: 4 and a human light chain variable region comprising consecutively linked amino acids having the sequence set forth in SEQ ID NO: 11. In yet more preferred embodiments, the anti-PD-1 Ab is nivolumab.

In the clinical trials of anti-PD-1 immunotherapy described in the Examples below, intriguing ORs with durable clinical responses, even in heavily pretreated patients, were observed across multiple tumor types including a substantial proportion of NSCLC, MEL, and RCC patients and in various sites of metastasis including liver, lung, lymph nodes, and bone. See, also, Topalian et al. (2012b). MEL and RCC are considered to be immunogenic neoplasms, having previously been demonstrated to be responsive to cancer immunotherapy, e.g., IL-2 (McDermott et al., 2006) and/or anti-CTLA-4 Ab (Hodi et al., 2010). In contrast, NSCLC has been considered "non-immunogenic" and poorly responsive to immune-based therapies (Holt et al., 2011). Thus, the results with NSCLC are particularly striking, unexpected and surprising. In NSCLC patients, based on data analyzed up to February 2012, 14 ORs were observed at BMS-936558 doses of 1, 3, or 10 mg/kg with response rates of 6%, 32%, and 18%, respectively. ORs were observed across NSCLC histologies: 6 responders of 18 squamous (33%), 7 of 56 nonsquamous (13%), and 1 of 2 unknown. This level of activity seen with anti-PD-1 in NSCLC patients with significant prior therapy (47% with 3 lines of previous therapy) and across histologies is unique, particularly in the squamous histology patients (cf. Gridelli et al., 2008; Miller, 2006), and provides a very favorable benefit/risk dynamic regarding efficacy and safety compared to existing standard-of-care.

Durability of Clinical Responses to Anti-PD-1 in Heavily Pretreated Cancer Patients The durability of ORs across multiple cancer types in patients treated with the anti-PD-1 Ab is particularly notable. The objective response rate (ORR) in heavily pretreated NSCLC patients receiving anti-PD-1 Ab, including patients with squamous histology, is particularly surprising and unexpected, as standard salvage therapies historically show modest benefit in these patients (Scagliotti et al., 2011). As measured by standard RECIST in this study, ORs were long-lasting, with response durations ≥1 year in 20 of 31 responders in the data analyzed up to February 2012. In addition, patterns of tumor regression consistent with immune-related patterns of response were observed.

These findings have established the PD-1 pathway as a new therapeutic focus in oncology (Pardoll, 2012; Topalian et al., 2012c; McDermott et al., 2013). In the current study, in which 47% of patients had progressive disease following 3 or more prior systemic regimens, preliminary analysis has been conducted up to March 2013. This updated analysis has supported and reinforced the data obtained and conclusions reached from the earlier February 2012 analyses. Thus, conventional ORs were documented in patients with NSCLC (16%), MEL (31%) and RCC (29%), and prolonged disease stabilization in others (9%, 6%, and 27%, respectively) across all doses tested (see Example 7, Table 2). Additionally, 13 patients (4%) manifested unconventional, "immune-related" response patterns as previously described with anti-CTLA-4 therapy, several of which were sustained (Sharma et al., 2011). The updated analyses again underscored the durability of survival in nivolumab-treated patients, which has not been observed with chemotherapy or small molecule inhibitors to date, but has been observed in patients with advanced melanoma receiving ipilimumab, another immune checkpoint blocking agent (Hodi et al., 2010).

Of particular importance, the objective tumor regression and disease stabilization induced by nivolumab in heavily-pretreated patients with advanced NSCLC, MEL, and RCC translate to survival outcomes that compare very favorably with historical data for these patient populations treated with conventional chemotherapy and/or tyrosine-kinase inhibitor (TKI) treatments. In NSCLC, nivolumab induced median overall survivals of 9.6 and 9.2 months in patients with squamous and non-squamous histologies, respectively. Landmark survival rates of 43% (1-year), 32% (2-year) and 24% (3-year) were achieved (see Example 7, Table 2). This high level of efficacy is especially impressive since 55% of these patients had received 3 or more prior therapies. Historically, 2 L chemotherapeutics for lung cancer (i.e., docetaxel and pemetrexed) have achieved a median overall survival of 7.5-8.3 months (Shepherd et al., 2000; Hanna et al., 2004). In a 2/3-L population, erlotinib-treated patients had a median survival of 6.7 months, versus 4.7 months in placebo-treated patients (Shepherd et al., 2005). No therapy is currently approved for use in lung cancer beyond the 3 L setting, and minimal data exist to benchmark survival in this patient population.

In nivolumab-treated MEL patients, overall survival (OS) of 16.8 months was achieved, with landmark survival rates of 61% (1-year), 44% (2-year) and 40% (3-year) (see Example 7, Table 2). Survival outcomes in pretreated melanoma patients supported the recent PDA approvals of ipilimumab and vemurafenib. In patients with at least one prior treatment for metastatic disease, ipilimumab increased median OS from 6.4 to 10.1 months, compared to a gp100 peptide vaccine (Hodi et al., 2010). In phase 2 trials of ipilimumab in previously treated patients, landmark 2-year survival rates ranged from 24.2-32.8% (Lebbe et al., 2012). Median OS in previously treated MEL patients enrolled on a large phase 2 of vemurafenib was 15.9 months (Sosman et al., 2012).

In nivolumab-treated patients with RCC, among whom 44% received 3 or more prior therapies and 74% received prior anti-angiogenic therapy, the median OS has not been achieved and exceeds 22 months. Landmark survival rates of 70% (1-year), 52% (2-year) and 52% (3-year) were achieved (see Example 7, Table 2). In a recent Phase 3 trial enrolling kidney cancer patients whose disease progressed following anti-angiogenic therapy, everolimus was compared with placebo: median OS was 14.8 versus 14.4 months, respectively (Motzer et al., 2008; Motzer et al., 2008). A recent Phase 3 trial comparing sorafenib to temsirolimus in a sunitinib-refractory kidney cancer population yielded median OS of 16.6 and 12.3 months, respectively (Hutson et al., 2012). Thus, treatment of a heavily-pretreated patient population with nivolumab has yielded a considerably longer median OS (>22 months) than treatment of a less refractory population with standard-of-care therapies. Controlled Phase 3 trials with prospective survival endpoints are underway in NSCLC, MEL and RCC (NCT01673867, NCT01721772, NCT01642004, NCT01668784, and NCT01721746 (see Clinical Trials Website). The results from these trials are expected to further demonstrate the high efficacy of, and durability of responses to, nivolumab in these cancers compared standard-of-care therapies.

The data disclosed herein demonstrating the high efficacy, durability and broad applicability of anti-PD-1 immunotherapy for treating cancer has led to nivolumab being tested for additional types of cancer. For example, on the basis that increased PD-L1 expression has been reported with various hematologic malignancies and may prevent the host immune response from exerting a beneficial impact on the malignant cells, a trial to confirm the ability of nivolumab to mediate antitumor activity in patients with hematologic malignancies (multiple myeloma, B-cell lymphoma, T-cell lymphoma, Hodgkin's lymphoma/primary mediastinal B-cell lymphoma, and chronic myelogenous leukemia) has been initiated (NCT01592370). Nivolumab is also being tested as a monotherapy in advanced hepatocellular carcinoma (NCT01658878).

In summary, the results of anti-PD-1 immunotherapy disclosed herein are remarkable in at least the following three respects. First, anti-PD-1 has been shown to be highly efficacious compared to historical data for patients on standard-of-care treatments for cancer. Notably, this efficacy has been demonstrated in patient in heavily pretreated populations in which about half of the patients had progressive disease following 3 or more prior systemic regimens. Such patients, afflicted with advanced, metastatic and/or refractory cancers, are notoriously difficult to treat. Accordingly, this disclosure provides methods for immunotherapy of a patient afflicted with an advanced, metastatic and/or refractory cancer, which method comprises administering to the patient a therapeutically effective amount of an Ab or an antigen-binding portion thereof that disrupts the interaction of PD-1 with PD-L1 and/or PD-L2. In certain embodiments of any of the therapeutic methods disclosed herein, the subject has been pre-treated for the cancer; for example, the subject had undergone at least one, two, or three prior lines of therapy for cancer.

Second, the present therapeutic methods have been shown to be applicable to a broad genus of different cancers. Based on the surprising discovery that even a "non-immunogenic" cancer such as NSCLC (Holt et al., 2011) and hard-to-treat cancers such as ovarian and gastric cancers (as well as other cancers tested, including MEL, RCC, and CRC) are amendable to treatment with anti-PD-1 and/or anti-PD-L1 (see Examples 7 and 14), this disclosure provides methods for immunotherapy of a patient afflicted with any cancer.

Third, treatment with an anti-PD-1 or anti-PD-L1 Ab has been shown to produce strikingly durable clinical activity in cancer patients. Accordingly, this disclosure provides immunotherapeutic methods of inducing a durable clinical response in a cancer patient comprising administering to the patient a therapeutically effective amount of an Ab or an antigen-binding portion thereof that disrupts the interaction of PD-1 with PD-L1 and/or PD-L2. In preferred embodiments of any of the therapeutic methods described herein, the clinical response is a durable response.

As used herein, a "durable" response is a therapeutic or clinical response that exceeds the anticipated median OS rate in a patient population. The anticipated median OS rate varies with different cancer and different patient populations. In certain embodiments, a durable response exceeds the anticipated median OS rate in the relevant patient population by at least 10%, preferably by at least 20%, more preferably by at least 30%, and even more preferably by at least 50%. A major benefit of immunotherapeutic approaches based on PD-1 pathway blockade may be the functional restoration of exhausted T cells with long-term generation of memory T cells that may maintain antitumor immune surveillance and inhibit tumor growth for prolonged periods extending to many years, even in the absence of continued therapy (Kim et al., 2010). Indeed, long-term follow-up studies on patients following cessation of nivolumab therapy have confirmed that a patient with CRC experienced a complete response which was ongoing after 3 years; a patient with RCC experienced a partial response lasting 3 years off therapy, which converted to a complete response that was ongoing at 12 months; and a patient with melanoma achieved a partial response that was stable for 16 months off therapy, and recurrent disease was successfully treated with reinduction anti-PD-1 therapy (Lipson et al., 2013).

Combination Therapy Including Anti-PD-1 Abs

While monotherapy with anti-PD-1 and anti-PD-L1 Abs has been shown herein to significantly increase the survival of patients with lung cancer, melanoma, kidney cancer, and potentially other malignancies, preclinical evidence indicates that synergistic treatment combinations based on PD-1 pathway blockade could have even more potent effects. Clinical evaluation of nivolumab combined with ipilimumab (anti-CTLA-4), whose mechanism of action is similar yet distinct from nivolumab's (Mellman et al., 2011; Topalian et al., 2012c), is ongoing (Wolchok et al., 2013), as are studies of nivolumab in combination with melanoma vaccines (NCT01176461, NCT01176474; Weber et al., 2013), and BMS-986015, an anti-KIR Ab (NCT01714739).

Anti-PD-1 Abs can be combined with an immunogenic agent, for example a preparation of cancerous cells, purified tumor antigens (including recombinant proteins, peptides, and carbohydrate molecules), antigen-presenting cells such as dendritic cells bearing tumor-associated antigens, and/or cells transfected with genes encoding immune stimulating cytokines (He et al., 2004). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF. PD-1 blockade may also be effectively combined with standard cancer treatments, including chemotherapeutic regimes, radiation, surgery, hormone deprivation and angiogenesis inhibitors, as well as another immunotherapeutic Ab (e.g., an anti-PD-L1, anti-CTLA-4 and/or anti-LAG-3 Ab).

Immune-Related Clinical Responses

It has become evident that conventional response criteria may not adequately assess the activity of immunotherapeutic agents because progressive disease (by initial radiographic evaluation) does not necessarily reflect therapeutic failure. For example, treatment with the anti-CTLA-4 Ab, ipilimumab, has been shown to produce four distinct response patterns, all of which were associated with favorable survival: (a) shrinkage in baseline lesions, without new lesions; (b) durable stable disease (in some patients followed by a slow, steady decline in total tumor burden); (c) response after an increase in total tumor burden; and (d) response in the presence of new lesions. Accordingly, to properly evaluate immunotherapeutic agents, long-term effects on the target disease must also be captured. In this regard, systematic immune-related response criteria (irRC) that make allowances for an early increase in tumor burden and/or the appearance of new lesions, and which seek to enhance the characterization of immune-related response patterns, have been proposed (Wolchok et al., 2009). While the full impact of these unconventional response patterns remains to be defined in randomized trials of nivolumab with survival endpoints, the present observations are reminiscent of findings with ipilimumab in which a significant extension of OS was observed in treated patients (Hodi et al., 2010; Robert et al., 2011).

The overall risk/benefit profile of anti-PD-1 immunotherapy is also favorable, with a low incidence of more severe drug-related adverse events (AEs; >grade 3), the specific events observed to date being consistent with other immunotherapeutic agents. This suggests that anti-PD-1 immunotherapy can be delivered in an outpatient setting with minimal supportive care.

Broad Spectrum of Cancers Treatable by Anti-PD-1 Immunotherapy

The clinical data presented herein demonstrate that immunotherapy based on PD-1 blockade is not limited to only "immunogenic" tumor types, such as MEL and RCC, but extends to tumor types not generally considered to be immune-responsive, including NSCLC. The unexpected successes with treatment-refractory metastatic NSCLC underscore the possibility that any neoplasm can be "immunogenic" in the context of proper immune modulation, and suggest that PD-1 blockade as an immunotherapeutic approach is broadly applicable across a very diverse range of tumor types. Cancers that may be treated using the anti-PD-1 Abs of the invention also include cancers typically responsive to immunotherapy. Non-limiting examples of preferred cancers for treatment include NSCLC, MEL, RCC, CRC, CRPC, HCC, squamous cell carcinoma of the head and neck, carcinomas of the esophagus, ovary, gastrointestinal tract and breast, and a hematologic malignancy. Although NSCLC is not generally considered responsive to immunotherapy, data disclosed herein unexpectedly demonstrate that both squamous and non-squamous NSCLC are responsive to treatment with an anti-PD-1 Ab. Additionally, the disclosure provides for the treatment of refractory or recurrent malignancies whose growth may be inhibited using an anti-PD-1 Ab of the invention.

Examples of other cancers that may be treated using an anti-PD-1 Ab in the methods of the present invention, based on the indications of very broad applicability of anti-PD-1 immunotherapy provided herein, include liver cancer, bone cancer, pancreatic cancer, skin cancer, cancer of the head or neck, breast cancer, lung cancer, cutaneous or intraocular malignant melanoma, renal cancer, uterine cancer, ovarian cancer, colorectal cancer, colon cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, environmentally induced cancers including those induced by asbestos, hematologic malignancies including, for example, multiple myeloma, B-cell lymphoma, Hodgkin lymphoma/primary mediastinal B-cell lymphoma, non-Hodgkin's lymphomas, acute myeloid lymphoma, chronic myelogenous leukemia, chronic lymphoid leukemia, follicular lymphoma, diffuse large B-cell lymphoma, Burkitt's lymphoma, immunoblastic large cell lymphoma, precursor B-lymphoblastic lymphoma, mantle cell lymphoma, acute lymphoblastic leukemia, mycosis fungoides, anaplastic large cell lymphoma, T-cell lymphoma, and precursor T-lymphoblastic lymphoma, and any combinations of said cancers. The present invention is also applicable to treatment of metastatic cancers.

Medical Uses of Anti-PD-1 Abs

One aspect of this invention is the use of any anti-PD-1 Ab or antigen-binding portion thereof of the invention for the preparation of a medicament for inhibiting signaling from the PD-1/PD-L1 pathway so as to thereby potentiate an endogenous immune response in a subject afflicted with cancer. Another aspect is the use of any anti-PD-1 Ab or an antigen-binding portion thereof of the invention for the preparation of a medicament for immunotherapy of a subject afflicted with cancer comprising disrupting the interaction between PD-1 and PD-L1. These uses for the preparation of medicaments are broadly applicable to the full range of cancers disclosed herein. In preferred embodiments of these uses, the cancers include squamous NSCLC, non-squamous NSCLC, MEL, RCC, CRC, CRPC, HCC, squamous cell carcinoma of the head and neck, and carcinomas of the esophagus, ovary, gastrointestinal tract and breast, and a hematologic malignancy. This disclosure also provides medical uses of any anti-PD-1 Ab or antigen-binding portion thereof of the invention corresponding to all the embodiments of the methods of treatment employing an anti-PD-1 Ab described herein.

The disclosure also provides an anti-PD-1 Ab or an antigen-binding portion thereof of the invention for use in potentiating an endogenous immune response in a subject afflicted with cancer by inhibiting signaling from the PD-1/PD-L1 pathway. The disclosure further provides an anti-PD-1 Ab or an antigen-binding portion thereof of the invention for use in immunotherapy of a subject afflicted with cancer comprising disrupting the interaction between PD-1 and PD-L1. These Abs may be used in potentiating an endogenous immune response against, or in immunotherapy of, the full range of cancers disclosed herein. In preferred embodiments, the cancers include squamous NSCLC, non-squamous NSCLC, MEL, RCC, CRC, CRPC, HCC, squamous cell carcinoma of the head and neck, and carcinomas of the esophagus, ovary, gastrointestinal tract and breast, and a hematologic malignancy.

Immunotherapy of Cancer Patients Using an Anti-PD-L1 Antibody

PD-L1 is the primary PD-1 ligand up-regulated within solid tumors, where it can inhibit cytokine production and the cytolytic activity of PD-1-positive, tumor-infiltrating $CD4^+$ and $CD8^+$ T-cells, respectively (Dong et al., 2002; Hino et al., 2010; Taube et al., 2012). These properties make PD-L1 a promising target for cancer immunotherapy. The clinical trials of anti-PD-L1 immunotherapy described in the Examples demonstrate for the first time that mAb blockade of the immune inhibitory ligand, PD-L1, produces both durable tumor regression and prolonged (≥24 weeks) disease stabilization in patients with metastatic NSCLC, MEL, RCC and OV, including those with extensive prior therapy. The human anti-PD-L1 HuMAb, BMS-936559, had a favorable safety profile overall at doses up to and including 10 mg/kg, as is evident from the low (9%) incidence of grade 3-4 drug-related AEs. These findings are consistent with the mild autoimmune phenotype seen in PD-L1$^{-/-}$ mice (Dong et al., 2004) and the more severe hyperproliferation seen in CTLA-4$^{-/-}$ mice relative to PD-1$^{-/-}$ mice (Phan et al., 2003; Tivol et al., 1995; Nishimura et al., 1999). Most of the toxicities associated with anti-PD-L1 administration in patients were immune-related, suggesting on-target effects. The spectrum and frequency of adverse events of special interest (AEOSIs) is somewhat different between anti-PD-L1 and anti-CTLA-4, emphasizing the distinct biology of these pathways (Ribas et al., 2005). Infusion reactions were observed with BMS-936559, although they were mild in most patients. Severe colitis, a drug-related AE observed in ipilimumab-treated patients (Beck et al., 2006), was infrequently noted with anti-PD-L1.

As noted above for anti-PD-1 immunotherapy, another important feature of anti-PD-L1 therapy is the durability of responses across multiple tumor types. This is particularly notable considering the advanced disease and prior treatment of patients on the current study. Although not compared directly, this durability appears greater than that observed with most chemotherapies and kinase inhibitors used in these diseases.

Because peripheral blood T-cells express PD-L1, it is possible to assess in vivo RO by BMS-963559 as a pharmacodynamic measure. Median RO was 65.8%, 66.2%, and 72.4% for the doses tested. Whereas these studies provide a direct assessment and evidence of target engagement in patients treated with BMS-936559, relationships between RO in peripheral blood and the tumor microenvironment remain poorly understood.

Based on the clinical data disclosed herein, this disclosure provides a method for immunotherapy of a subject afflicted with cancer, which method comprises administering to the subject a composition comprising a therapeutically effective amount of an anti-PD-L1 Ab of the invention or an antigen-binding portion thereof. The disclosure also provides a method of inhibiting growth of tumor cells in a subject, comprising administering to the subject an anti-PD-L1 Ab of the invention or an antigen-binding portion thereof. In preferred embodiments, the subject is a human. In certain embodiments, the Ab or antigen-binding portion thereof is of an IgG1 or IgG4 isotype. In certain embodiments, the Ab or antigen-binding portion thereof is a mAb or an antigen-binding portion thereof. In certain other embodiments, the Ab or antigen-binding portion thereof is a chimeric, humanized or human Ab or an antigen-binding portion thereof. In preferred embodiments for treating human subjects, the Ab or antigen-binding portion thereof is a human Ab or an antigen-binding portion thereof.

Clinical trials described in the Examples employed the anti-PD-L1 HuMAb BMS-936559 to treat cancer. While BMS-936559 (designated HuMAb 12A4 in U.S. Pat. No. 7,943,743) was selected as the lead anti-PD-L1 Ab for entering the clinic, it is notable that several anti-PD-L1 Abs of the invention share with 12A4 functional properties that are important to the therapeutic activity of 12A4, including high affinity binding specifically to human PD-L1, increasing T-cell proliferation, IL-2 secretion and interferon-γ production in an MLR assay, inhibiting the binding of PD-L1 to PD-1, and reversing the suppressive effect of T regulatory cells on T cell effector cells and/or dendritic cells. Moreover, certain of the anti-PD-L1 Abs of the invention, namely 1B12, 7H1 and 12B7 are structurally related to 12A4 in comprising $V_H$ and $V_K$ regions that have sequences derived from $V_H$ 1-69 and $V_K$ L6 germline sequences, respectively. In addition, at least 12B7, 3G10, 1B12 and 13G4 cross-compete with 12A4 for binding to the same epitope region of hPD-L1, whereas 5F8 and 10A5 may bind to the same or an overlapping epitope region as 12A4 (Examples 2 and 3). Thus, the preclinical characterization of 12A4 and other anti-PD-L1 HuMabs indicate that the methods of treating cancer provided herein may be performed using any of the broad genus of anti-PD-L1 Abs of the invention.

Accordingly, this disclosure provides immunotherapy methods comprising administering to a patient an anti-PD-L1 Ab or antigen-binding portion thereof comprising (a) a heavy chain variable region that comprises consecutively linked amino acids having a sequence derived from a human $V_H$ 1-18 germline sequence, and a light chain variable region that comprises consecutively linked amino acids having a sequence derived from a human $V_\kappa$ L6 germline sequence; (b) a heavy chain variable region that comprises consecutively linked amino acids having a sequence derived from a human $V_H$ 1-69 germline sequence, and a light chain variable region that comprises consecutively linked amino acids having a sequence derived from a human $V_\kappa$ L6 germline sequence; (c) a heavy chain variable region that comprises consecutively linked amino acids having a sequence derived from a human $V_H$ 1-3 germline sequence, and a light chain variable region that comprises consecutively linked amino acids having a sequence derived from a human $V_\kappa$ L15 germline sequence; (d) a heavy chain variable region that comprises consecutively linked amino acids having a sequence derived from a human $V_H$ 1-69 germline sequence, and a light chain variable region that comprises consecutively linked amino acids having a sequence derived from a human $V_\kappa$ A27 germline sequence; (e) a heavy chain variable region that comprises consecutively linked amino acids having a sequence derived from a human $V_H$ 3-9 germline sequence, and a light chain variable region that comprises consecutively linked amino acids having a sequence derived from a human $V_\kappa$ L15germline sequence; or (f) a heavy chain variable region that comprises consecutively linked amino acids having a sequence derived from a human $V_H$ 3-9 germline sequence, and a light chain variable region that comprises consecutively linked amino acids having a sequence derived from a human $V_\kappa$ L18germline sequence.

In certain other embodiments, the anti-PD-L1 Ab or antigen-binding portion thereof administered to the patient cross-competes for binding to PD-L1 with a reference Ab or a reference antigen-binding portion thereof comprising: (a) a human heavy chain variable region comprising consecutively linked amino acids having the sequence set forth in SEQ ID NO: 15 and a human light chain variable region comprising consecutively linked amino acids having the sequence set forth in SEQ ID NO: 25; (b) a human heavy chain variable region comprising consecutively linked amino acids having the sequence set forth in SEQ ID NO: 16 and a human light chain variable region comprising consecutively linked amino acids having the sequence set forth in SEQ ID NO: 26; (c) a human heavy chain variable region comprising consecutively linked amino acids having the sequence set forth in SEQ ID NO: 17 and a human light chain variable region comprising consecutively linked amino acids having the sequence set forth in SEQ ID NO: 27; (d) a human heavy chain variable region comprising consecutively linked amino acids having the sequence set forth in SEQ ID NO: 18 and a human light chain variable region comprising consecutively linked amino acids having the sequence set forth in SEQ ID NO: 28; (e) a human heavy chain variable region comprising consecutively linked amino acids having the sequence set forth in SEQ ID NO: 19 and a human light chain variable region comprising consecutively linked amino acids having the sequence set forth in SEQ ID NO: 29; (f) a human heavy chain variable region comprising consecutively linked amino acids having the sequence set forth in SEQ ID NO: 20 and a human light chain variable region comprising consecutively linked amino acids having the sequence set forth in SEQ ID NO: 30; (g) a human heavy chain variable region comprising consecutively linked amino acids having the sequence set forth in SEQ ID NO: 21 and a human light chain variable region comprising consecutively linked amino acids having the sequence set forth in SEQ ID NO: 31; (h) a human heavy chain variable region comprising consecutively linked amino acids having the sequence set forth in SEQ ID NO: 22 and a human light chain variable region comprising consecutively linked amino acids having the sequence set forth in SEQ ID NO: 32; (i) a human heavy chain variable region comprising consecutively linked amino acids having the sequence set forth in SEQ ID NO: 23 and a human light chain variable region comprising consecutively linked amino acids having the sequence set forth in SEQ ID NO: 33; or (j) a human heavy chain variable region comprising consecutively linked amino acids having the sequence set forth in SEQ ID NO: 24 and a human light chain variable region comprising consecutively linked amino acids having the sequence set forth in SEQ ID NO: 34. In preferred embodiments, the Ab or antigen-binding portion thereof cross-competes for binding to PD-1 with a reference Ab or reference antigen-binding portion thereof comprising a human heavy chain variable region comprising consecutively linked amino acids having the sequence set forth in SEQ ID NO: 16 and a human light chain variable region comprising consecutively linked amino acids having the sequence set forth in SEQ ID NO: 26.

In certain preferred embodiments of the immunotherapy methods disclosed herein, the anti-PD-L1 Ab or antigen-binding portion thereof administered to the subject comprises: (a) a human heavy chain variable region comprising consecutively linked amino acids having the sequence set forth in SEQ ID NO: 15 and a human light chain variable region comprising consecutively linked amino acids having the sequence set forth in SEQ ID NO: 25; (b) a human heavy chain variable region comprising consecutively linked amino acids having the sequence set forth in SEQ ID NO: 16 and a human light chain variable region comprising consecutively linked amino acids having the sequence set forth in SEQ ID NO: 26; (c) a human heavy chain variable region comprising consecutively linked amino acids having the sequence set forth in SEQ ID NO: 17 and a human light chain variable region comprising consecutively linked amino acids having the sequence set forth in SEQ ID NO: 27; (d) a human heavy chain variable region comprising consecutively linked amino acids having the sequence set forth in SEQ ID NO: 18 and a human light chain variable region comprising consecutively linked amino acids having the sequence set forth in SEQ ID NO: 28; (e) a human heavy chain variable region comprising consecutively linked amino acids having the sequence set forth in SEQ ID NO: 19 and a human light chain variable region comprising consecutively linked amino acids having the sequence set forth in SEQ ID NO: 29; (f) a human heavy chain variable region comprising consecutively linked amino acids having the sequence set forth in SEQ ID NO: 20 and a human light chain variable region comprising consecutively linked amino acids having the sequence set forth in SEQ ID NO: 30; (g) a human heavy chain variable region comprising consecutively linked amino acids having the sequence set forth in SEQ ID NO: 21 and a human light chain variable region comprising consecutively linked amino acids having the sequence set forth in SEQ ID NO: 31; (h) a human heavy chain variable region comprising consecutively linked amino acids having the sequence set forth in SEQ ID NO: 22 and a human light chain variable region comprising consecutively linked amino acids having the sequence set forth in SEQ ID NO: 32; (i) a human heavy chain variable region comprising consecutively linked amino acids having the sequence set forth in SEQ ID NO: 23 and a human light chain variable region comprising consecutively linked amino acids having the sequence set forth in SEQ ID NO: 33; or (j) a human heavy chain variable region comprising consecutively linked amino acids having the sequence set forth in SEQ ID NO: 24 and a human light chain variable region comprising consecutively linked amino acids having the sequence set forth in SEQ ID NO: 34. In more preferred embodiments, the anti-PD-L1 Ab or antigen-binding portion comprises a human heavy chain variable region comprising consecutively linked amino acids having the sequence set forth in SEQ ID NO: 16 and a human light chain variable region comprising consecutively linked amino acids having the sequence set forth in SEQ ID NO: 26.

Broad Spectrum of Cancers Treatable by Anti-PD-L1 Immunotherapy

The clinical activity of anti-PD-L1 in patients with advanced NSCLC, similar to the activity of anti-PD-1 in these patients, was surprising and unexpected since NSCLC has been considered to be poorly responsive to immune-based therapies (Holt and Disis, 2008; Holt et al., 2011). The present clinical data obtained with BMS-936559, an anti-PD-L1 Ab of the invention, substantiate and extend the evidence obtained using the anti-PD-1 Ab that immunotherapy based on PD-1 blockade is not applicable only to "immunogenic" tumor types, such as MEL and RCC, but is also effective with a broad range of cancers, including treatment-refractory metastatic NSCLC, that are generally not considered to be immune-responsive. Preferred cancers that may be treated using the anti-PD-L1 Abs of the invention include MEL (e.g., metastatic malignant melanoma), RCC, squamous NSCLC, non-squamous NSCLC, CRC, ovarian cancer (OV), gastric cancer (GC), breast cancer (BC), pancreatic carcinoma (PC) and carcinoma of the esophagus. Additionally, the invention includes refractory or recurrent malignancies whose growth may be inhibited using the anti-PD-L1 Abs of the invention.

Examples of other cancers that may be treated using an anti-PD-L1 Ab in the methods of the invention, based on the indications of very broad applicability of anti-PD-L1 immunotherapy provided herein, include bone cancer, skin cancer, cancer of the head or neck, breast cancer, lung cancer, cutaneous or intraocular malignant melanoma, renal cancer, uterine cancer, castration-resistant prostate cancer, colon cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, carcinomas of the ovary, gastrointestinal tract and breast, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, multiple myeloma, environmentally induced cancers including those induced by asbestos, metastatic cancers, and any combinations of said cancers. The present invention is also applicable to treatment of metastatic cancers.

Combination Therapy with Anti-PD-L1 Abs

Optionally, Abs to PD-L1 can be combined with an immunogenic agent, for example a preparation of cancerous cells, purified tumor antigens (including recombinant proteins, peptides, and carbohydrate molecules), antigen-presenting cells such as dendritic cells bearing tumor-associated antigens, and cells transfected with genes encoding immune stimulating cytokines (He et al., 2004). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF. PD-1 blockade may also be effectively combined with standard cancer treatments, including chemotherapeutic regimes, radiation, surgery, hormone deprivation and angiogenesis inhibitors, as well as another immunotherapeutic Ab (e.g., an anti-PD-1, anti-CTLA-4 or anti-LAG-3 Ab).

Uses of Anti-PD-L1 Abs

This disclosure provides the use of any anti-PD-L1 Ab or antigen-binding portion thereof of the invention for the preparation of a medicament for inhibiting signaling from the PD-1/PD-L1 pathway so as to thereby potentiate an endogenous immune response in a subject afflicted with cancer. The disclosure also provides the use of any anti-PD-L1 Ab or antigen-binding portion thereof of the invention for the preparation of a medicament for immunotherapy of a subject afflicted with cancer comprising disrupting the interaction between PD-1 and PD-L1. The disclosure provides medical uses of any anti-PD-L1 Ab or antigen-binding portion thereof of the invention corresponding to all the embodiments of the methods of treatment employing an anti-PD-L1 Ab described herein.

This disclosure also provides an anti-PD-L1 Ab or an antigen-binding portion thereof of the invention for use in potentiating an endogenous immune response in a subject afflicted with cancer by inhibiting signaling from the PD-1/PD-L1 pathway. The disclosure further provides an anti-PD-L1 Ab or an antigen-binding portion thereof of the invention for use in immunotherapy of a subject afflicted with cancer comprising disrupting the interaction between PD-1 and PD-L1. These Abs may be used in potentiating an endogenous immune response against, or in immunotherapy of, the full range of cancers disclosed herein. In preferred embodiments, the cancers include MEL (e.g., metastatic malignant MEL), RCC, squamous NSCLC, non-squamous NSCLC, CRC, ovarian cancer (OV), gastric cancer (GC), breast cancer (BC), pancreatic carcinoma (PC) and carcinoma of the esophagus.

Validation of Cancer Immunotherapy by Immune Checkpoint Blockade

A major implication of the clinical activity of immune checkpoint blockade is that significant endogenous immune responses to tumor antigens are generated and these responses may be harnessed therapeutically to mediate clinical tumor regression upon checkpoint inhibition. In fact, there is evidence that inhibitory ligands such as PD-L1 are induced in response to immune attack, a mechanism termed adaptive resistance (Gajewski et al., 2010; Taube et al., 2012). This potential mechanism of immune resistance by tumors suggests that PD-1/PD-L1-directed therapy might synergize with other treatments that enhance endogenous antitumor immunity. Follow-up studies have verified that patients continue to demonstrate tumor control after cessation of PD-1/PD-L1 pathway blockade (Lipson et al., 2013). Such tumor control may reflect a persistent antitumor immune response and the generation of effective immunologic memory to enable sustained control of tumor growth.

The data disclosed herein on the clinical testing of Abs that block the immunoregulatory receptor, PD-1, and also of Abs that block one of its cognate ligands, PD-L1, are unprecedented. These data constitute the largest clinical experience to date with PD-1 pathway-directed cancer immunotherapy, and the first report specifically describing the safety, tolerability, and initial clinical activity of an anti-PD-L1-directed agent. These findings show that both anti-PD-1 and anti-PD-L1 have favorable overall safety profiles and provide clear evidence of clinical activity across diverse cancers, including NSCLC, a tumor not historically considered responsive to immunotherapy, as well as tumors known to respond to immunotherapy, including MEL, RCC and OV. Thus, these data strongly validate the PD-1/PD-L1 pathway as an important target for therapeutic intervention in cancer.

The remarkable similarities observed between the patterns of clinical activity obtained with the anti-PD-1 and anti-PD-L1 mAbs, and among the tumor types analyzed to date, validate the general importance of the PD-1/PD-L1 signaling pathway in tumor immune resistance and as a target for therapeutic intervention. Although the molecular interactions blocked by these two Abs are not identical, it has been clearly demonstrated herein that, irrespective of mechanistic details, both anti-PD-1 and anti-PD-L1 Abs of the invention are effective in treating patients afflicted with a wide variety of cancers, including "immunogenic" cancers such as MEL and RCC as well as treatment-refractory metastatic NSCLC, a tumor that is generally not considered to be immune-responsive. In certain embodiments of the invention, either or both of these Abs can be administered in combination with another therapeutic agent such as a cytokine.

Infectious Diseases

Other methods of the invention are used to treat patients that have been exposed to particular toxins or pathogens. For example, another aspect of the disclosure provides a method of treating an infectious disease in a subject comprising administering to the subject an anti-PD1 or an anti-PD-L1 Ab, or antigen-binding portion thereof, of the invention such that the subject is treated for the infectious disease. Preferably, the Ab is a human anti-human PD-1 or PD-L1 Ab (such as any of the human Abs described herein). Alternatively, the Ab is a chimeric or humanized Ab.

Similar to its application to tumors as discussed above, Ab-mediated PD-1 or PD-L1 blockade can be used alone, or as an adjuvant, in combination with vaccines, to potentiate an immune response to pathogens, toxins, and/or self-antigens. Examples of pathogens for which this therapeutic approach may be particularly useful include pathogens for which there is currently no effective vaccine, or pathogens for which conventional vaccines are less than completely effective. These include, but are not limited to HIV, Hepatitis (A, B, and C), Influenza, Herpes, Giardia, Malaria, *Leishmania, Staphylococcus aureus, Pseudomonas aeruginosa*. PD-1 and/or PD-L1 blockade is particularly useful against established infections by agents such as HIV that present altered antigens over the course of an infection. Novel epitopes on these antigens are recognized as foreign at the time of anti-human PD-1 or PD-L1 administration, thus provoking a strong T cell response that is not dampened by negative signals through the PD-1/PD-L1 pathway.

In the above methods, PD-1 or PD-L1 blockade can be combined with other forms of immunotherapy such as cytokine treatment (e.g., administration of interferons, GM-CSF, G-CSF or IL-2).

Kits

Also within the scope of the present invention are kits, including pharmaceutical kits, comprising an anti-PD-1 and/or an anti-PD-L1 Ab of the invention for therapeutic uses, and diagnostic kits comprising an anti-PD-L1 Ab of the invention for assaying membranous PD-L1 expression as a biomarker for screening patients for immunotherapy or for predicting the efficacy of an immunotherapeutic agent. Kits typically include a label indicating the intended use of the contents of the kit and instructions for use. The term label includes any writing, or recorded material supplied on or with the kit, or which otherwise accompanies the kit. In certain embodiments of a pharmaceutical kit, the anti-PD-1 and/or anti-PD-L1 Abs may be co-packaged with other therapeutic agents in unit dosage form. In certain embodiments of a diagnostic kit, the anti-PD-L1 Ab may be co-packaged with other reagents for performing an assay to detect and/or quantify PD-L1 expression.

In certain preferred embodiments, the pharmaceutical kit comprises the anti-human PD-1 HuMAb, nivolumab. In other preferred embodiments, the pharmaceutical kit comprises the anti-human PD-L1 HuMAb, BMS-936559. In certain preferred embodiments, the diagnostic kit comprises the rabbit anti-human PD-L1 mAb, 28-8, comprising the $V_H$ and $V_K$ regions whose amino acid sequences are set forth in SEQ ID NOs. 35 and 36, respectively. In other preferred embodiments, the diagnostic kit comprises the murine anti-human PD-L1 mAb, 5H1 (Dong et al., 2002).

PD-L1 Biomarker for Predicting Anti-PD-1 Efficacy

A particular challenge in cancer immunotherapy has been the identification of mechanism-based predictive biomarkers to enable patient selection and guide on-treatment management. Data disclosed in the Examples below indicate that cell surface PD-L1 expression in tumors is a useful molecular marker for predicting the efficacy of, and selecting patients for, anti-PD-1 immunotherapy.

There are conflicting reports in the literature about the clinical implications of PD-L1 being expressed in tumors. Several studies have concluded that PD-L1 expression in tumors correlates with a poor prognosis for the patient. See, e.g., Hino et al., 2010 (MEL); Hamanishi et al., 2007 (OV); Thompson et al., 2006 (RCC). These findings may be rationalized on the basis that the interaction of PD-L1 on tumor cells and PD-1 on T cells helps abrogate immune responses directed against the tumor, resulting in immune evasion from tumor-specific T cells. However, in contrast to the foregoing studies, Gadiot et al., 2011 and Taube et al., 2012 have recently reported that PD-L1 expression in melanoma tumors correlates with a trend toward better survival. These seemingly contradictory data may reflect the relatively small numbers of patients analyzed, different histologic subtypes studied, or different methodologies used, e.g., the use of different Abs to stain PD-L1, the use of frozen versus paraffin-embedded material for IHC, and the detection of membranous and/or cytoplasmic staining of PD-L1. Taube et al., 2012 note that PD-L1 is a type I transmembrane molecule, and hypothesize that while the cytoplasmic presence of PD-L1 may represent intracellular stores of this polypeptide that may be deployed to the cell surface upon appropriate stimulation, it is cell surface PD-L1 expression of that is biologically relevant as a potential biomarker for predicting clinical response to PD-1 blockade. See, also, Brahmer et al., 2010, which describes preliminary evidence, obtained on a small sample size of only 9 patients, of a correlation between membranous PD-L1 expression and anti-PD-1 efficacy. The data described in the Examples below on the use of membranous PD-L1 expression as a biomarker for anti-PD-1 efficacy, which was obtained from analysis of a much larger sample, substantiate the hypothesis that PD-L1 expression may be used as a biomarker for predicting anti-PD-1 clinical response and for screening patients to identify suitable candidates for immunotherapy with an anti-PD-1 Ab or other inhibitors of inhibitory immunoregulators.

Specifically, membranous PD-L1 expression was assayed using an automated IHC protocol and a rabbit anti-hPD-L1 Ab. Strikingly, in the initial set of data analyzed (see Example 8), no patients with cell surface PD-L1-negative tumors (MEL, NSCLC, CRC, RCC and CRPC) experienced an OR following treatment with the anti-PD-1 Ab, nivolumab. In contrast, cell surface expression of PD-L1 on tumor cells in pretreatment biopsies may be associated with an increased rate of OR among patients treated with nivolumab. While tumor cell expression of PD-L1 may be driven by constitutive oncogenic pathways, it may also reflect "adaptive immune resistance" in response to an endogenous antitumor immune response, part of a host inflammatory response, which may remain in check unless unleashed by blockade of the PD-1/PD-L1 pathway (Taube et al., 2012). This emerging concept of adaptive immune resistance in cancer immunology suggests that inhibitory ligands such as PD-L1 are induced in response to immune attack (Gajewski et al., 2010; Taube et al., 2012). A major implication of the clinical activity of immune checkpoint blockade as described herein is that significant endogenous immune responses to tumor antigens are generated and these responses may be harnessed therapeutically to mediate clinical tumor regression upon checkpoint inhibition. This potential mechanism of immune resistance by tumors suggests that PD-1/PD-L1-directed therapy might synergize with other treatments that enhance endogenous antitumor immunity. It also suggests that cell surface expression of PD-L1 in tumors and/or inflammatory cells in the tumor microenvironment may be a marker not just for treatment of cancer patients with an anti-PD-1 Ab, but also for treatment with an anti-PD-L1 Ab as well as treatments targeting inhibitory immunoregulatory pathways other than the PD-1/PD-L1 pathway.

Assaying Cell-Surface PD-L1 Expression by Automated IHC

As described in the Examples, an automated IHC method was developed for assaying the expression of PD-L1 on the surface of cells in FFPE tissue specimens. The disclosure provides methods for detecting the presence of human PD-L1 antigen in a test tissue sample, or quantifying the level of human PD-L1 antigen or the proportion of cells in the sample that express the antigen, which methods comprise contacting the test sample, and a negative control sample, with a mAb that specifically binds to human PD-L1, under conditions that allow for formation of a complex between the Ab or portion thereof and human PD-L1. Preferably, the test and control tissue samples are FFPE samples. The formation of a complex is then detected, wherein a difference in complex formation between the test sample and the negative control sample is indicative of the presence of human PD-L1 antigen in the sample. Various methods are used to quantify PD-L1 expression.

In a particular embodiment, the automated IHC method comprises: (a) deparaffinizing and rehydrating mounted tissue sections in an autostainer; (b) retrieving antigen using a decloaking chamber and pH 6 buffer, heated to 110° C. for 10 min; (c) setting up reagents on an autostainer; and (d) running the autostainer to include steps of neutralizing endogenous peroxidase in the tissue specimen; blocking non-specific protein-binding sites on the slides; incubating the slides with primary Ab; incubating with a post-primary blocking agent; incubating with NovoLink Polymer; adding a chromogen substrate and developing; and counterstaining with hematoxylin.

For assessing PD-L1 expression in tumor tissue samples, a pathologist examines the number of membrane PD-L1$^+$ tumor cells in each field under a microscope and mentally estimates the percentage of cells that are positive, then averages them to come to the final percentage. The different staining intensities are defined as 0/negative, 1+/weak, 2+/moderate, and 3+/strong. Typically, percentage values are first assigned to the 0 and 3+ buckets, and then the intermediate 1+ and 2+ intensities are considered. For highly heterogeneous tissues, the specimen is divided into zones, and each zone is scored separately and then combined into a single set of percentage values. The percentages of negative and positive cells for the different staining intensities are determined from each area and a median value is given to each zone. A final percentage value is given to the tissue for each staining intensity category: negative, 1+, 2+, and 3+. The sum of all staining intensities needs to be 100%.

Staining is also assessed in tumor-infiltrating inflammatory cells such as macrophages and lymphocytes. In most cases macrophages serve as an internal positive control since staining is observed in a large proportion of macrophages. While not required to stain with 3+ intensity, an absence of staining of macrophages should be taken into account to rule out any technical failure. Macrophages and lymphocytes are assessed for plasma membrane staining and only recorded for all samples as being positive or negative for each cell category. Staining is also characterized according to an outside/inside tumor immune cell designation. "Inside" means the immune cell is within the tumor tissue and/or on the boundaries of the tumor region without being physically intercalated among the tumor cells. "Outside" means that there is no physical association with the tumor, the immune cells being found in the periphery associated with connective or any associated adjacent tissue.

In certain embodiments of these scoring methods, the samples are scored by two pathologists operating independently and the scores are subsequently consolidated. In certain other embodiments, the identification of positive and negative cells is scored using appropriate software.

A histoscore is used as a more quantitative measure of the IHC data. The histoscore is calculated as follows:

$$\text{Histoscore} = [(\% \text{ tumor} \times 1(\text{low intensity})) + (\% \text{ tumor} \times 2(\text{medium intensity})) + (\% \text{ tumor} \times 3(\text{high intensity}))]$$

To determine the histoscore, the pathologist estimates the percentage of stained cells in each intensity category within a specimen. Because expression of most biomarkers is heterogeneous the histoscore is a truer representation of the overall expression. The final histoscore range is 0 (no expression) to 300 (maximum expression).

An alternative means of quantifying PD-L1 expression in a test tissue sample IHC is to determine the adjusted inflammation score (AIS) score defined as the density of inflammation multiplied by the percent PD-L1 expression by tumor-infiltrating inflammatory cells (Taube et al., 2012).

Cancer Immunotherapy with Anti-PD-1 Comprising a Patient Selection Step

This disclosure also provides a method for immunotherapy of a subject afflicted with cancer, which method comprises: (a) selecting a subject that is a suitable candidate for immunotherapy, the selecting comprising (i) optionally providing a test tissue sample obtained from a patient with cancer of the tissue, the test tissue sample comprising tumor cells and tumor-infiltrating inflammatory cells, (ii) assessing the proportion of cells in the test tissue sample that express PD-L1 on the cell surface, and (iii) selecting the subject as a suitable candidate based on an assessment that the proportion of cells in the test tissue sample that express PD-L1 on the cell surface exceeds a predetermined threshold level; and (b) administering to the selected subject a composition comprising a therapeutically effective amount of an agent that inhibits signaling from an inhibitory immunoregulator.

There is evidence that membranous PD-L1 expression is a surrogate for an endogenous antitumor immune response that is part of a host inflammatory response (Gajewski et al., 2010; Taube et al., 2012). Accordingly, cell surface expression of PD-L1 in tumors and/or tumor-infiltrating inflammatory cells is a marker not just for selecting cancer patients who would benefit from treatment with an anti-PD-1 Ab, but also for treatment with an anti-PD-L1 Ab as well as treatments targeting inhibitory immunoregulatory pathways other than the PD-1/PD-L1 pathway. For example, cell surface expression of PD-L1 in tumors and/or tumor-infiltrating inflammatory cells may be used as a marker for identifying or selecting suitable cancer patients who would benefit from immunotherapy with agents, including Abs, that target, and disrupt or inhibit signaling from, inhibitory immunoregulators such as PD-L1, Cytotoxic T-Lymphocyte Antigen-4 (CTLA-4), B and T Lymphocyte Attenuator (BTLA), T cell Immunoglobulin and Mucin domain-3 (TIM-3), Lymphocyte Activation Gene-3 (LAG-3), Killer cell Lectin-like Receptor G1 (KLRG-1), Natural Killer Cell Receptor 2B4 (CD244), and CD160 (Baitsch et al., 2012). In certain preferred embodiments, the inhibitory immunoregulator is a component of the PD-1/PD-L1 signaling pathway. In other preferred embodiments, the inhibitory immunoregulator is an anti-PD-1 Ab of the invention. In yet other preferred embodiments, the inhibitory immunoregulator is an anti-PD-L1 Ab of the invention.

Although many of the immunotherapy methods below comprising assaying PD-L1 expression, i.e., employing a PD-L1 expression biomarker, are described as comprising the selection of a patient that is, or is not, suitable for anti-PD-1 immunotherapy or as comprising the administration of an anti-PD-1 Ab for immunotherapeutic purposes, it should be understood that these methods apply generally to the selection of a patient that is, or is not, suitable for immunotherapy with, or to the administration of an inhibitor of an inhibitory immunoregulator or a component or ligand thereof. Further, in any the methods comprising the measurement of PD-L1 expression in a test tissue sample, it should be understood that the step comprising the provision of a test tissue sample obtained from a patient is an optional step. That is, in certain embodiments the method includes this step, and in other embodiments, this step is not included in the method. It should also be understood that in certain preferred embodiments the "assessing" step to identify, or determine the number or proportion of, cells in the test tissue sample that express PD-L1 on the cell surface is performed by a transformative method of assaying for PD-L1 expression, for example by performing a reverse transcriptase-polymerase chain reaction (RT-PCR) assay or an IHC assay. In certain other embodiments, no transformative step is involved and PD-L1 expression is assessed by, for example, reviewing a report of test results from a laboratory. In certain embodiments, the steps of the methods up to, and including, assessing PD-L1 expression provides an intermediate result that may be provided to a physician or other medical practitioner for use in selecting a suitable candidate for immunotherapy and/or administering an immunotherapeutic agent to the patient. In certain embodiments, the steps that provide the intermediate result may be performed by a medical practitioner or someone acting under the direction of a medical practitioner. In other embodiment, these steps are performed by an independent person or laboratory.

The disclosure further provides a method for treatment of a subject afflicted with cancer, which method comprises: (a) selecting a subject that is not suitable for treatment with an agent that inhibits an inhibitory immunoregulator, e.g., anti-PD-1 Ab immunotherapy, the selecting comprising (i) optionally providing a test tissue sample obtained from a patient with cancer of the tissue, the test tissue sample comprising tumor cells and tumor-infiltrating inflammatory cells; (ii) assessing the proportion of cells in the test tissue sample that express PD-L1 on the surface of the cells; and (iii) selecting the subject as not suitable for immunotherapy with an inhibitor of an inhibitory immunoregulator, e.g., an anti-PD-1 Ab, based on an assessment that the proportion of cells in the test tissue sample that express PD-L1 on the cell surface is less than a predetermined threshold level; and (b) administering a standard-of-care therapeutic other than an inhibitor of an inhibitory immunoregulator, e.g., an anti-PD-1 Ab, to the selected subject.

Measurement of PD-L1 Expression

In certain embodiments of any of the present methods, the proportion of cells that express PD-L1 is assessed by performing an assay to determine the presence of PD-L1 RNA. In further embodiments, the presence of PD-L1 RNA is determined by RT-PCR, in situ hybridization or RNase protection. In other embodiments, the proportion of cells that express PD-L1 is assessed by performing an assay to determine the presence of PD-L1 polypeptide. In further embodiments, the presence of PD-L1 polypeptide is determined by immunohistochemistry (IHC), enzyme-linked immunosorbent assay (ELISA), in vivo imaging, or flow cytometry. In preferred embodiments, PD-L1 expression is assayed by IHC. Flow cytometry may be particularly suitable for assaying PD-L1 expression in cells of hematologic tumors. In preferred embodiments of all of these methods, cell surface expression of PD-L1 is assayed using, e.g., IHC or in vivo imaging.

Imaging techniques have provided important tools in cancer research and treatment. Recent developments in molecular imaging systems, including positron emission tomography (PET), single-photon emission computed tomography (SPECT), fluorescence reflectance imaging (FRI), fluorescence-mediated tomography (FMT), bioluminescence imaging (BLI), laser-scanning confocal microscopy (LSCM) and multiphoton microscopy (MPM), will likely herald even greater use of these techniques in cancer research. Some of these molecular imaging systems allow clinicians to not only see where a tumor is located in the body, but also to visualize the expression and activity of specific molecules, cells, and biological processes that influence tumor behavior and/or responsiveness to therapeutic drugs (Condeelis et al., 2010). Ab specificity, coupled with the sensitivity and resolution of PET, makes immunoPET imaging particularly attractive for monitoring and assaying expression of antigens in tissue samples (McCabe et al., 2010; Olafsen et al., 2010). In certain embodiments of any of the present methods, PD-L1 expression is assayed by immunoPET imaging.

In certain embodiments of any of the present methods, the proportion of cells in a test tissue sample that express PD-L1 is assessed by performing an assay to determine the presence of PD-L1 polypeptide on the surface of cells in the test tissue sample. In certain embodiments, the test tissue sample is a FFPE tissue sample. In certain preferred embodiments, the presence of PD-L1 polypeptide is determined by IHC assay. In further embodiments, the IHC assay is performed using an automated process. In further embodiments, the IHC assay is performed using an anti-PD-L1 mAb to bind to the PD-L1 polypeptide.

Abs that Bind Specifically to Cell-Surface-Expressed PD-L1 in FFPE Tissues

An Ab may bind to an antigen in fresh tissues but completely fail to recognize the antigen in an FFPE tissue sample. This phenomenon, well known in the art, is thought to be due primarily to intra- and inter-molecular cross-linking of polypeptides induced by formalin fixation, which alters the epitope recognized by the Ab (Sompuram et al., 2006). In addition, several factors known to influence staining in FFPE tissue, including variable time to fixation, inadequate fixation period, differences in fixative used, tissue processing, Ab clone and dilution, antigen retrieval, detection system, and interpretation of results using different threshold points are important variables that can affect tissue antigenicity and IHC measurements (Bordeaux et al., 2010). In particular, a lack of anti-human PD-L1 Abs that stain PD-L1 in FFPE specimens has been noted in the art (Hamanishi et al., 2007). Thus, the contradictory results reported by different groups on the implications of PD-L1 expression for prognosis of a tumor may, in part, reflect the differential abilities of anti-PD-L1 Abs used to detect PD-L1 polypeptide in FFPE tissue samples. Indeed, our analysis of five commercially available anti-hPD-L1 Abs shows that these Abs failed to distinguish FFPE cells expressing PD-L1 from cells that did not express PD-L1 (see Example 9, Table 6). Accordingly, in order to detect hPD-L1 on the surface of cells using an IHC assay on FFPE tissues, there is a need for anti-hPD-L1 Abs that bind specifically to cell surface-expressed PD-L1 in FFPE tissue samples.

This disclosure provides a mAb or an antigen-binding portion thereof that binds specifically to a cell surface-expressed PD-L1 antigen in a FFPE tissue sample. In preferred embodiments, the mAb or antigen-binding portion thereof does not bind to a cytoplasmic PD-L1 polypeptide in the FFPE tissue sample or exhibits a very low level of background binding. In certain other embodiments, the presence or absence of binding specifically to a cell surface-expressed or a cytoplasmic PD-L1 polypeptide is detected by immunohistochemical staining. In certain preferred aspects of the invention, the mAb or antigen-binding portion is a rabbit Ab or a portion thereof. In other preferred embodiments, the mAb is the rabbit mAb designated 28-8, 28-1, 28-12, 29-8 or 20-12. In more preferred embodiments, the mAb is the rabbit mAb designated 28-8 or an antigen-binding portion thereof. In further embodiments, the mAb is an Ab comprising a heavy chain variable region ($V_H$) comprising consecutively linked amino acids having the sequence set forth in SEQ ID NO: 35 and a light chain variable region ($V_K$) comprising consecutively linked amino acids having the sequence set forth in SEQ ID NO: 36. In other embodiments, the mAb comprises the CDR1, CDR2 and CDR3 domains in a $V_H$ having the sequence set forth in SEQ ID NO: 35, and the CDR1, CDR2 and CDR3 domains in a $V_K$ having the sequence set forth in SEQ ID NO: 36.

It is known in the art that rabbit Abs have certain advantages over murine Abs. For example, rabbit Abs generally exhibit more diverse epitope recognition, improved immune response to small-size epitopes, and higher specificity and affinity compared to murine Abs (see, e.g., Fischer et al., 2008; Cheang et al., 2006; Rossi et al., 2005). For example, the rabbit's lower immune dominance and larger B-cell repertoire results in greater epitope recognition compared to murine Abs. Further, the high specificity and novel epitope recognition of rabbit antibodies translates to success with recognition of post-translational modifications (Epitomics, 2013). In addition, many protein targets relevant to signal transduction and disease are highly conserved between mice, rats and humans, and can therefore be recognized as self-antigens by a mouse or rat host, making them less immunogenic. This problem is avoided by generating Abs in rabbits. In addition, in applications in which two antigen-specific Abs are required, it is more convenient to have the Abs come from two different species. Thus, for example, it is easier to multiplex a rabbit Ab such as 28-8 with other Abs (likely to be murine Abs since the best immune marking Abs are murine Abs) that can mark immune cells that also express PD-L1 (e.g., macrophages and lymphocytes). Thus, rabbit anti-hPD-L1 mAbs, e.g., 28-8, are particularly suited to IHC assays for detecting surface-expressed PD-L1 in FFPE tissue samples and have distinct advantages over murine Abs, such as 5H1.

As described in Example 9, a large number (185) of antibody multiclones from both rabbit and mouse immunizations were screened, and only ten rabbit Ab, but no mouse Ab, multiclones specifically detected the membranous form of hPD-L1. After further extensive screening by multiple rounds of IHC, 15 purified rabbit subclones were selected based on their specificity and intensity of staining (see Table 4). Following further characterization of the antibodies to determine their binding affinity and cross-competition by surface plasmon resonance, as well as screening by IHC on FFPE tissues, mAb 28-8 was selected as the Ab with the best combination of binding to membranous PDF-L1 with high affinity and specificity, and low background staining.

In certain aspects of this invention, the mAb or antigen-binding portion cross-competes with mouse mAb 5H1 for binding to PD-L1, which indicates that these antibodies bind to the same epitope region of PD-L1. In certain other aspects, the mAb or antigen-binding portion thereof does not cross-compete with mouse mAb 5H1 for binding to PD-L1, indicating that they do not bind to the same epitope region of PD-L1.

The disclosure also provides nucleic acids encoding all of the rabbit anti-hPD-L1 Abs or portions thereof disclosed herein.

Immunotherapeutic Methods Comprising Measurement of Cell Surface PD-L1 Expression The availability of rabbit Abs that bind with high affinity specifically to membranous PD-L1 in FFPE tissue specimens facilitates methods comprising a step of detecting PD-L1 polypeptide on the surface of cells in FFPE tissue samples. Accordingly, this disclosure also provides a method for immunotherapy of a subject afflicted with cancer, which method comprises: (a) selecting a subject that is a suitable candidate for immunotherapy, the selecting comprising: (i) optionally providing a FFPE test tissue sample obtained from a patient with cancer of the tissue, the test tissue sample comprising tumor cells and tumor-infiltrating inflammatory cells; (ii) assessing the proportion of cells in the test tissue sample that express PD-L1 on the cell surface by IHC using a rabbit anti-human PD-L1 Ab, e.g., mAb 28-8, to bind to the PD-L1; and (iii) selecting the subject as a suitable candidate based on an assessment that the proportion of cells in the test tissue sample that express PD-L1 on the cell surface exceeds a predetermined threshold level; and (b) administering a composition comprising a therapeutically effective amount of an anti-PD-1 Ab to the selected subject.

In certain embodiments of methods employing IHC to assay PD-L1 expression in FFPE tissues, an automated IHC assay is used. The automated IHC process is performed on an autostainer and comprises: (a) de-paraffinizing the FFPE sample with xylene and rehydrating the sample; (b) retrieving the antigen using a decloaking chamber; (c) blocking nonspecifc protein binding sites by incubation with a Protein Block; (d) incubating the sample with a primary anti-PD-L1 Ab; (e) adding a polymeric horseradish peroxidase (HRP)-conjugated secondary Ab; (f) detecting the bound secondary Ab comprising staining with a 3,3'-diaminobenzidine (DAB) chromogen; and/or (g) counterstaining with hematoxylin. This automated IHC process has been optimized by minimization of the number of steps, optimization of incubation times, and selection of primary Abs, blocking and detection reagents that produce strong specific staining with a low level of background staining. In preferred embodiments of this automated IHC assay, the primary anti-PD-L1 Ab is rabbit mAb 28-8 or murine mAb 5H1. In certain embodiments of this invention, this IHC assay, and any other IHC assay described herein to measure PD-L1 expression, may be used as part of a method of immunotherapy. In other embodiments, any of the IHC methods described herein is used independently of any therapeutic process requiring the administration of a therapeutic, i.e., solely as a diagnostic method to assay PD-L1 expression.

In certain embodiments any of the immunotherapy methods described herein, the Ab administered to the selected subject is any anti-PD-1 or anti-PD-L1 Ab or antigen-binding portion thereof of the invention. In certain preferred embodiments, the subject is a human. In other preferred embodiments, the Ab is a human Ab or antigen-binding portion thereof. In more preferred embodiments, the anti-PD-1 Ab is nivolumab and the anti-PD-L1 Ab is BMS-936559. In certain other embodiments, the anti-PD-1 Ab is an Ab or antigen-binding portion thereof that cross-competes with nivolumab for binding to PD-1, and the anti-PD-L1 Ab is an Ab or antigen-binding portion thereof that cross-competes with BMS-936559 for binding to PD-L1. In certain preferred embodiments, the cancer to be treated is selected from the group consisting MEL, RCC, squamous NSCLC, non-squamous NSCLC, CRC, castration-resistant prostate cancer CRPC, HCC, squamous cell carcinoma of the head and neck, carcinomas of the esophagus, ovary, gastrointestinal tract and breast, and a hematological malignancy.

In certain embodiments of the disclosed methods, the predetermined threshold is based on a proportion of (a) tumor cells, (b) tumor-infiltrating inflammatory cells, (c) particular tumor-infiltrating inflammatory cells, e.g., TILs or macrophages, or (d) a combination of tumor cells and tumor-infiltrating inflammatory cells, in a test tissue sample that expresses PD-L1 on the cell surface. In certain embodiments, the predetermined threshold is at least 0.001% of tumor cells expressing membranous PD-L1 as determined by IHC. In other embodiments, the predetermined threshold is at least 0.01%, preferably at least 0.1%, more preferably at least 1% of tumor cells expressing membranous PD-L1, as determined by IHC. In certain embodiments, the predetermined threshold is at least 5% of tumor cells expressing membranous PD-L1 as determined by IHC. In certain embodiments, the predetermined threshold is at least 0.01%, at least 0.1%, at least 1%, or at least 5% of tumor cells expressing membranous PD-L1 as determined by IHC, and/or a single tumor-infiltrating inflammatory cell expressing membranous PD-L1 as determined by IHC. In certain other embodiments, the predetermined threshold is at least 0.01%, at least 0.1%, at least 1%, or at least 5% of a tumor-infiltrating inflammatory cell expressing membranous PD-L1 as determined by IHC. In certain other embodiments, the predetermined threshold is at least 0.01%, at least 0.1%, at least 1%, or at least 5% of a tumor-infiltrating lymphocyte expressing membranous PD-L1 as determined by IHC. In certain other embodiments, the predetermined threshold is at least 0.01%, at least 0.1%, at least 1%, or at least 5% of a tumor-infiltrating macrophage expressing membranous PD-L1 as determined by IHC. In yet other embodiments, the predetermined threshold is at least a single tumor cell or a single tumor-infiltrating inflammatory cell expressing membranous PD-L1 as determined by IHC. Preferably, PD-L1 expression is assayed by automated IHC using mAb 28-8 or 5H1 as the primary Ab.

This disclosure also provides a method for treatment of a subject afflicted with cancer, which method comprises: (a) screening a plurality of subjects to identify a subject that is not a suitable candidate for immunotherapy comprising the administration of an anti-PD-1 Ab to the subject, the screening comprising: (i) optionally providing test tissue samples from the plurality of subjects, the test tissue samples comprising tumor cells and tumor-infiltrating inflammatory cells; (ii) assessing the proportion of cells in the test tissue samples that express PD-L1 on the surface of the cells; and (iii) selecting the subject as a candidate that is not suitable for anti-PD-1 Ab immunotherapy based on an assessment that the proportion of cells that express PD-L1 on the surface of cells in the subject's test tissue sample is below a predetermined threshold level; and (b) administering a standard-of-care therapeutic other than an anti-PD-1 Ab to the selected subject.

This disclosure also provides a method for immunotherapy of a subject afflicted with cancer, which method comprises: (a) screening a plurality of subjects to identify a subject that is a suitable candidate for immunotherapy, the screening comprising: (i) optionally providing test tissue samples from the plurality of subjects, the test tissue samples comprising tumor cells and tumor-infiltrating inflammatory cells; (ii) assessing the proportion of cells in the test tissue samples that express PD-L1 on the surface of the cells; and (iii) selecting the subject as a candidate that is suitable for anti-PD-1 Ab immunotherapy based on an assessment that the proportion of cells in the test tissue sample that express PD-L1 on the cell surface exceeds a predetermined threshold level; and (b) administering a composition comprising a therapeutically effective amount of an anti-PD-1 Ab to the selected subject.

This disclosure further provides a method for treatment of a subject afflicted with cancer, which method comprises: (a) screening a plurality of subjects to identify a subject that is a suitable candidate for the treatment, the screening comprising: (i) optionally providing test tissue samples from the plurality of subjects, the test tissue samples comprising tumor cells and tumor-infiltrating inflammatory cells; (ii) assessing the proportion of cells in the test tissue samples that express PD-L1 on the surface of the cells, wherein the subject is identified as a suitable candidate for anti-PD-1 Ab immunotherapy if the proportion of cells in the tissue sample that express PD-L1 on the cell surface exceeds a predetermined threshold level, and the subject is identified as a candidate that is not a suitable candidate for anti-PD-1 Ab immunotherapy if the proportion of cells in the tissue sample that express PD-L1 on the cell surface is below a predetermined threshold level; and (b) administering a composition comprising a therapeutically effective amount of an anti-PD-1 Ab to the subject identified as a suitable candidate for anti-PD-1 Ab immunotherapy, or (c) administering a standard-of-care therapeutic other than an anti-PD-1 Ab to the subject identified as not a suitable candidate for anti-PD-1 Ab immunotherapy.

One aspect of this invention is a method for immunotherapy of a subject afflicted with cancer, which method comprises: (a) optionally providing a test tissue sample obtained from a patient with cancer of the tissue, the test tissue sample comprising tumor cells and tumor-infiltrating inflammatory cells; (b) determining that a proportion of cells in the test tissue sample express PD-L1 above a predetermined threshold level on the cell surface; and (c) based on that determination administering a composition comprising a therapeutically effective amount of an anti-PD-1 Ab to the subject. Another aspect of the invention is a method for treatment of a subject afflicted with cancer, which method comprises: (a) optionally providing a test tissue sample obtained from a patient with cancer of the tissue, the test tissue sample comprising tumor cells and tumor-infiltrating inflammatory cells; (b) determining that the proportion of cells in the test tissue sample that express PD-L1 on the cell surface is below a predetermined threshold level; and (c) based on that determination administering a standard-of-care therapeutic other than an anti-PD-1 Ab to the subject.

Yet another aspect of the invention is a method for immunotherapy of a subject afflicted with cancer, which method comprises: (a) optionally providing a test tissue sample obtained from a patient with cancer of the tissue, the test tissue sample comprising tumor cells and tumor-infiltrating inflammatory cells; (b) determining that cells in the test tissue sample express PD-L1 on the cell surface; (c) selecting an anti-PD-1 Ab as a treatment for the subject based on the recognition that an anti-PD-1 Ab is effective in patients whose test tissue sample contains a proportion of cells above a predetermined threshold level that express PD-L1 on the cell surface; and (d) administering a composition comprising a therapeutically effective amount of an anti-PD-1 Ab to the subject. In a further aspect, the disclosure provides a method for treatment of a subject afflicted with cancer, which method comprises: (a) optionally providing a test tissue sample obtained from a patient with cancer of the tissue, the test tissue sample comprising tumor cells and tumor-infiltrating inflammatory cells; (b) determining that cells in the test tissue sample do not express PD-L1 on the cell surface; (c) selecting a standard-of-care therapeutic other than an anti-PD-1 Ab as a treatment for the subject based on the recognition that an anti-PD-1 Ab is ineffective in patients whose test tissue sample contains a proportion of cells that express PD-L1 on the cell surface is below a predetermined threshold level; and (d) administering the standard-of-care therapeutic to the subject.

This disclosure also provides a method of selecting an immunotherapy for a subject afflicted with cancer, which method comprises: (a) assaying cells of a test tissue sample comprising tumor cells and tumor-infiltrating inflammatory cells to assess the proportion of cells in the test tissue sample that express PD-L1; and (b) based on an assessment that the proportion of cells that express membranous PD-L1 is above a predetermined threshold level, selecting an immunotherapy comprising a therapeutically effective amount of an anti-PD-1 Ab for the subject. The disclosure further provides a method of selecting a treatment for a subject afflicted with cancer, which method comprises: (a) assaying cells of a test tissue sample comprising tumor cells and tumor-infiltrating inflammatory cells to assess the proportion of cells in the test tissue sample that express PD-L1; and (b) based on an assessment that the proportion of cells that express membranous PD-L1 is below a predetermined threshold level, selecting a standard-of-care treatment other than an anti-PD-1 Ab for the subject.

In addition, the disclosure provides a method for treatment of a subject afflicted with cancer, which method comprises administering to the subject a composition comprising a therapeutically effective amount of an anti-PD-1 Ab, the subject having been selected on the basis that the proportion of cells in a test tissue sample from the subject that express PD-L1 is determined to exceed a predetermined threshold level, wherein the test tissue sample comprises tumor cells and tumor-infiltrating inflammatory cells. This disclosure also provides a method for treatment of a subject afflicted with cancer, which method comprises administering to the subject a standard-of-care treatment other than an anti-PD-1 Ab, the subject having been selected on the basis that the proportion of cells in a test tissue sample from the subject that express PD-L1 is determined to be below a predetermined threshold level, wherein the test tissue sample comprises tumor cells and tumor-infiltrating inflammatory cells.

This disclosure further provides a method for selecting a cancer patient for immunotherapy with an anti-PD-1 Ab, which method comprises: (a) optionally providing a test tissue sample obtained from a patient with cancer of the tissue, the test tissue sample comprising tumor cells and tumor-infiltrating inflammatory cells; (b) assaying the test tissue sample to determine the proportion of cells therein that express PD-L1 on the cell surface; (c) comparing the proportion of cells that express PD-L1 on the cell surface with a predetermined threshold proportion; and (d) selecting the patient for immunotherapy based on an assessment that the proportion of cells in the test tissue sample that express surface PD-L1 is above the predetermined threshold level. In any of the methods described herein comprising a step for assessing PD-L1 expression, the test tissue sample may be a FFPE tissue sample.

In addition, in any method where an immunotherapy is selected or administered based on an assessment that the proportion of cells in a test tissue sample from the subject expresses PD-L1 at a level above a predetermined threshold level, it follows that a complementary method of treatment may be performed wherein a standard-of-care treatment other than the immunotherapy is selected or administered based on an assessment that the proportion of cells in a test tissue sample from the subject expresses PD-L1 at a level below the predetermined threshold level.

This disclosure further provides a method for predicting the therapeutic effectiveness of an anti-PD-1 Ab for treating a cancer patient, which method comprises: (a) optionally providing a test tissue sample obtained from a patient with cancer of the tissue, the test tissue sample comprising tumor cells and tumor-infiltrating inflammatory cells; (b) assaying the test tissue sample to determine the proportion of cells therein that express PD-L1 on the cell surface; (c) comparing the proportion of cells that express PD-L1 on the cell surface with a predetermined threshold value; and (d) predicting the therapeutic effectiveness of the anti-PD-1 Ab, wherein if the proportion of cells that express PD-L1 on the cell surface exceeds the threshold proportion the Ab is predicted to be effective in treating the patient, and wherein if the proportion of cells that express PD-L1 on the cell surface is below the threshold proportion the Ab is predicted to not be effective in treating the patient.

This disclosure also provides a method for determining an immunotherapeutic regimen comprising an anti-PD-1 Ab for treating a cancer patient, which method comprises: (a) optionally providing a test tissue sample obtained from a patient with cancer of the tissue, the test tissue sample comprising tumor cells and tumor-infiltrating inflammatory cells; (b) assaying the test tissue sample to determine the proportion of cells therein that express PD-L1 on the cell surface; (c) comparing the proportion of cells that express PD-L1 on the cell surface with a predetermined threshold proportion; and (d) determining an immunotherapeutic regimen comprising an anti-PD-1 Ab based on the determination that the proportion of cells that express PD-L1 on the cell surface exceeds the predetermined threshold proportion.

Standard-of-Care Therapeutics

Several of the methods of treatment described herein comprise the administration of a standard-of-care therapeutic to a patient. As used herein, a "standard-of-care therapeutic" is a treatment process, including a drug or combination of drugs, radiation therapy, surgery or other medical intervention that is recognized by medical practitioners as appropriate, accepted, and/or widely used for a certain type of patient, disease or clinical circumstance. Standard-of-care therapeutics for treating different types of cancer are well known by persons of skill in the art. For example, the National Comprehensive Cancer Network (NCCN), an alliance of 21 major cancer centers in the USA, publishes the NCCN Clinical Practice Guidelines in Oncology (NCCN GUIDELINES®) that provide detailed up-to-date information on the standard-of-care treatments for a wide variety of cancers (see NCCN GUIDELINES®, 2013). By way of example, standard-of-care treatments for MEL, RCC and NSCLC are summarized below.

Melanoma

For in situ or early-stage MEL, surgical treatment is the primary treatment. Where surgical excision is not feasible for in situ melanoma due to comorbidity or cosmetically sensitive tumor location, topical imiquimod and radiotherapy are emerging as treatments, especially for lentigo maligna. Chemotherapeutic agents for treating MEL include dacarbazine, temozolomide, imatinib for melanoma with c-KIT mutation, high-dose interleukin-2, and paclitaxel with or without carboplatin. However, these treatments have modest success, with response rates below 20% in first-line (1 L) and second-line (2 L) settings.

There is no consensus on the best treatments for metastatic melanoma, though a variety of treatments including excision to clear margins, intralesional injections, laser ablation, radiation and biochemotherapy (combination of chemotherapy and biological agents such as interferon-alpha and IL-2) are being investigated. The therapeutic landscape for metastatic melanoma has recently seen dramatic improvements with the development of novel drugs such as vemurafenib and ipilimumab. Vemurafenib specifically inhibits signaling by a mutated intracellular kinase, BRAF, that is present in about 50% of patients with metastatic melanoma (Flaherty et al., 2010). Ipilimumab is a HuMAb that inhibits the immune checkpoint receptor, CTLA-4, and thereby stimulates a T cell immune response (Hodi et al., 2010). Besides these two agents, no other agent has demonstrated an OS benefit in a Phase 3 randomized study. Dacarbazine is approved by the FDA and the EMA for treatment of metastatic MEL with a reported objective response rate of 5% to 20% and a median OS of 6.4 months, but these responses are short-lived. Other drugs such as temozolomide and fotemustine have not resulted in significant improvement in survival when compared to dacarbazine. IL-2 has also been approved by the FDA for the treatment of metastatic MEL as it is associated with a 15 to 20% response rate including 4-6% complete responses which can be durable, but it is associated with significant toxicities including hypotension, cardiac arrhythmias, and pulmonary edema. Further details on standard-of-care treatments for melanoma are provided by Garbe et al., 2012. Despite the recent approval of ipilimumab and vemurafenib for advanced MEL, there is still a large unmet need for patients who have progressed on anti-CTLA-4 therapy and a BRAF inhibitor (depending on BRAF status) or patients with previously untreated, unresectable or metastatic BRAF wild-type MEL. The 5-year survival rate for late-stage MEL is currently only 15%.

Renal Cell Carcinoma

For clinically localized RCC (Stage IA and IB), surgical resection, including radical nephrectomy and nephron-sparing surgery, is an effective therapy. Partial nephrectomy is generally not suitable for patients with locally advanced tumors (Stage II and III), in which case radical nephrectomy is preferred. Patients with Stage IV disease may also benefit from surgery, and cytoreductive nephrectomy before systemic therapy is recommended for patients with a potentially surgically resectable primary and multiple resectable metastases.

Until recently, the cytokines IL-2 and IFNα were the only active systemic treatments for advanced or metastatic RCC. However, due to each of these agent's limited clinical benefit and substantial toxicity profile, newer targeted agents have largely replaced cytokines in the treatment of advanced or metastatic renal cell carcinoma. The recognition of the importance of hypoxia inducible factor alpha (HIFα) signaling in the pathogenesis of clear-cell RCC has led to widespread study of two classes of targeted therapies, anti-angiogenic agents and mammalian target of rapamycin (mTOR) inhibitors (Mulders, 2009). Targeting of angiogenesis is rational because constitutive HIFα activation leads to the upregulation or activation of several proteins including vascular endothelial growth factor (VEGF), which can subsequently lead to tumor proliferation and neovasculature formation. Targeting of the mTOR pathway is important because activation of the upstream PI3K/Akt/mTOR signaling pathway is one method by which constitutive HIFα activation or upregulation occurs (Mulders, 2009). Agents that target angiogenesis include VEGF-receptor (VEGFr) TKIs (e.g., sorafenib, sunitinib, pazopanib, axitinib, and tivozanib) and VEGF-binding mAbs (e.g., bevacizumab), while agents that target the mTOR pathway include the mTOR inhibitors (e.g., everolimus and temsirolimus). However, most patients develop resistance, and overall survival (OS) improvement has only been shown in one Phase 3 trial in poor-risk patients. Everolimus demonstrated a 3-month improvement in median progression-free survival (PFS) versus placebo, with no OS improvement (Motzer et al., 2008). Among the five approved anti-angiogenic agents (sorafenib, sunitinib, bevacizumab, pazopanib, and axitinib) and two approved mTOR inhibitors (temsirolimus, everolimus), only everolimus is approved specifically for use after the failure of treatment with anti-angiogenic therapy. In the US, everolimus is indicated for the treatment of advanced RCC after failure of treatment with sunitinib or sorafenib, whereas in the EU, everolimus is more broadly indicated for patients with advanced RCC, whose disease has progressed on or after treatment with VEGF-targeted therapy.

Non-Small Cell Lung Cancer

NSCLC is the leading cause of cancer death worldwide, exceeding breast, colon and prostate cancer combined. The majority of subjects (approximately 78%) are diagnosed with advanced/recurrent or metastatic disease. NSCLC therapies have incrementally improved OS, but benefit has reached a plateau (median OS for late stage patients is just 1 year). Progression after 1 L therapy occurred in nearly all of these subjects and the 5-year survival rate is only 3.6% in the refractory setting.

There is a particular unmet need among patients who have squamous cell NSCLC (representing up to 25% of all NSCLC) as there are few treatment options after 1 L therapy. Surgery, radiation therapy (RT) and chemotherapy are the three modalities commonly used to treat NSCLC patients. As a class, NSCLCs are relatively insensitive to chemotherapy, compared to small cell carcinoma. In general, for patients with Stage I or II disease, surgery provides the best chance for cure, with chemotherapy increasingly being used both pre-operatively and post-operatively. RT can also be used as adjuvant therapy for patients with resectable NSCLC, the primary local treatment, or as palliative therapy for patients with incurable NSCLC.

Patients with Stage IV disease who have a good performance status (PS) benefit from chemotherapy. Many drugs, including platinum agents (e.g., cisplatin, carboplatin), taxanes agents (e.g., paclitaxel, albumin-bound paclitaxel, docetaxel) vinorelbine, vinblastine, etoposide, pemetrexed and gemcitabine are useful for Stage IV NSCLC. Combinations using many of these drugs produce 1-year survival rates of 30% to 40% and are superior to single agents. Specific targeted therapies have also been developed for the treatment of advanced lung cancer. For example, bevacizumab (AVASTIN®) is a mAb that blocks vascular endothelial growth factor A (VEGF-A). Erlotinib (TARCEVA®) is a small-molecule TKI of epidermal growth factor receptor (EGFR). Crizotinib (XALKORI®) is a small-molecule TKI that targets ALK and MET, and is used to treat NSCLC in patients carrying the mutated ALK fusion gene. Cetuximab (ERBITUX®) is a mAb that targets EGFR.

Squamous cell carcinoma (SCC) represents one quarter of NSCLC cases and has limited treatment options. Currently, second-line treatment for SCC remains an area of unmet need. Single-agent chemotherapy is standard of care following progression with platinum-based doublet chemotherapy (Pt-doublet), resulting in median OS of approximately 7 months. Docetaxel remains the benchmark treatment in this line of therapy although erlotinib may also used with less frequency. Pemetrexed has also been shown to produce clinically equivalent efficacy outcomes but with significantly fewer side effects compared with docetaxel in the 2 L treatment of patients with advanced NSCLC (Hanna et al., 2004). No therapy is currently approved for use in lung cancer beyond the 3 L setting. Pemetrexed and bevacizumab are not approved in SCC, and molecularly targeted therapies have limited application.

The present invention is further illustrated by the following examples which should not be construed as further limiting. The contents of all figures and all references, patents and published patent applications cited throughout this application are expressly incorporated herein by reference.

Example 1

Cross-Competition Between Anti-PD-1 HuMAbs for Binding to CHO Cells Expressing Human PD-1

Chinese Hamster Ovary (CHO) cells transfected to express human PD-1 (CHO/PD-1 cells) were incubated with 10 µg/ml of Fab fragment of the anti-PD-1 HuMAb 5C4 or human IgG1 (hIgG1) isotype control Ab for 30 minutes at 4° C. before addition of anti-PD-1 HuMAbs 2D3, 7D3 or 4H1 at a concentration of 0.2 µg/ml. Binding of 4H1, 2D3 or 7D3 to CHO/PD-1 cells were detected by fluorescein isothiocyanate (FITC)-conjugated goat anti-hIgG, Fc-gamma specific Ab. In the case of cross-competition assay with 5C4 and 17D8, CHO/PD-1 cells were incubated with the whole molecule of 5C4 before addition of FITC-labeled 17D8. Binding of 2D3, 7D3, 4H1 or 17D8 to the CHO/PD-1 cells was measured by flow cytometric analysis using a FACS® calibur flow cytometer (Becton Dickinson, San Jose, Calif.).

The results are depicted in FIG. 1. The data show that the 5C4 Fab fragment substantially blocked the binding of mAbs 5C4 itself, as well as the binding of 2D3, 7D3 (FIG. 1A) and 4H1 (FIG. 1B), while the 5C4 whole mAb substantially blocked the binding of 17D8 (FIG. 1C) to CHO/PD-1 cells as measured by mean fluorescent intensity (MFI) of staining.

Example 2

Cross-Competition Between Anti-PD-L1 HuMAbs for Binding to CHO Cells Expressing Human PD-L1

CHO cells transfected to express hPD-L1 (CHO/PD-L1 cells) were incubated with 10 µg/ml of each of ten unconjugated human anti-PD-L1 mAbs (5F8, 7H1, 10H10, 1B12, 3G10, 10A5, 11E6, 12A4, 12B7, and 13G4) or human IgG1 (hIgG1) isotype control Ab for 20 min at 4° C. FITC-conjugated 10H10 (A), 3G10 (B), 10A5 (C), 11E6 (D), 12A4 (E) or 13G4 (F) was added to the cells to a final concentration of 0.09 µg/ml (B, D), 0.27 µg/ml (A, C), 0.91 µg/ml (F), or 2.73 µg/ml (E) for an additional 20 min at 4° C. without prior washout of unbound, unconjugated Ab. Different quantities of the various FITC-conjugated HuMAbs were used due to differences in binding efficiency following labeling, and the optimal amounts of these FITC-conjugated HuMAbs were previously determined by dose-titration analysis of binding to CHO/PD-L1 cells. Binding of FITC-conjugated 10H10, 3G10, 10A5, 11E6, 12A4 or 13G4 to the CHO/PD-L1 cells was measured by flow cytometry.

Figure 2A:
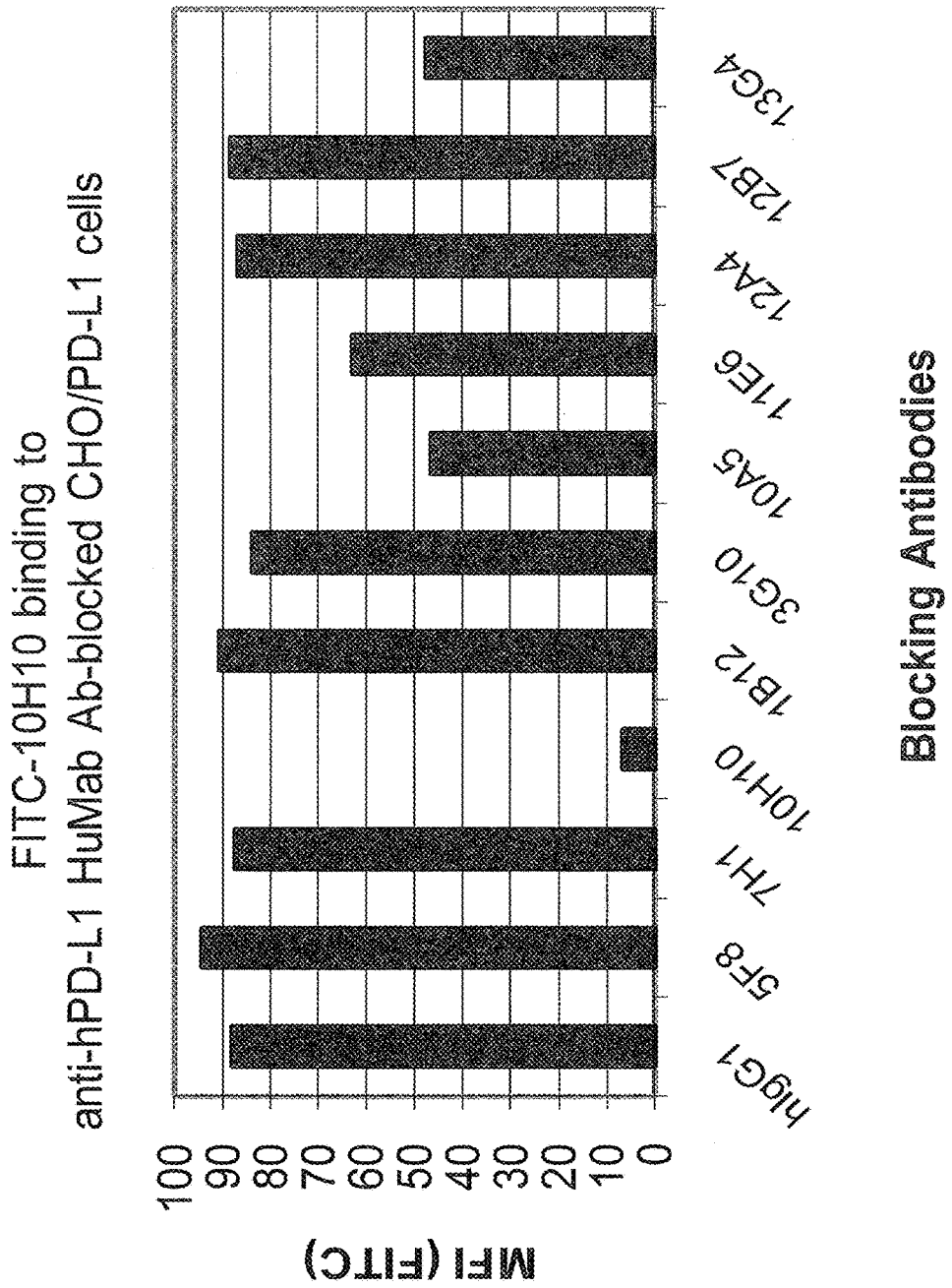
Figure 2D:
Figure 2E:

The results are depicted in FIG. 2. Binding of labeled 10H10 was partially blocked by 10A5, 11E6 and 13G4, but was substantially blocked only by itself (FIG. 2A). Conversely, 10H10 substantially blocked the binding only of itself to CHO/PD-L1 cells. Each of anti-PD-L1 HuMAbs 5F8, 7H1, 1B12, 3G10, 10A5, 11E6, 12A4, 12B7 and 13G4 substantially blocked binding of labeled mAbs 3G10 (FIG. 2B), 10A5 (FIG. 2C), 11E6 (FIG. 2D), 12A4 (FIG. 2E) and 13G4 (FIG. 2F) to CHO/PD-L1 cells as measured by MFI, though mAbs 5F8 and 13G4 generally blocked binding of the labeled mAbs to a slightly lesser extent.

Example 3

Cross-Competition Between Anti-PD-L1 mAbs for Binding to Ovarian Carcinoma Cells Expressing Human PD-L1

Anti-PD-L1 HuMAbs 5F8, 12B7, 3G10, 1B12, 13G4, 10H10, 10A5 and 12A4, and a human IgG1 (huIgG1)

isotype control Ab were serially diluted from 10 µg/ml and incubated with hPD-L1-expressing ES-2 ovarian carcinoma cells for 20 minutes at 4° C. Without washing, biotinylated-12A4 Ab was added to a final concentration of 0.4 µg/ml for an additional 20 minutes at 4° C. After washing, bound biotin-12A4 was detected using fluorescent streptavidin-PE secondary reagent and measured by flow cytometry. FIG. 3 shows the fluorescence of bound biotin-12A4 plotted against the concentration of unlabeled hPD-L1 HuMAbs. Binding of biotin-12A4 to ES-2 cells was substantially blocked by 12A4 itself and by 1B12 and 12B7, and was moderately to significantly blocked by mAbs 5F8, 10A5, 13G4 and 3G10, but was not blocked by mAb 10H10.

Example 4

Design of Phase I Clinical Study of Anti-PD-1 Antibody

A Phase I study was conducted to assess the safety, antitumor activity, and pharmacokinetics of an anti-PD-1 in patients with selected advanced solid tumors. The human anti-PD-1 mAb, BMS-936558 (also referred to herein as nivolumab, and in U.S. Pat. No. 8,008,449 as 5C4), was administered as an intravenous infusion every 2 weeks of each 8-week treatment cycle. Patients continued treatment for up to 2 years (12 cycles), unless they experienced complete remission, unacceptable toxicity, disease progression, or withdrew consent. In patients who were otherwise clinically stable, study treatment was continued beyond apparent initial disease progression until further progression was noted as recommended by proposed immune response criteria (Wolchok et al., 2009). Patients with stable disease (SD) or an ongoing objective response (OR: complete [CR] or partial response [PR]) at the end of treatment were followed for 1 year and were offered retreatment for 1 additional year in the event of progression.

Dose Escalation

Patients with advanced melanoma (MEL), non-small cell lung (NSCLC), renal cell carcinoma (RCC), castration-resistant prostate (CRPC) and colorectal cancer (CRC) were eligible to enroll. Cohorts of 3-6 patients per dose level were enrolled sequentially at 1.0, 3.0, and 10.0 mg/kg. Dose escalation proceeded when a minimum of 3 patients had completed the safety evaluation period (56 days) at the given dose level, with dose-limiting toxicity in less than one-third of patients. Intra-patient dose escalation was not permitted.

Cohort Expansion

A maximum tolerated dose (MTD) was not reached. Initially, 5 expansion cohorts of approximately 16 patients each were enrolled at 10 mg/kg for MEL, NSCLC, RCC, CRPC and CRC. Based on initial signals of activity, additional expansion cohorts of approximately 16 patients each were enrolled for MEL (at 1.0 and 3.0 mg/kg, followed by cohorts randomized to 0.1, 0.3, or 1.0 mg/kg), NSCLC (squamous or nonsquamous histology cohorts randomized to 1, 3, or 10 mg/kg), and RCC (at 1.0 mg/kg).

Patients

Eligible patients had documented advanced solid tumors; age >18 years; life expectancy >12 weeks; Eastern Cooperative Oncology Group performance status of ≤2; measurable disease by Response Evaluation Criteria in Solid Tumors (RECIST), v1.0 with modification (see Topalian et al., 2012b); adequate hematologic, hepatic, and renal function; and received 1-5 prior systemic treatment regimens. Patients with stable treated brain metastases were enrolled. Exclusion criteria included a history of chronic autoimmune disease, prior therapy with T-cell modulating Abs (e.g., anti-CTLA-4), conditions requiring immunosuppressive medications, and chronic infections (HIV, hepatitis B or C).

A total of 296 patients with advanced solid tumors including MEL (n=104), NSCLC (n=122), RCC (n=34), CRPC (n=17), and CRC (n=19) were treated with BMS-936558 for 40 months up to February 2012. By March 2013, 304 patients including patients with non-small cell lung cancer (n=127), melanoma (n=107), RCC (n=34), CRPC (n=17), and CRC (n=19) had been treated with BMS-936558 from October 2008 through March 2012, all with a minimum of one year and up to about 4.4 years of observation. Two patients did not receive a full cycle of treatment and were not considered response-evaluable. The majority of patients were heavily pretreated, with 47% having received at least 3 prior regimens. Notable prior therapies included immunotherapy (64%) and B-RAF inhibitor (8%) in MEL patients; platinum-based chemotherapy (94%) and tyrosine kinase inhibitors (TKIs, 34%) in NSCLC patients; and nephrectomy (94%), immunotherapy (59%), and anti-angiogenic therapy (74%) in RCC patients. Baseline characteristics of the total treated population (N=296) were similar to those of the efficacy population (response evaluable patients, N=236). Details on the patient pre-treatments are provided in Topalian et al., 2012b.

Statistical Analysis

All patients (N=304) treated as of the date of analysis (March 2013) were used for summaries of baseline characteristics and AEs. Pharmacokinetic and molecular-marker populations consisted of treated patients with available data as of the date of analysis. The efficacy population consisted of response-evaluable patients commencing treatment at least 8 months before the date of analysis. Tumor measurements were collected after each treatment cycle (4 doses) by investigators. Individual best objective responses based on the tumor measurements were assessed by the sponsor per modified RECIST v1.0. Objective response was confirmed by at least one sequential tumor assessment. Objective response and stable disease rates were estimated with confidence intervals using the Clopper-Pearson method. Time-to-event endpoints including progression-free survival, overall survival, survival rates, and duration of response, were estimated using the Kaplan-Meier method. AEs were coded using Medical Dictionary for Regulatory Activities (MedDRA), version 14.1. AEs of special interest (AEOSIs), with potential immune-related etiologies, defined as adverse events that require more frequent monitoring and/or unique intervention, were identified using a pre-defined list of MeDRA terms. Individual best ORs were derived from investigator-reported data per modified RECIST v1.0. OR was confirmed by at least one sequential tumor assessment and OR rate (ORR={[CR+PR]÷n}×100) was calculated.

Example 5

Safety Evaluations on Patients Treated with Anti-PD-1 Antibody

Safety evaluations, including clinical examination and laboratory assessments, were conducted in all treated patients at baseline and regular intervals up to 100 days following last administration of drug. The severity of AEs was graded based on the NCI Common Terminology Criteria for Adverse Events (NCI CTCAE), v3.0. Computed tomography (CT) or magnetic resonance imaging was performed for tumor assessment at baseline and following each treatment cycle.

A MTD was not defined across the doses of BMS-936558 tested on this study. A relative BMS-936558 dose intensity of 90% or higher was achieved in 87% of patients (see Topalian et al., 2012b, for details). AEs were coded using Medical Dictionary for Regulatory Activities (MedDRA), version 14.1. AEOSIs were identified using a pre-defined list of MeDRA terms. Fifteen of 296 (5%) patients discontinued treatment due to BMS-936558-related AEs. As of the date of analysis, 62 (21%) patients had died, with disease progression being the most common cause of death (Topalian et al., 2012b).

The most common adverse events, regardless of causality included fatigue, decreased appetite, diarrhea, nausea, cough, dyspnea, constipation, vomiting, rash, pyrexia and pruritus (Topalian et al., 2012b). Common BMS-936558-related AEs included fatigue, rash, diarrhea, decreased appetite, and nausea. The majority of the events were low grade, with grade 3-4 drug-related AEs observed in 41 of 296 (14%) patients. Drug-related serious AEs occurred in 32 of 296 (11%) patients (Topalian et al., 2012b). The spectrum, frequency, and severity of BMS-936558-related AEs were generally similar across the dose levels tested. Drug-related AEOSIs, with potential immune-related etiologies, included pneumonitis, vitiligo, colitis, hepatitis, hypophysitis, and thyroiditis among others. Hepatic or gastrointestinal AEOSIs were managed with treatment interruption and, as necessary, with administration of corticosteroids. Among patients treated to-date, these AEs (in 13 patients with diarrhea; 11 patients with hepatic AEs) were reversible in all cases. Endocrine AEOSIs were managed with replacement therapy. At the discretion of the treating physician, patients successfully reinitiated treatment with BMS-936558. Drug-related pneumonitis occurred in 9 of 296 (3%) patients. Grade 3-4 pneumonitis developed in 3 patients (1%). No clear relationship between the occurrence of pneumonitis and tumor type, dose level, or the number of doses received was noted. Early grade pneumonitis was generally reversible with treatment discontinuation and corticosteroid administration. In 3 patients with pneumonitis, infliximab and/or mycophenolate were utilized for additional immunosuppression; however, given the small number of patients and variable outcomes, the effectiveness of this treatment is unclear. There were 3 (1%) drug-related deaths due to pneumonitis (2 NSCLC patients, 1 CRC).

Example 6

Pharmacokinetics/Pharmacodynamics Analyses on Anti-PD-1 Antibody

For pharmacokinetic (PK) analyses, serial blood samples were collected and serum concentrations of BMS-936558 were quantified using by ELISA. For pharmacodynamic (PD) analysis, peripheral blood mononuclear cells were isolated from patients at baseline and following cycle 1 to estimate PD-1 receptor occupancy (RO) by BMS-936558 on circulating CD3+ T-cells via flow cytometry (Brahmer et al., 2010).

The maximum concentration of BMS-936558 was observed at a median T. of 1-4 hours after the start of infusion. The PK of BMS-936558 was linear with a dose proportional increase in C. and $AUC_{(0-14\ d)}$ in the dose range of 0.1-10 mg/kg (n=35). BMS-936558 PD was assessed by PD-1 RO on circulating T-cells. PBMCs from 65 MEL patients treated with one cycle of BMS-936558 at 0.1-10 mg/kg biweekly demonstrated median occupancy of PD-1 molecules on circulating $CD3^+$ T-cells by BMS-936558 ranging from 64%-70% (see Topalian et al., 2012b, for details).

Example 7

Antitumor Efficacy Exhibited by Anti-PD-1 Antibody

Figure 4:
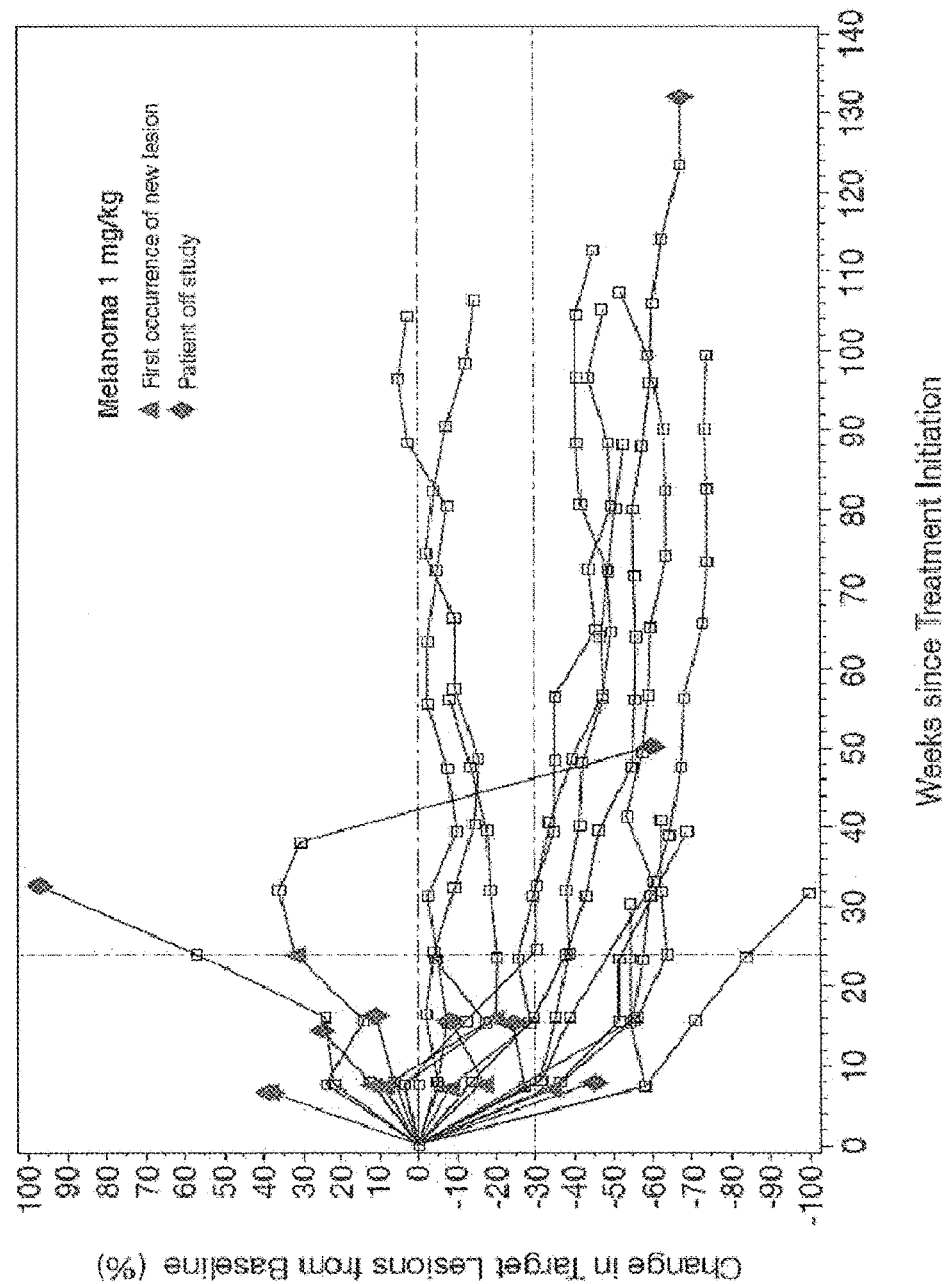
FIG. 4. Spider plot showing activity of anti-PD-1 mAb in patients with treatment-refractory melanoma (MEL). A representative plot of changes in tumor burden over time demonstrates the time course of change in the sum of the longest diameters of target lesions, compared with baseline, in 27 MEL patients treated with 5C4 at a dose of 1.0 mg/kg. In the majority of patients who achieved an objective response (OR), responses were durable and evident by the end of cycle 3 (6 months) of treatment (vertical dashed line). Tumor regressions followed conventional as well as "immune-related" patterns of response, such as prolonged reduction in tumor burden in the presence of new lesions.
Figure 6:
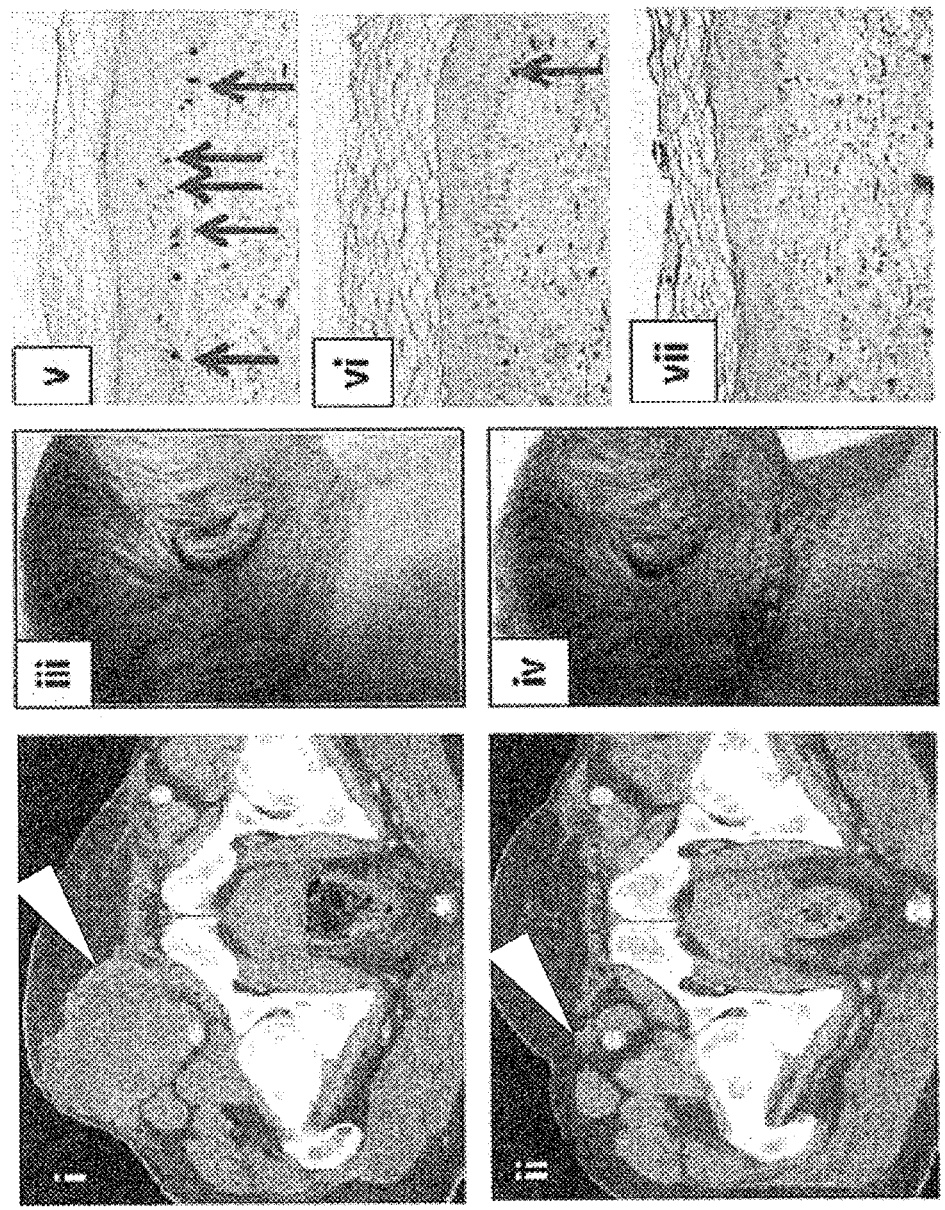
FIG. 6. Activity of anti-PD-1 mAb in patient with metastatic MEL. A complete response of metastatic MEL is illustrated in a 62-year-old patient treated with 5C4 at 3 mg/kg, associated with vitiligo. (i) Pretreatment CT scan, inguinal lymph node metastasis (arrow); (ii) after 13 months of treatment. Numerous metastases in the subcutaneous tissue and retroperitoneum also regressed completely (not shown). Vitiligo developed after 6 months of treatment; photos taken at 9 months under visible light (iii) and ultraviolet light (iv). Skin biopsies with immunohistochemistry for microphthalmia-associated transcription factor (MITF) show melanocytes (arrows) at the epidermal-dermal junction in normal skin (v), and scarce (vi) or absent (vii) melanocytes in skin partially or fully affected by vitiligo.
Figure 7:
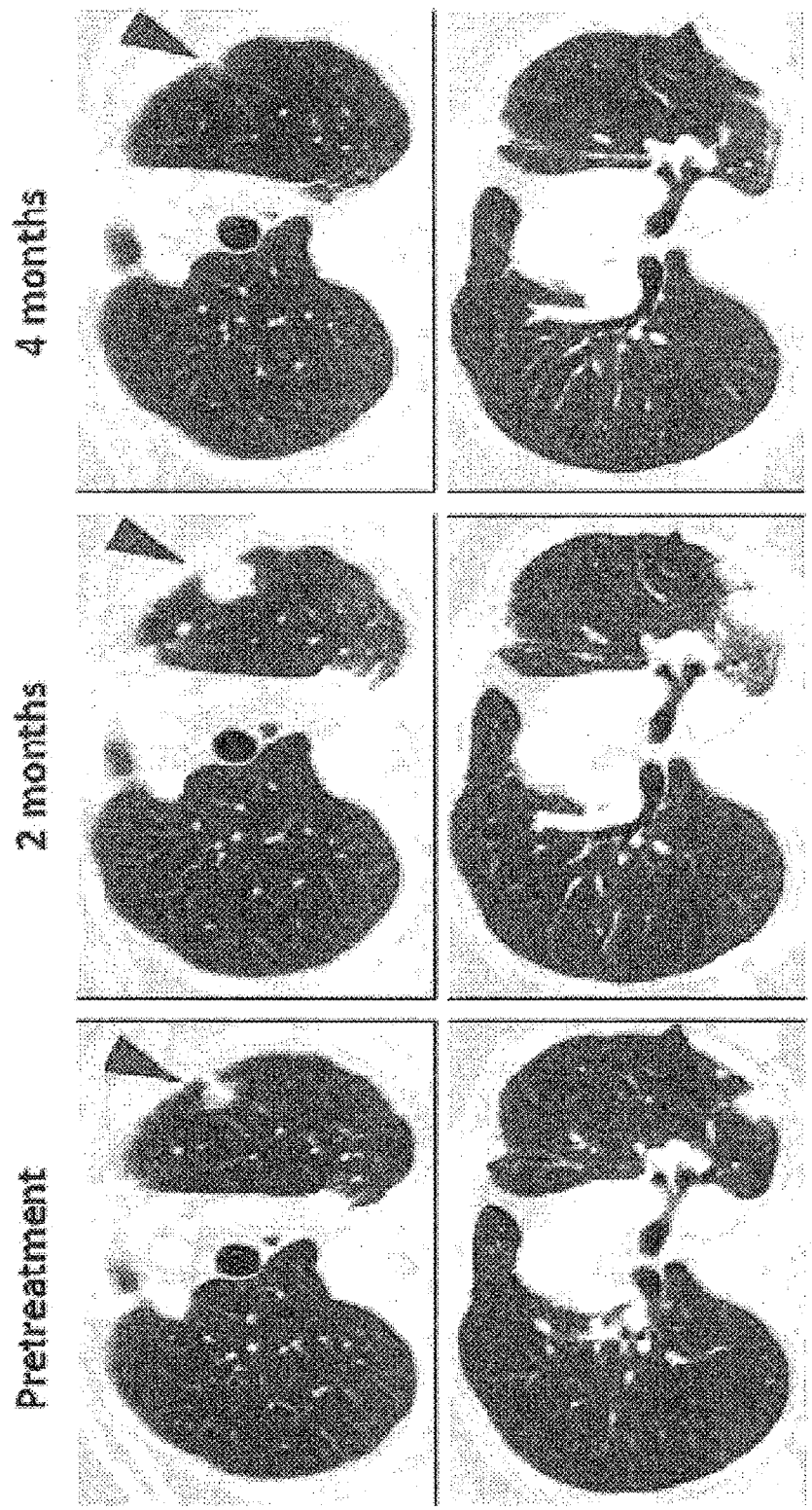
FIG. 7. Activity of anti-PD-1 mAb in patient with metastatic NSCLC. A partial response is illustrated in a patient with metastatic NSCLC (nonsquamous histology) treated with 5C4 at 10 mg/kg. Arrows show initial progression in pulmonary lesions followed by regression ("immune-related" pattern of response).

Analysis of data obtained since February 2012 is ongoing; thus, unless otherwise noted, the data presented below were obtained as of February 2012. Clinical antitumor activity was observed at all BMS-936558 doses tested. ORs (confirmed CR or PR) were observed in a substantial portion of patients with NSCLC, MEL, and RCC (Tables 1-3; FIG. 4), and in various sites of metastatic disease including liver, lung, lymph nodes, and bone (FIGS. 5-7 and not shown). Tumor regressions followed conventional as well as "immune-related" patterns of response, such as prolonged reduction in tumor burden in the presence of new lesions. Individual best overall responses were derived from investigator-reported data according to modified RECIST v1.0. OR was confirmed by at least one sequential tumor assessment. At the time of data analysis, 2 patients with NSCLC who were treated with 10 mg/kg had unconfirmed responses, and 8 additional patients (with MEL, NSCLC, or RCC) had a persistent reduction in baseline target lesions in the presence of new lesions, (i.e., an "immune-related" response pattern). None of these patients was categorized as a responder for the purpose of calculating OR rates. Antitumor responses and/or prolonged disease stabilization were observed in patients irrespective of prior therapies received (see summary of progression free interval for patients with OR and SD in Supplementary Appendix 4 of Topalian et al., 2012b).

In NSCLC patients, 14 ORs were observed at BMS-936558 doses of 1, 3, or 10 mg/kg with response rates of 6%, 32%, and 18%, respectively. ORs were observed across NSCLC histologies: 6 responders of 18 squamous (33%), 7 responders of 56 nonsquamous (13%), and 1 of 2 unknown. All 14 patients with ORs started treatment ≥24 weeks before data analysis, and of these, 8 had response duration ≥24 weeks (Table 1). Stable disease (SD) lasting ≥24 weeks was observed in 5 (7%) NSCLC patients, all with nonsquamous histology. Among MEL patients, 26 ORs were observed at doses ranging from 0.1-10 mg/kg, with response rates ranging from 19%-41% per dose level. At the 3 mg/kg dose level, ORs were noted in 7 of 17 (41%) patients. Of 26 MEL patients who achieved an OR, 17 started treatment ≥1 year before data analysis, and of these, 13 patients had an OR duration ≥1 yr. The remaining 8 patients with OR were on study <1 year and 6 had responses ranging from 1.9-5.6 months. SD lasting ≥24 weeks was observed in 6 (6%) patients. In RCC patients, ORs occurred in 4 of 17 (24%) patients treated with a BMS-936558 dose of 1 mg/kg and 5 of 16 (31%) patients treated with 10 mg/kg. Among 8 RCC patients with OR who started treatment ≥1 year prior to data analysis, 5 (63%) had OR duration ≥1 yr. SD lasting ≥24 weeks was observed in an additional 9 (27%) patients.

TABLE 1

Clinical Activity of BMS-936558 in the Efficacy Population* (N = 236)[†]

| Tumor Type | Dose (mg/kg) | n | ORR[‡] No. Patients (%) [95% CI][†] | SD ≥ 24 wk No. Patients (%) [95% CI] | PFSR[§] at 24 wk (%) [95% CI] |
|---|---|---|---|---|---|
| MEL | 0.1 | 14 | 4 (29) [8-58] | 1 (7) [0.2-34] | 40 [13-66] |
|  | 1.0 | 27 | 8 (30) [14-50] | 3 (11) [2-29] | 45 [26-65] |
|  | 3.0 | 17 | 7 (41) [18-67] | 1 (6) [0.1-29] | 55 [30-80] |
|  | 10.0 | 20 | 4 (20) [6-44] | 0 | 30 [9-51] |
| ALL MEL |  | 94 | 26 (28) [19-38] | 6 (6) [2-13] | 41 [30-51] |
| NSCLC** |  |  |  |  |  |
| All | 1 | 18 | 1 (6) [0.1-27] | 1 (6) [0.1-27] | 16 [0-34] |
| Squamous | 1 | 5 | 0 | 0 | 0 |
| Non-squamous | 1 | 12 | 0 | 1 (8) [0.2-39] | 14 [0-37] |
| Unknown | 1 | 1 | 1 (100) [3-100] | 0 | 1 |
| All | 3 | 19 | 6 (32) [13-57] | 2 (11) [1-33] | 41 [18-64] |
| Squamous | 3 | 6 | 3 (50) [12-88] | 0 | 50 [10-90] |
| Non-squamous | 3 | 13 | 3 (23) [5-54] | 2 (15) [2-45] | 37 [10-64] |
| All | 10 | 39 | 7 (18) [8-34] | 2 (5) [0.6-17] | 24 [11-38] |
| Squamous | 10 | 7 | 3 (43) [10-82] | 0 | 43 [6-80] |
| Non-squamous | 10 | 31 | 4 (13) [4-30] | 2 (7) [0.8-21] | 21 [6-36] |
| Unknown | 10 | 1 | 0 | 0 | 0 |
| ALL NSCLC |  | 76 | 14 (18) [11-29] | 5 (7) [2-15] | 26 [16-36] |
| All Squamous |  | 18 | 6 (33) [13-59] | 0 | 33 [12-55] |
| All Non-squamous |  | 56 | 7 (13) [5-24] | 5 (9) [3-20] | 22 [11-34] |
| RCC | 1 | 17 | 4 (24) [7-50] | 4 (24) [7-50] | 47 [23-71] |
|  | 10 | 16 | 5 (31) [11-59][‡] | 5 (31) [11-59][¶] | 67 [43-91] |
| ALL RCC |  | 33 | 9 (27) [13-46] | 9 (27) [13-46] | 56 [39-73 |

*The efficacy population consists of response-evaluable patients whose treatment was initiated at least 8 months before data analysis in February 2012, and had measurable disease at baseline and one of the following: at least 1 on-treatment scan or clinical evidence of disease progression or death.
[†]CR denotes complete response, MEL melanoma, NSCLC non-small cell lung cancer, ORR objective response rate, PFSR progression-free survival rate, PR partial response, RCC renal cell cancer, SD stable disease, n number of patients.
[‡]Objective response rates ({[CR + PR] ÷ n} × 100) have been calculated based on confirmed responses with confidence intervals calculated using the Clopper-Pearson method. Individual patient responses were adjudicated per RECIST v1.0 with modification (see Topalian et al., 2012b).
[§]Progression-free survival rate was the proportion of patients who did not progress and were alive at 24 weeks calculated by the Kaplan-Meier methodology with confidence intervals using the Greenwood method.
[¶]One CR.
**One NSCLC patient who was treated at the 3 mg/kg dose level had an initial evaluation of progressive disease, subsequently had a PR, and was classified as a responder.

TABLE 2

Clinical Activity of BMS-936558 in the Efficacy Population*

| Tumor Type | ORR[a] No. of patients/total no. of patients (%) [95% CI] | SD ≥ 24 wk No. of patients/total no. of patients (%) [95% CI] | Median Overall Survival (95% CI) | Overall Survival Rate (95% CI); patients at risk, n | | |
|---|---|---|---|---|---|---|
|  |  |  |  | 1 y | 2 y | 3 y |
| NSCLC | 20/122 (16.4) [10.3, 24.2] | 11/122 (9.0) [4.6, 15.6] | NA | 43 (33-53); 24 | 32 (18-47); 4 | 24 (7-41); 1 |
| Squamous | 9/48 (18.8) [8.9, 32.6] | NA | NA | NA | NA | NA |
| Non-sq. | 11/73 (15.1) [7.8, 25.4] | NA | NA | NA | NA | NA |
| MEL | 33/106 (31.1) [22.5, 40.9] | 6/106 (5.7) [2.1, 11.9] | 16.8 (12.5, NR) | 61 (52-71); 50 | 44 (33-56); 24 | 40 (29-52); 1 |
| RCC | 10/34 (29.4) [15.1, 47.5] | 9/34 (26.5) [12.9, 44.4] | NR (13.6, NR) | 70 (55-86); 22 | 52 (32-72); 7 | 52 (32-72); 1 |

*The efficacy population consists of response-evaluable patients up to March 2013
[a]Objective response rate was calculated as {[CR + PR] ÷ n} × 100.
NR—not reached
NA—not available from Jul. 3, 2012 data cut. The percentage of patients with stable disease for ≥36 weeks or ≥48 weeks [95% CI], median duration of response (months) and median progression-free survival (95% CI) were N/A.

The following results are drawn from preliminary analyses of BMS-936558 clinical efficacy data as of March 2013. Sustained survival, as reflected by median overall survival and 1- and 2-year landmark overall survival rates, was noted in each of the responding patient populations (Table 2). Median overall survivals of 9.6 months for lung cancer, 16.8 months for melanoma, and greater than 22 months for kidney cancer, were observed. Thirteen patients with melanoma, lung or kidney cancer were characterized as having unconventional response patterns that did not meet RECIST criteria (e.g., persistent reduction in target lesions in the presence of new lesions or following initial progression) (Wolchok et al, 2009).

TABLE 3

Duration of Objective Responses to BMS-936558*

| Tumor Type | Dose (mg/kg) | No. of Patients with OR | Duration of Response (months)[†] |
|---|---|---|---|
| MEL | 0.1 | 4 | 7.5+, 5.6+, 5.6, 5.6 |
|  | 0.3 | 3 | 3.8+, 2.1+, 1.9+ |
|  | 1 | 8 | 24.9+, 22.9, 20.3+, 19.3+, 18.4+, 7.6+, 5.6+, 5.3+ |
|  | 3 | 7 | 22.4+, 18.3+, 15.2+, 12.9, 11.1, 9.3, 9.2+ |
|  | 10 | 4 | 24.6+, 23.9+, 18.0+, 17.0 |
| NSCLC[§] | 1 | 1 | 9.2+ |
|  | 3 | 6 | 30.8+, 7.6+, 5.5+, 3.7+, 1.9+, NA[‡] |
|  | 10 | 7 | 14.8+, 7.6+, 7.3+, 6.7, 4.2, 3.7+, 3.7 |
| RCC | 1 | 4 | 17.5+, 9.2+, 9.2, 5.6+ |
|  | 10 | 5 | 22.3+, 21.7+, 12.9, 12.0, 8.4 |

*MEL denotes melanoma, NA not applicable, NSCLC non-small cell lung cancer, RCC renal cell cancer.
[†]Time from first response to time of documented progression, death, or for censored data, time to last tumor assessment.
[‡]One patient was treated beyond an initial evaluation of progressive disease and subsequently had a PR; this patient was classified as a responder for the purposes of calculating response rates by RECIST v1.0 but was not eligible for calculation of duration of response.

Example 8

Measurement of Membranous PD-L1 Expression by Standard IHC Assay

IHC staining of PD-L1 was performed on pretreatment formalin-fixed paraffin-embedded (FFPE) tumor specimens using the murine anti-human PD-L1 mAb 5H1 (Dong et al., 2002) in a standard IHC protocol (Taube et al., 2012; Supp. Materials). Briefly, 5 µm-FFPE sections mounted on glass slides were deparaffinized in xylene and antigen retrieval was performed using a Tris-EDTA buffer, pH 9.0 at 120° C. for 10 min in a Decloaking Chamber (Biocare Medical). Endogenous peroxidase, biotin and proteins were blocked (CAS system K1500, Dako; Avidin/biotin Blocking Kit, SP-2001, Vector Laboratories; Serotec Block ACE). The primary 5H1 Ab was applied at a concentration of 2 µg/ml and allowed to incubate at 4° C. for 20 h. Secondary Ab (biotinylated anti-mouse IgG1, 553441 BD) was applied at a concentration of 1 µg/ml for 30 min at room temperature (RT). The signal was then developed with amplification according to the manufacturer's protocol (CAS system K1500, Dako). Sections were counterstained with hematoxylin, dehydrated in ethanol and cleared in xylene, and a coverslip was applied.

The percentage of tumor cells exhibiting cell surface staining for PD-L1 was scored by two independent pathologists who were blinded to treatment outcomes. PD-L1 positivity was defined per specimen by a 5% expression threshold (Taube et al., 2012; Thompson et al., 2006), and in cases with multiple specimens, if any specimen met this criterion. A Fisher's exact test was applied to assess the association between PD-L1 expression and OR, noting, however, that this analysis was based in part on optional biopsies from a non-random subset of the population and testing of a statistical hypothesis was not pre-specified.

Figure 8A:
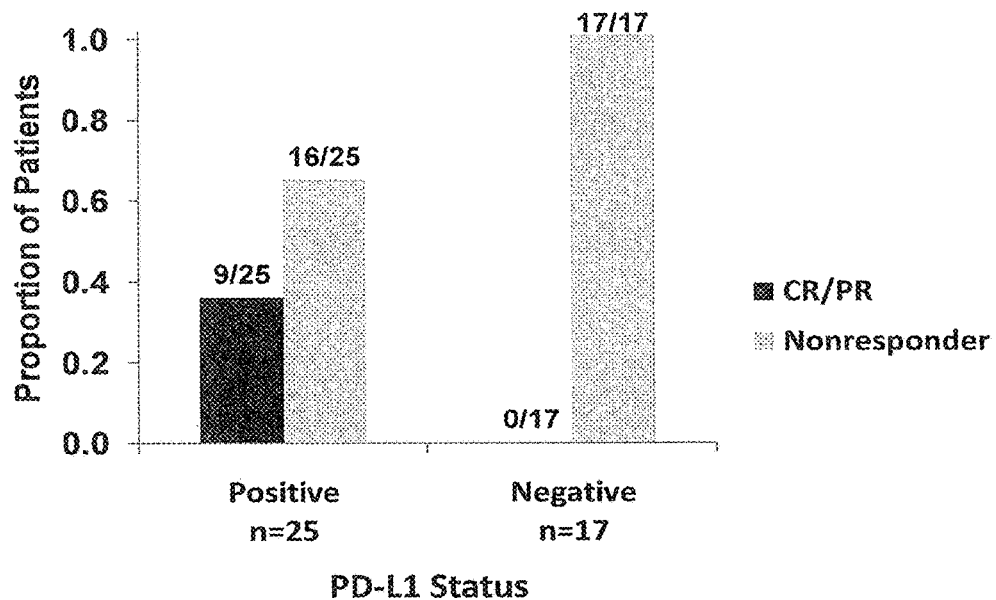
FIGS. 8A and 8B. Correlation between tumor PD-L1 expression and anti-PD-1 clinical response. Pretreatment tumor cell surface expression of PD-L1, as determined by IHC on formalin-fixed paraffin-embedded specimens, correlates with OR to PD-1 blockade. Forty-two subjects with advanced cancers including melanoma, non-small cell lung cancer, colorectal cancer, renal cell cancer, and castration-resistant prostate cancer (n=18, 10, 7, 5, and 2, respectively) were studied. A, There was a significant correlation of tumor cell surface PD-L1 expression with objective clinical response. No patients with PD-L1 negative tumors experienced an OR. B, Examples of IHC analysis with the anti-PD-L1 mAb 5H1 are shown in a melanoma lymph node metastasis (top), a renal cell cancer nephrectomy specimen (middle), and a lung adenocarcinoma brain metastasis (bottom). All 400× original magnification. Arrows indicate one of many tumor cells in each specimen with surface membrane staining for PD-L1. Asterisk indicates a normal glomerulus in the nephrectomy specimen, which is negative for PD-L1 staining.
Figure 8B:
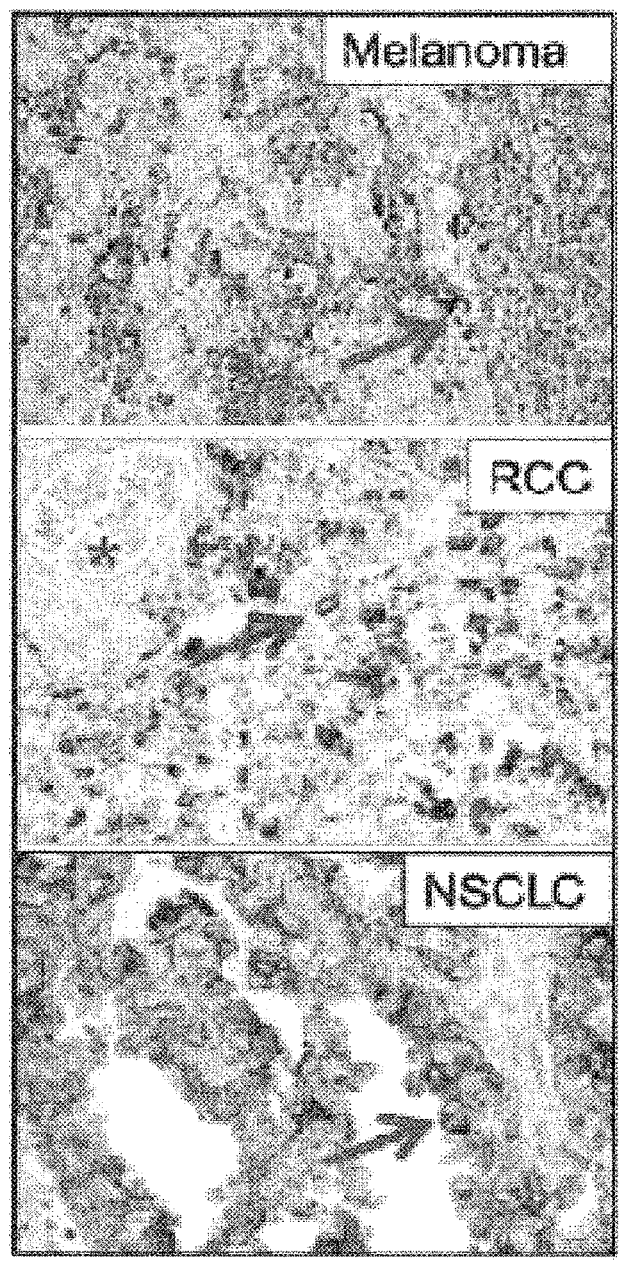

Sixty-one pretreatment tumor specimens from 42 patients (18 MEL, 10 NSCLC, 7 CRC, 5 RCC, and 2 CRPC) were analyzed for tumor cell surface PD-L1 expression (FIG. 8). Biopsy specimens from 25 of 42 patients were positive for PD-L1 expression by IHC. A Fisher's exact test was applied to assess the association between PD-L1 expression and OR in a post-hoc analysis. Among the 42 surface-PD-L1$^+$ patients, 9 (36%) achieved an OR. Importantly, among 17 patients with PD-L1$^-$ tumors, none achieved an OR. Thus, in a subset of patients cell surface expression of PD-L1 on tumor cells in pretreatment biopsies is associated with an increased rate of OR among patients treated with BMS-936558, while no patients with documented PD-L1-negative tumors experienced an OR. These data indicate that tumor PD-L1 expression is a molecular marker that can enable patient selection for anti-PD-1 immunotherapy.

Example 9

Isolation of Rabbit mAbs that Detect Membranous hPD-L1 Antigen in FFPE Tissues

Rabbit Abs against human PD-L1 polypeptide were prepared by Epitomics, Inc. (Burlingame, Calif.) by immunization of rabbits using a recombinant human PD-L1 fusion protein. Antiserum titers were evaluated using standard direct ELISA with the hPD-L1 antigen and cell ELISA using transfected cells overexpressing hPD-L1. These Abs were also screened for their ability to bind to PD-L1 by IHC assay of FFPE tissue sections. The rabbit with the highest Ab titer was selected for splenectomy. Lymphocytes isolated from the spleen were fused to myeloma cells in 40×96-well plates, and screened by ELISA against the immunizing PD-L1 antigen and by cell ELISA against cells overexpressing hPD-L1. Positive clones were expanded into 24-well plates, and confirmatory screens were conducted by direct ELISA and cell ELISA. The supernatants (sups) of clones that were specific to the screening antigen were re-screened by IHC.

A set of mouse anti-hPD-L1 mAbs were also produced by immunization of mice using a protocol similar to that described above for the rabbit mAbs.

Out of a total of 185 multiclones from both rabbit and mouse immunizations screened, only ten rabbit multiclone Abs specifically detected the membranous form of hPD-L1. None of the purified mouse subclones were found to specifically detect cell surface hPD-L1. Sixty subclones from the top five rabbit multiclones (designated Nos. 13, 20, 28, 29 and 49, each comprising 12 subclones) were screened initially by IHC on FFPE low density tissue microarrays (TMAs), followed by confirmation and specificity verification in narrowed 25 subclones. Rabbit IgG was used as a negative isotype control, and mAb 5H1 (Dong et al., 2002) was used as the positive control. Specificity was further verified by antigen preabsorption assay. Through two rounds of IHC, the following 15 purified subclones were selected as the most promising Abs in terms of specificity and intensity of staining: 13-1, 13-3, 13-7, 13-8; 20-5, 20-7, 20-12, 20-6; 28-1, 28-8, 28-12; 49-5, 49-7, 49-9; and 29-8 Immunoreactivity data on these selected Abs are summarized in Table 4.

Additional assays were performed to further characterize the purified Ab clones, including determining binding affinity and cross-competition among the Abs (to identify overlapping versus different epitope regions) by surface plasmon resonance. All the Abs exhibited high binding affinity ($K_D < 10^{-9}$ M). These 15 purified clones were also re-screened by IHC on FFPE low density TMA or regular sections against various cell and tissue types known to be positive or negative for cell surface expression of PD-L1. Rabbit IgG was used as the isotype control, and mAb 5H1 was used as the positive control. At high concentration (10 µg/ml), clones 28-x and 49-x displayed low to moderate levels of background staining in tissues, while clones 13-x exhibited no background staining, which suggests that the 13-x clones have a wider dynamic range. The 20-x clones displayed various degree of background staining which was primarily cytoplasmic and diffuse. The clone with most robust detection specifically of membranous PD-L1, rabbit clone 28-8 ($K_D=100$ p M, as determined by SPR), was selected as the lead Ab for subsequent IHC assays. MAbs 28-1, 28-12, 20-12 and 29-8 had $K_D$ values of 130 pM, 94 pM, 160 pM and 1200 pM, respectively. The sequences of the $V_H$ and $V_K$ regions of mAb 28-8 are set forth in SEQ ID NOs. 35 and 36, respectively. The 28-8 Ab was shown to recognize a different epitope from mouse mAb 5H1, based on SPR analysis. Clones 28-1, 28-12, 29-8 and 20-12 were the next best Abs in terms of robust detection of membranous PD-L1 in FFPE tissues. Although mAb 13-1 had the best specificity in terms of detection of membranous PD-L1, the maximal detection level was lower than that of the other lead Abs. Western blotting was also performed with plus/minus antigen competition to verify the specificity of the top selected Abs for PD-L1.

TABLE 4

Immunoreactivity of Rabbit Anti-hPD-L1 mAbs

| | Specific Staining | | Non-Specific staining |
|---|---|---|---|
| Antibody Name | Pos. vs Neg. Staining on PD-L1 Cells* | Intensity Range on Tissues[†] (Very High, High, Medium, Low) | Background Staining on Tissues (High, Medium, Low) |
| 13-1 | Pos | Low to Very High | None |
| 13-3 | Pos | Low to High | None |
| 13-7 | Pos | Low to High | None |

TABLE 4-continued

Immunoreactivity of Rabbit Anti-hPD-L1 mAbs

|  | Specific Staining | | Non-Specific staining |
| --- | --- | --- | --- |
| Antibody Name | Pos. vs Neg. Staining on PD-L1 Cells* | Intensity Range on Tissues† (Very High, High, Medium, Low) | Background Staining on Tissues (High, Medium, Low) |
| 13-8 | Pos | Low to High | None |
| 20-5 | Pos | Low to Very High | High |
| 20-6 | Pos | Low to High | Medium |
| 20-7 | Pos | Low to High | Medium |
| 20-12 | Pos | Low to High | Medium |
| 28-1 | Pos | Low to Very High | None |
| 28-8 | Pos | Medium to Very High | None |
| 28-10 | Pos | Medium to Very High | Low |
| 28-12 | Pos | Low to Very High | None |
| 49-5 | Pos | Low to High | None |
| 49-7 | Pos | Low to High | Low |
| 49-9 | Pos | Low to High | None |
| 5H1 | Pos | High to Very High | None |
| Rb IgG | Neg | Neg | None |

*PD-L1 stably transfected CHO cells vs. CHO-S control;
†PD-L1 positive tissues included placenta and one non-small cell lung cancer; Detection up to "very high" expression suggests better sensitivity at detecting membranous PD-L1.

Figure 9:
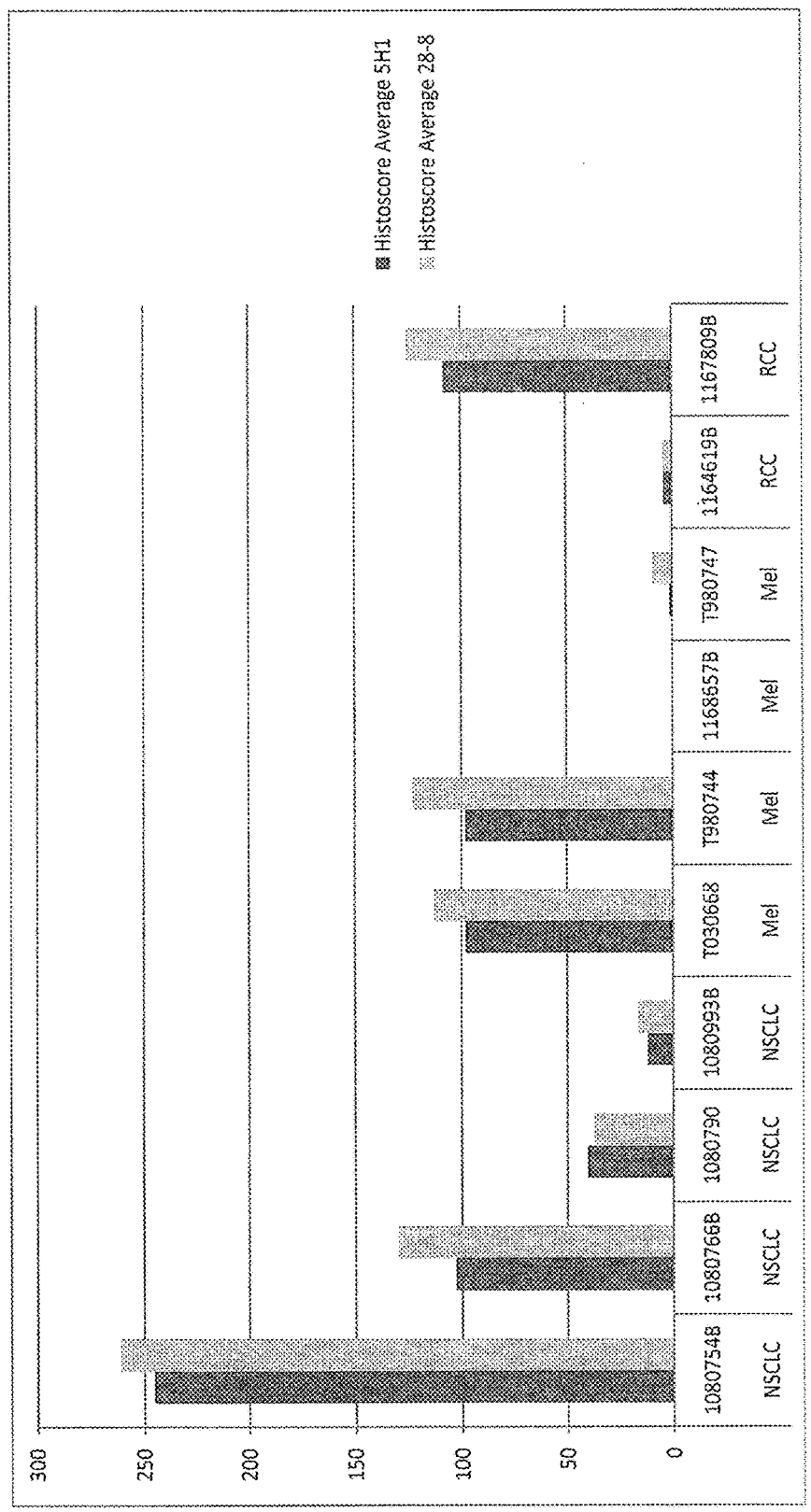
FIG. 9. Graphical comparison of the binding of mAbs 28-8 and 5H1 to PD-L1 antigen in tumor tissues by histoscore analysis. The rabbit mAb 28-8 showed higher histoscores in 7 out of 10 samples tested.
Figure 10A:
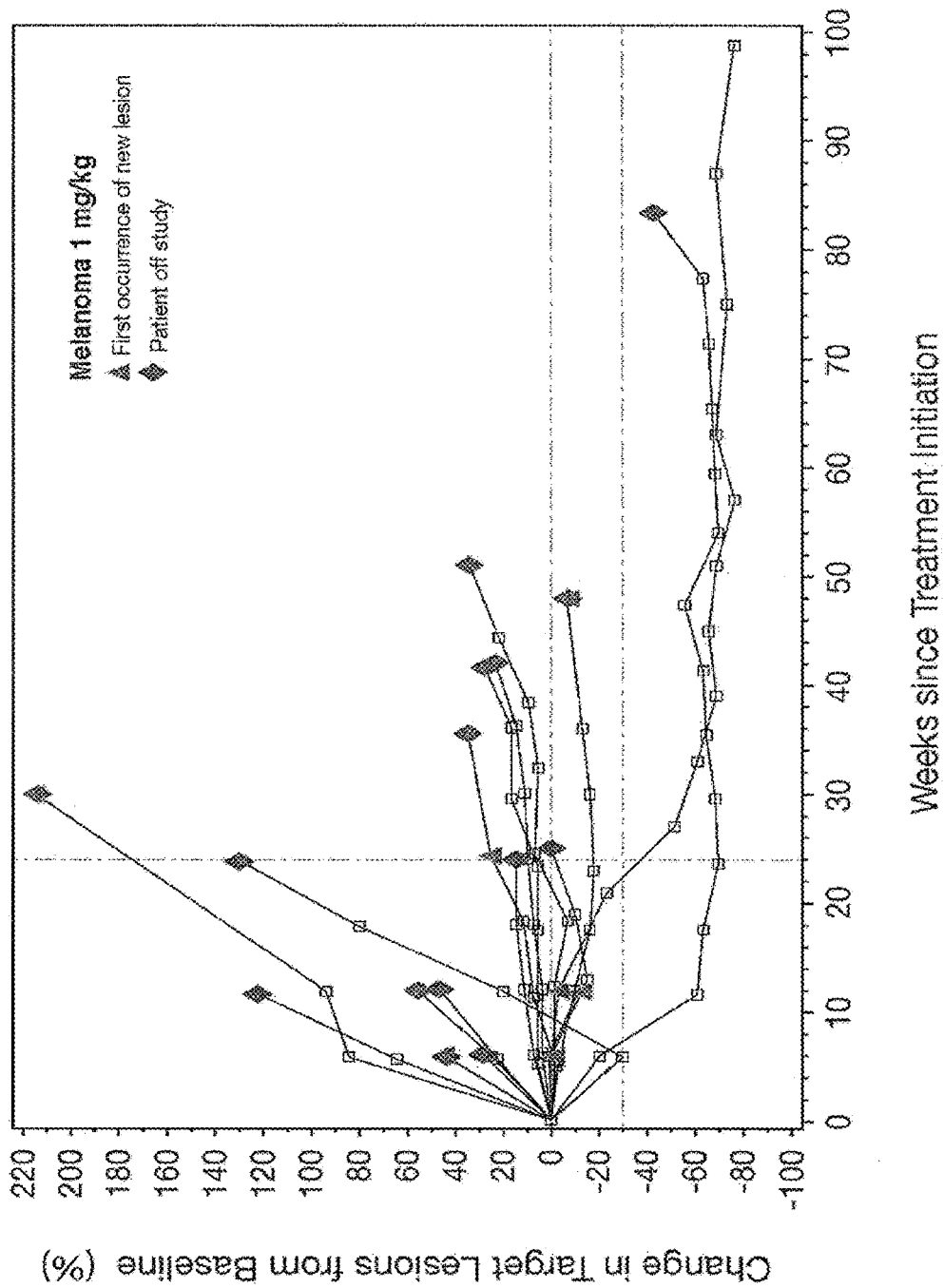
FIGS. 10A-10D. Spider plot showing activity of anti-PD-L1 mAb in patients with treatment-refractory MEL and NSCLC. Representative plots demonstrate the time course of target lesion tumor burden over time in patients with MEL treated with BMS-936559 at doses of 1 (A), 3 (B), 10 mg/kg (C) and in patients with NSCLC treated at 10 mg/kg (D). In the majority of patients who achieved ORs, responses were durable and were evident by the end of cycle 2 (3 months) of treatment, irrespective of dose or tumor type. Tumor regressions followed conventional as well as "immune-related" patterns of response.
Figure 10B:
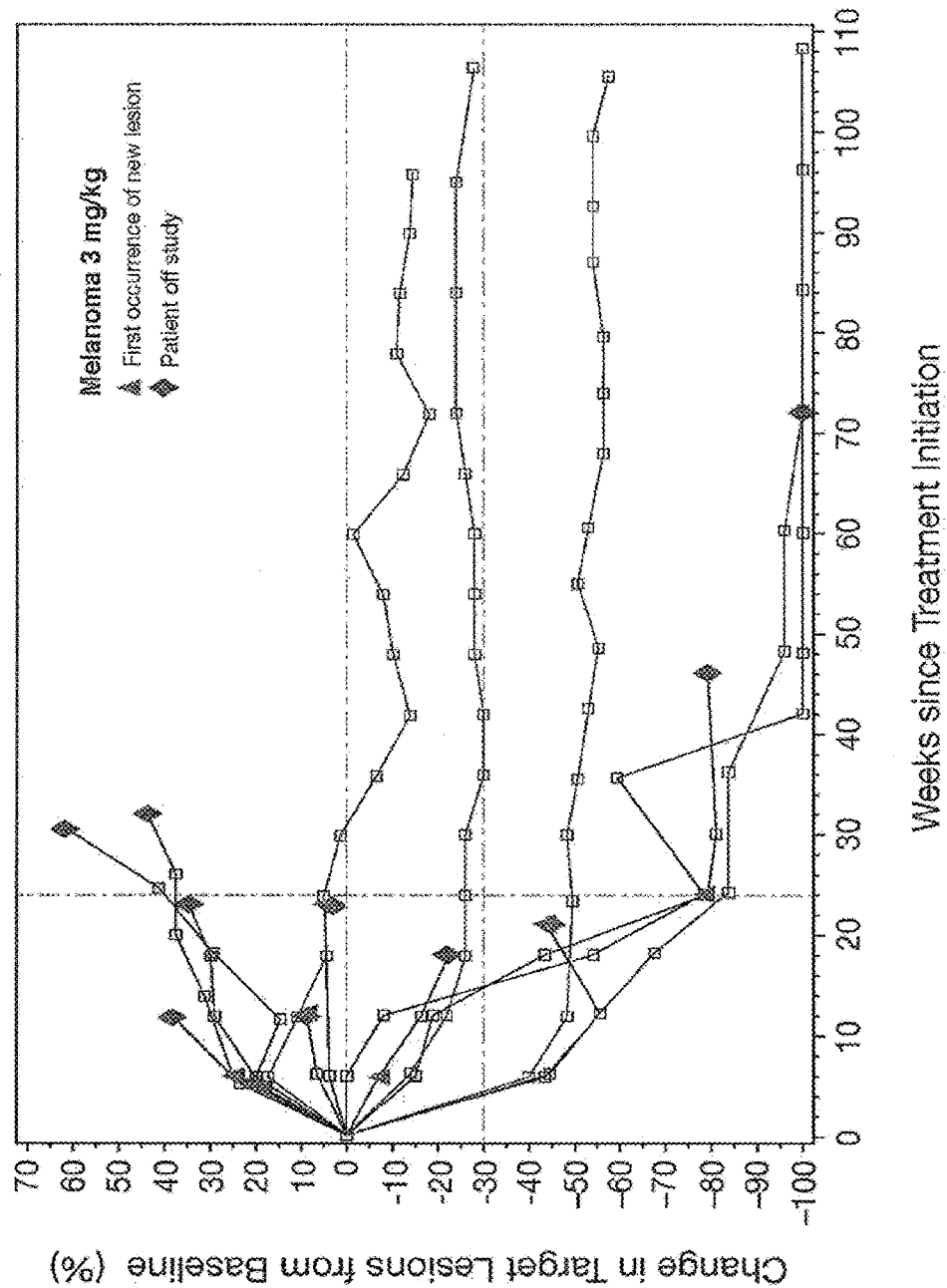
Figure 10C:
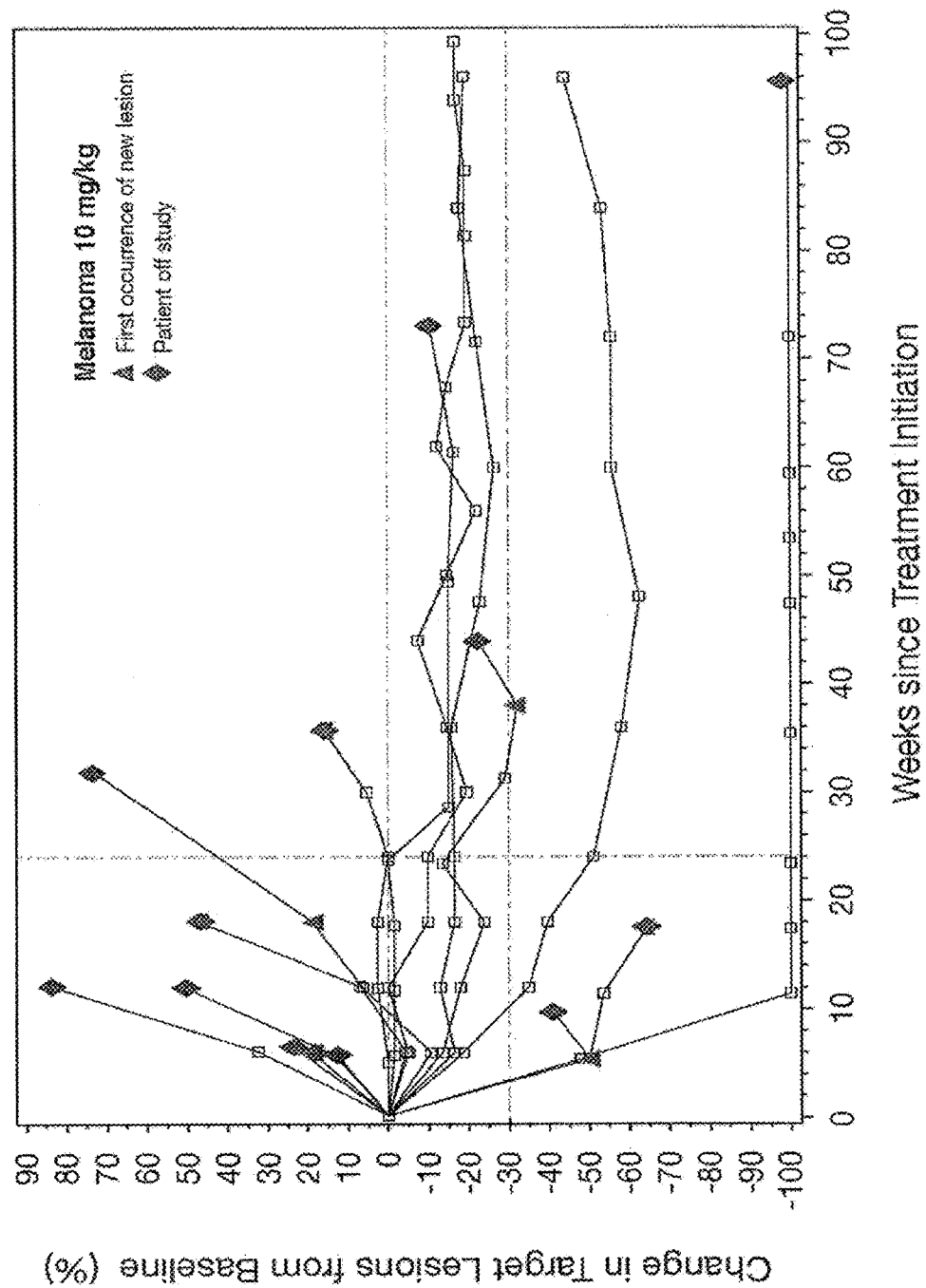
Figure 10D:
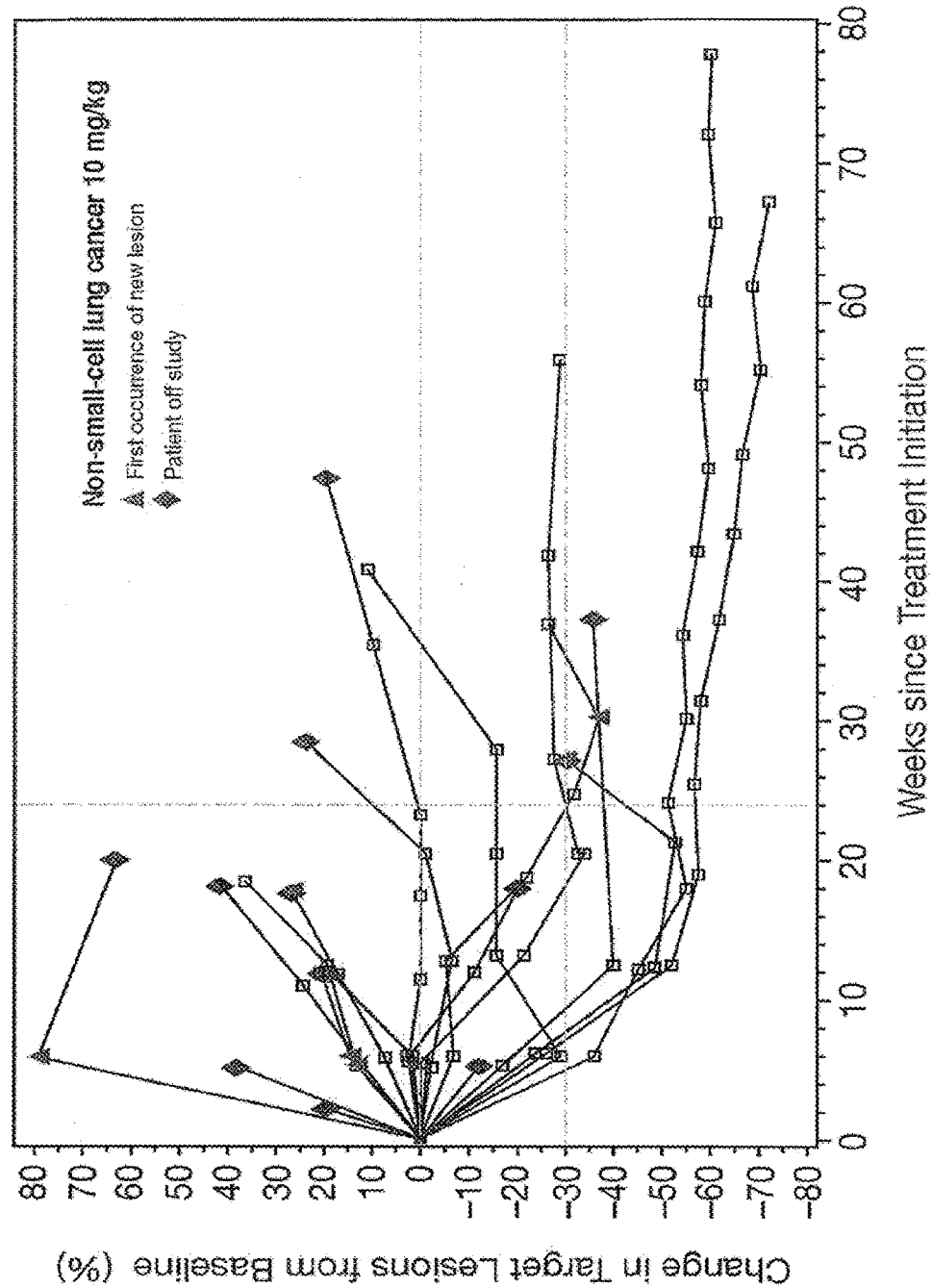
Figure 11:
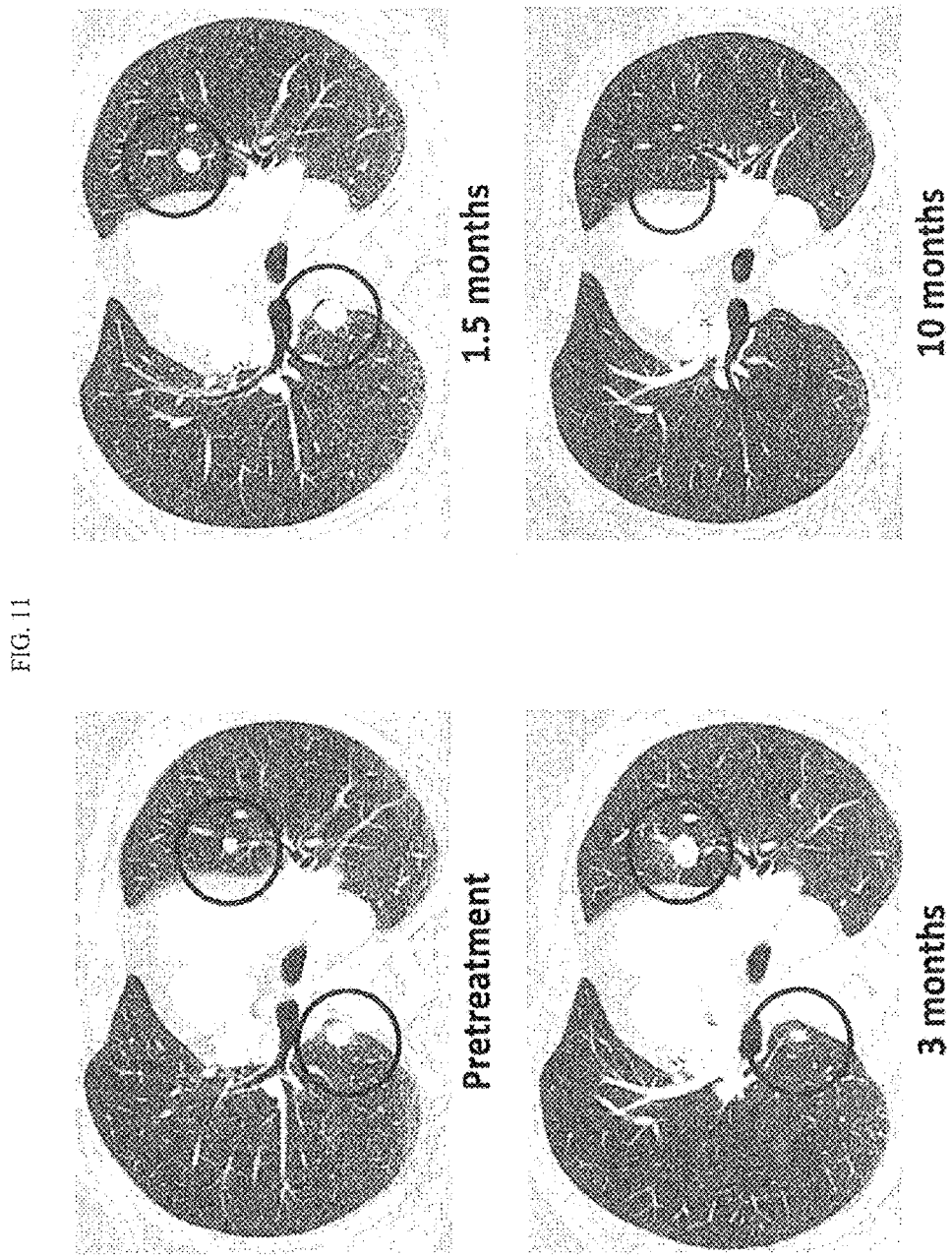
FIG. 11. Complete response in a patient with melanoma treated with BMS-936559 at 3 mg/kg. Circles indicate an initial increase in the size of pulmonary nodules at 6 weeks and 3 months followed by complete regression at 10 months ("immune-related" pattern of response).
Figure 12:
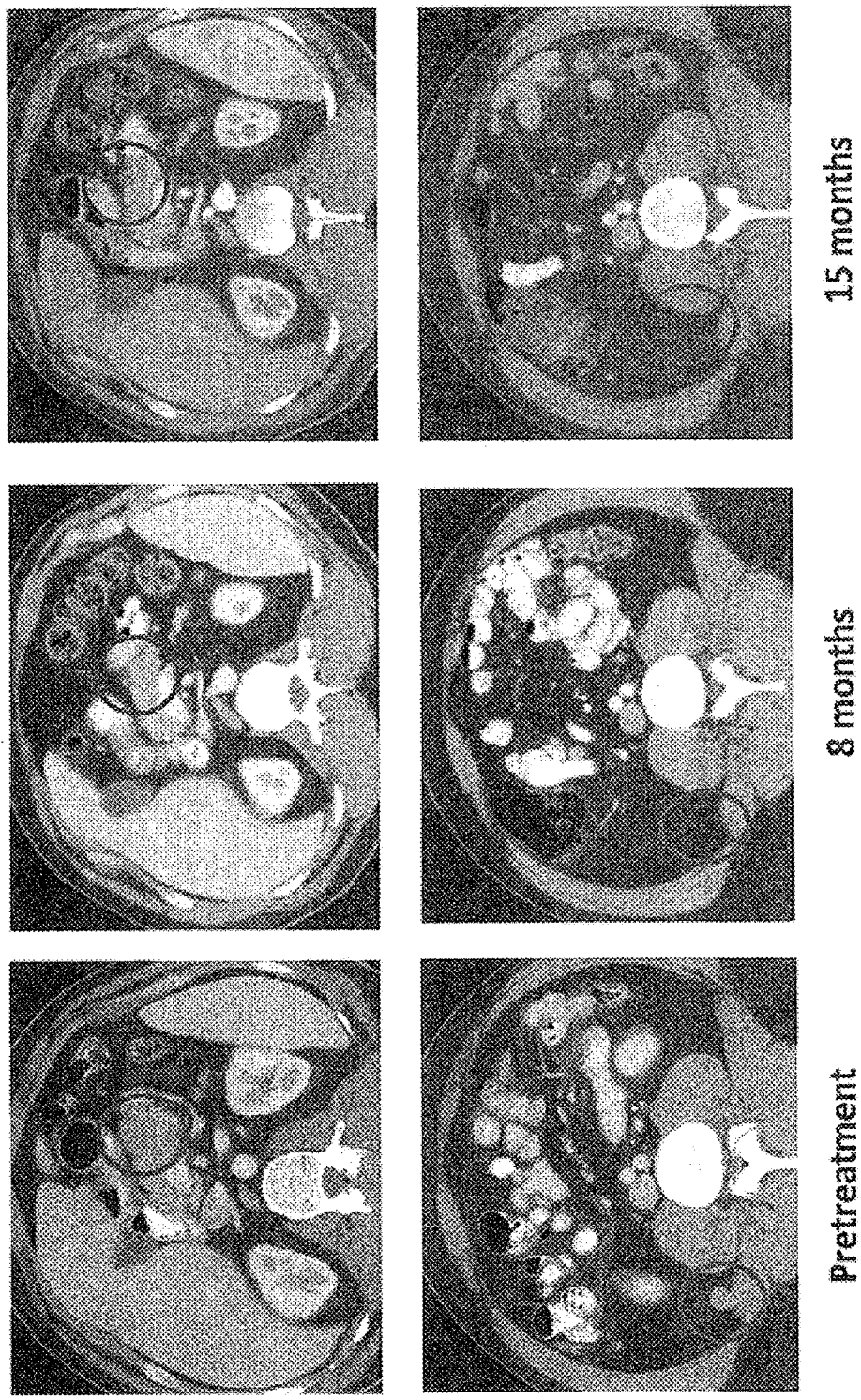
FIG. 12. Complete response in a patient with melanoma treated with BMS-936559 at 1 mg/kg. This patient developed an isolated brain metastasis 3 months after initiation of treatment that was successfully treated with stereotactic radiosurgery. A partial response in abdominal disease (circled) was noted at 8 months, with no evidence of disease at 15 months.
Figure 13:
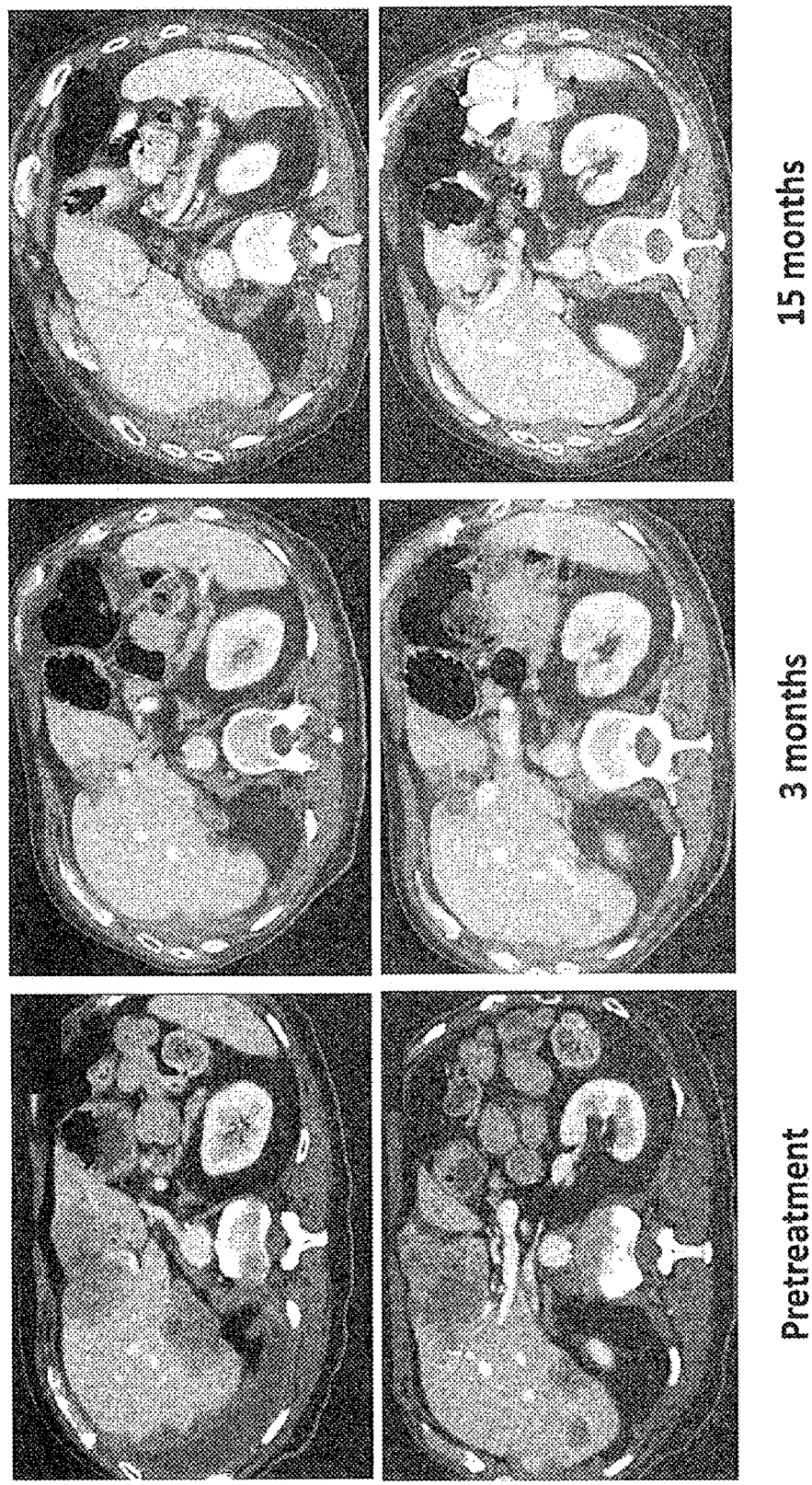
FIG. 13. Partial response in a patient with NSCLC (nonsquamous histology) treated with BMS-936559 at 10 mg/kg. Note the response in disease in right lung pleura and liver.

The binding of mAbs 5H1 and 28-8 to membranous PD-L1 in FFPE test tissue samples comprising tumor cells and tumor-infiltrating inflammatory cells from different types of tumors was compared. Membranous PD-L1 expression was evaluated using the histoscore method performed by 2 independent pathologists. Four NSCLC, 2 MEL, and 2 RCC tumors were stained with 28-8 at 2 mg/ml and 5H1 at 5 mg/ml. The data are tabulated in Table 5, and shown graphically in FIG. 9. The rabbit mAb 28-8 showed better detection (higher histoscores) for 7 out of 10 samples using 2.5-fold less Ab, and in only one sample was the histoscore for 5H1 slightly higher than for mAb 28-8.

TABLE 5

Comparison of mAbs 28-8 and 5H1 by histoscore analysis

| Tissue | Sample I.D. | Histoscore Average (5H1) | Histoscore Average (28-8) |
| --- | --- | --- | --- |
| NSCLC | 1080754B | 245 | 261 |
| NSCLC | 1080766B | 103 | 130 |
| NSCLC | 1080790 | 40 | 37 |
| NSCLC | 1080993B | 12 | 16 |
| Mel | T030668 | 98 | 113 |
| Mel | T980744 | 98 | 123 |
| Mel | 1168657B | 0 | 0 |
| Mel | T980747 | 1 | 9 |
| RCC | 1164619B | 4 | 4 |
| RCC | 1167809B | 108 | 125 |

Taube et al., 2012 demonstrated by flow cytometry on cultured cells that mAb 5H1 bound to the cell surface, and the specificity of binding to PD-L1 was confirmed using a PD-L1 fusion protein to competitively block binding of the 5H1 mAb to tissue sections. These authors also compared 5H1 with a rabbit polyclonal anti-hPD-L1 Ab, 4059, previously described by Gadiot et al., 2011, and found that whereas 5H1 showed a cell surface staining pattern on FFPE samples, Ab 4059 demonstrated diffuse cytoplasmic staining. Further, when 5H1 was compared to Ab 4059 by western blot analysis, Ab 4059 bound to multiple proteins in lysates of melanoma cells in addition to a 50 kDa protein corresponding to the expected mass of glycosylated PD-L1, in contrast to 5H1 which specifically detected the 50 kDa band of glycosylated PD-L1 (Taube et al., 2012).

In the present study, an automated IHC assay (see Example 10) was used to evaluate the binding of several commercially available anti-PD-L1 Abs and 5H1 (Dong et al., 2002) to FFPE tissue samples containing various cells expressing PD-L1. The results, summarized in Table 6, show that none of the commercially available Abs tested specifically recognized membranous PD-L1 expression in human tissues known to express PD-L1, or to clearly distinguish CHO cells expressing PD-L1 versus the untransfected parent CHO cells that did not express PD-L1. The inability of the polyclonal Ab (pAb) 4059 to bind specifically recognized membranous PD-L1 is consistent with the findings of Taube et al., 2012. The binding of 28-8 was similar to that of 5H1 in this assay, though histoscore analysis suggests that 28-8 performs better than 5H1.

TABLE 6

Binding of mAbs to FFPE Samples Containing PD-L1-expressing cells

| Source | Antibody Types | Clone No. (mAb)/ Catalog No. (pAb) | Pos. vs. Neg. Staining on PD-L1 Cells* | Human Positive Tissues† |
| --- | --- | --- | --- | --- |
| MBL | mAb | 27A2 | Failed | Failed |
| BioLegend | mAb | 29E.2A3 | Failed | Failed |
| eBiosciences | mAb | M1H1 | No Staining | No staining |
| Collaborator | mAb | 5H1 | Passed | Passed |
| ProSci | pAb | 4059 | Failed | Failed |
| LifeSpan BioSciences | pAb | LS-B480/0604 | Failed | Failed |

*PD-L1 stably transfected CHO cells vs. parent CHO-S negative control;
†PD-L1 positive tissues included tonsil and/or thymus;
mAb, mouse mAb; pAb, rabbit polyclonal Ab.

Example 10

Development of Automated IHC Protocol for Assessing PD-L1 Expression

An automated IHC protocol was developed to assay PD-L1 expression in FFPE specimens. Tissue sections (4 μm) were mounted on slides, deparaffinized in an autostainer (Leica) by soaking twice for 5 min in xylene, and re-hydrated through soaking twice for 2 min each time in 100% EtOH, twice in 95% (v/v) EtOH, once in 70% (v/v) EtOH, and once in de-ionized water (dH$_2$O). Antigen retrieval was performed using a decloaking chamber (Biocare Medical Decloaking Chamber Plus) and Dako pH 6 buffer, heated to 110° C. (P1) for 10 min, then moved to the next step (P2 FAN ON at 98° C.; FAN OFF at 90° C.). The slides were cooled at room temperature (RT) for 15 min and rinsed with water for about 1 min.

Reagents were set up on an autostainer (BIOGENEX® i6000), using a pap pen to define the tissue area. The IHC assay, run using the autostainer in research mode, comprised the following steps: neutralizing endogenous peroxidase using the Peroxidase Block (Leica) for 10 min, followed by rinsing 3 times with IHC wash buffer (Dako); applying Protein Block (Leica) to the slides, and incubating for 10 min at RT, followed by washing 3 times with wash buffer; applying the primary Ab to the slides (2 μg/ml) and incubating for 1 h at RT, followed by washing 6 times with wash buffer; adding Post Primary Block (NovoLink Kit) to the slides and incubating for 30 min, followed by washing 6 times with wash buffer; adding NovoLink Polymer (NovoLink Kit) to the slides and incubating for 30 min, followed by washing 6 times with wash buffer; adding the DAB chromogen substrates (NovoLink Kit) and developing for 3 min, followed by rinsing 5 times with dH$_2$O at RT; counterstaining with hematoxylin (NovoLink Kit) for 1 min at RT, followed by washing 3 times with dH$_2$O for 5 times at RT. The primary Ab was selected from the rabbit anti-PD-L1 Abs shown in Table 4; mAb 28-8 was the preferred Ab. As a negative control, rabbit IgG (Dako) was used. The tissue sections were dehydrated using a Leica autostainer by washing once for 2 min in 70% EtOH, twice for 2 min in 95% EtOH, and three times for 2 min in 70% EtOH, then cleared by washing three times for 5 min in xylene. The sections were permanently mounted with permount to the slide, covered with a coverslip, and transferred to a chemical hood to dry.

Example 11

Design of Phase I Clinical Study on Anti-PD-L1 Antibody

Study Design

A Phase I study was conducted to assess the safety and tolerability of BMS-936559 (also referred to herein and in U.S. Pat. No. 7,943,743 as 12A4) in patients with selected advanced solid tumors. Secondary objectives included initial assessment of the antitumor activity of BMS-936559 and pharmacokinetic evaluation. Pharmacodynamic measures were included under exploratory objectives. Patients were treated in 6-week cycles of BMS-936559 administered as a 60-minute intravenous infusion every 2 weeks on days 1, 15, and 29 of each cycle. Patients continued treatment for up to 16 cycles unless they experienced unacceptable toxicity, disease progression, or withdrew consent. In some patients who were clinically stable, treatment beyond initial disease progression was permitted until further progression was confirmed.

Dose Escalation

Patients with advanced NSCLC, MEL, CRC, RCC, ovarian (OV), gastric (GC), breast (BC), and pancreatic (PC) carcinoma were eligible to enroll. Using an accelerated titration design, safety was assessed at doses of 0.3, 1, 3, and 10 mg/kg. One patient was enrolled in each successive cohort until there was a ≥grade 2 drug-related AE during cycle 1. Two additional patients were then enrolled at that dose level and the study was transitioned to a standard 3+3 design. Intra-patient dose escalation or de-escalation was not permitted. The maximum tolerated dose (MTD) was defined as the highest dose where less than one-third of patients had a dose-limiting toxicity.

Cohort Expansion

Initially, 5 expansion cohorts (n=16/cohort) were enrolled at 10 mg/kg for patients with NSCLC, MEL, RCC, OV, and CRC. Based on initial signals of activity, additional expansion cohorts (up to n=16/cohort) were enrolled for MEL (at 1.0 and 3.0 mg/kg), NSCLC (squamous or nonsquamous histology cohorts randomized to 1, 3, or 10 mg/kg), and at 10 mg/kg for PC, BC, and GC.

Patients

Patients were required to have documented advanced NSCLC, MEL, RCC, OV, CRC, PC, GC, or BC, and have failed at least one prior tumor-appropriate therapy for advanced/metastatic disease (except for PC or GC patients who could be treatment-naive). Other inclusion criteria included age ≥18 years, life expectancy ≥12 weeks, Eastern Cooperative Oncology Group performance status of ≤2, measurable disease as defined by RECIST v1.0, and adequate hematologic, hepatic, and renal function. Patients with treated brain metastases were allowed, if stable for at least 8 weeks. Major exclusion criteria included a history of autoimmune disease or other diseases requiring systemic steroids or immunosuppressive medication, prior therapy with T cell-modulating Abs (including anti-PD-1, anti-PD-L1 and anti-CTLA-4), history of HIV, or active hepatitis B or C.

In this ongoing study, 207 patients with NSCLC (n=75), MEL (n=55), CRC (n=18), RCC (n=17), OV (n=17), PC (n=14), GC (n=7), or BC (n=4) were treated with BMS-936559 during a 34-month period and are included in the safety data. Efficacy was characterized in 160 response-evaluable patients. The baseline demographic characteristics of the total and response-evaluable patient populations were very similar (Brahmer et al., 2012). Among treated patients, 86% had received prior chemotherapy and 28% immunologic or biological therapy. Prior therapies by tumor type included immunotherapy (56%) and B-RAF inhibitor (9%) in patients with MEL; platinum-based chemotherapy (95%) and tyrosine kinase inhibitors (TKI; 41%) in patients with NSCLC; and nephrectomy (94%), anti-angiogenic therapy (82%), and immunotherapy (41%) in patients with RCC (see Brahmer et al., 2012) for more details on patient pretreatments).

Statistical Analysis

All 207 patients commencing treatment as of the date of analysis were used for summaries of baseline characteristics and AEs. The efficacy population consisted of 160 response-evaluable patients who initiated treatment at least 7 months before the date of analysis. AEs were coded using MedDRA v14.1. Individual best overall responses were derived from radiographic scan measurements according to modified RECIST v1.0. ORs were confirmed by at least one sequential tumor assessment. Additional details regarding statistical methods are provided in Brahmer et al., 2012.

Example 12

Safety Evaluations on Patients Treated with Anti-PD-L1 Antibody

Safety evaluations (clinical examination and laboratory assessments) were conducted on all treated patients at baseline and regular intervals (weekly during cycle 1 and biweekly thereafter). AE severity was graded based on the NCI CTCAE, v3.0. Disease assessment via computed tomography (CT) scans or magnetic resonance imaging was performed at baseline and prior to each treatment cycle.

A MTD was not reached up to the highest tested dose of 10 mg/kg of BMS-936559. The median duration of therapy was 12 weeks (range 2.0-111.1 weeks). A relative dose intensity of ≥90% was achieved in 86% of patients. Twelve of 207 patients (6%) discontinued treatment due to a BMS-936559-related AE (see Brahmer et al., 2012, for details).

AEs regardless of causality (any grade) were reported in 188 of 207 patients. Investigator-assessed BMS-936559-related AEs were noted in 126 of 207 (61%) patients. The most common drug-related AEs were fatigue, infusion reactions, diarrhea, arthralgia, rash, nausea, pruritus, and headache. Most events were low grade with BMS-936559-related grade 3-4 events noted in 19 of 207 (9%) patients (Brahmer et al., 2012). The spectrum, frequency, and severity of BMS-936559-related AEs were similar across the dose levels, with the exception of infusion reactions. Drug-related AEOSIs, with potential immune-related etiologies, were observed in 81 of 207 (39%) of the patients and included rash, hypothyroidism, hepatitis, and single cases each of sarcoidosis, endophthalmitis, diabetes mellitus, and myasthenia gravis (Brahmer et al., 2012). These AEs were predominantly grade 1-2 and generally reversible with treatment interruption or discontinuation. Notably, 9 patients were treated with corticosteroids for the management of AEs. AEs improved or resolved in all patients. Furthermore, 4 of these 9 patients maintained disease control despite treatment with corticosteroids. Endocrine AEs were managed with replacement therapy and patients reinitiated treatment with BMS-936559 at the discretion of the treating physician. Infusion reactions were observed in 21 of 207 (10%) patients, predominantly at 10 mg/kg. They were grade 1-2 with the exception of one grade 3 event at 10 mg/kg. Infusion reactions were generally rapidly reversible with antihistamines and antipyretics and, in some cases, corticosteroids. A prophylactic regimen with antihistamines and antipyretics was implemented during the study. Patients with grade 1-2 infusion reactions were able to continue treatment with BMS-936559 with prophylactic antihistamines and antipyretics and at a reduced infusion rate. BMS-936559-related serious AEs occurred in 11 of 207 (5%) patients. As of the data analysis date, 45 patients (22%) had died (Brahmer et al., 2012); no drug-related deaths were observed.

Example 13

Pharmacokinetics/Pharmacodynamics Analyses on Anti-PD-L1 Antibody

For PK analyses, serial blood samples were collected and serum concentrations of BMS-936559 were quantified by ELISA. Peripheral blood mononuclear cells were isolated from patients at baseline and following one treatment cycle to assay PD-L1 RO by BMS-936559 on circulating CD3-positive T-cells via flow cytometry (Brahmer et al., 2010).

Serum concentrations of BMS-936559 increased in a dose-dependent manner from 1-10 mg/kg (n=131). Geometric mean area under the curve (0-14 days) for the 1, 3, and 10 mg/kg dose levels were 2210, 7750, and 36620 μg/mL·hr (coefficient of variation [CV] 34-59%), respectively; geometric mean peak concentrations at these dose levels were 27, 83, and 272 μg/mL (CV 30-34%), respectively, after the first dose. The half-life of BMS-936559 was estimated from population pharmacokinetic data as approximately 15 days. PD-L1 RO on CD3-positive peripheral blood lymphocytes was assessed in 29 MEL patients at the end of 1 cycle of treatment, at BMS-936559 doses from 1-10 mg/kg. Median RO exceeded 65% for all groups (Brahmer et al., 2012).

Example 14

Antitumor Efficacy Exhibited by Anti-PD-L1 Antibody

One-hundred and sixty patients out of the 207 treated were evaluable for response and included those with NSCLC, MEL, CRC, RCC, OV, and PC, but not patients with GC or BC. Clinical activity was observed at all doses ≥1 mg/kg (Brahmer et al., 2012). ORs (confirmed complete [CR] or partial [PR] responses) were observed in patients with MEL, NSCLC, RCC, and OV (Table 7), as illustrated by representative spider plots and CT scans (FIGS. 10-13), and many ORs were also durable (Table 8). Four additional patients had a persistent reduction in target lesions in the presence of new lesions, consistent with an "immune-related" pattern of response; however, for the purpose of calculating response rates, they were not categorized as responders. Antitumor responses and/or prolonged stable disease (SD) were observed in patients with a variety of prior therapies received. ORs were observed even in patients with an extensive burden of metastatic disease.

In patients with MEL, there were 9 ORs across the 1, 3, and 10 mg/kg dose levels, with response rates of 6%, 29%, and 19%, respectively. Three MEL patients achieved a CR. All 9 MEL patients who experienced an OR started treatment ≥1 year prior to data analysis; of these 5 had a response duration ≥1 year. Additionally 14 MEL patients (27%) had SD lasting ≥24 weeks. In patients with NSCLC, there were 5 ORs amongst the 3 and 10 mg/kg dose levels, with response rates of 8% and 16%, respectively. There were ORs in patients with non-squamous (n=4) or squamous histology (n=1). All 5 NSCLC responders started treatment ≥24 weeks prior to data analysis; of these, 3 had responses lasting ≥24 weeks. Six additional NSCLC patients had SD lasting ≥24 weeks. There was 1 PR out of 17 patients with OV (6% response rate) and 3 patients (18%) with SD lasting ≥24 weeks, all at the 10 mg/kg dose. In patients with RCC, there were ORs in 2 of 17 (12%) patients treated at 10 mg/kg with responses lasting 4 and 18 months, respectively. Seven additional RCC patients had SD lasting ≥24 weeks.

TABLE 7

Clinical Activity of BMS-936559 in 160 Patients, Response Evaluable*

| Tumor Type | Dose (mg/kg) | n | ORR§ No. of patients (%) [95% CI] | SD ≥ 24 wk No. of patients (%) [95% CI] | PFSR** at 24 wk (%) [95% CI] |
|---|---|---|---|---|---|
| MEL | 0.3 | 1 | 0 [0-98] | 0 [0-98] | N/A |
|  | 1 | 18 | 1 (6) [0.1-27] | 6 (33) [13-59] | 39 [16-61] |
|  | 3 | 17 | 5 (29)† [10-56] | 3 (18) [4-43] | 47 [21-72] |
|  | 10 | 16 | 3 (19)†† [4-46] | 5 (31) [11-59] | 44 [19-68] |
| ALL MEL |  | 52 | 9 (17) (8-30) | 14 (27) [16-41] | 42 [28-56] |
| NSCLC§ | 1 | 11 | 0 [0-29] | 0 [0-29] | N/A |
| Squamous | 1 | 1 | 0 [0-98] | 0 [0-98] | N/A |
| Non-Squamous | 1 | 10 | 0 [0-31] | 0 [0-31] | N/A |
| Squamous | 3 | 13 | 1 (8) [0.2-36] | 1 (8) [0.2-36] | 34 [7-60] |
| Squamous | 3 | 4 | 0 [0-60] | 1 (25) [0.6-81] | 50 [1-99] |
| Non-Squamous | 3 | 9 | 1 (11) [0.3-48] | 0 [0-34] | 25 [0-55] |
| Squamous | 10 | 25 | 4 (16) [5-36] | 5 (20) [7-41] | 46 [25-67] |
| Squamous | 10 | 8 | 1 (13) [0.3-53] | 2 (25) [3-65] | 47 [10-83] |
| Non-Squamous | 10 | 17 | 3 (18) [4-43] | 3 (18) [4-43] | 46 [20-72] |
| ALL NCSLC |  | 49 | 5 (10) [3-22] | 6 (12) [5-25] | 31 [17-45] |
| ALL Squamous |  | 13 | 1 (8) [0.2-36] | 3 (23.1) [5-54] | 43 [15-71] |
| ALL Non-Squamous |  | 36 | 4 (11) [3-26] | 3 (8) [2-23] | 26 [10-42] |
| OV | 3 | 1 | 0 [0-98] | 0 [0-98] | N/A |
|  | 10 | 16 | 1 (6) [0.2-30] | 3 (19) [4-46] | 25 [4-46] |
| ALL OV |  | 17 | 1 (6) [0.1-29] | 3 (18) [4-43] | 22 [2-43] |
| RCC | 10 | 17 | 2 (12) [2-36] | 7 (41) [18-67] | 53 [29-77] |

CI denotes Confidence intervals, MEL melanoma, RCC renal cell carcinoma, NSCLC non-small cell lung cancer, OV ovarian cancer, RCC renal cell carcinoma, N/A not applicable, ORR objective response rate (complete response + partial response), SD stable disease, and PFSR progression-free survival rate.
*Efficacy population consists of response-evaluable patients who initiated treatment at least 7 months prior to the date of analysis and had measurable disease at a baseline tumor assessment and at least one of the following: an on-study tumor assessment, clinical progression, or death.
†Includes two CRs.
††Includes one CR.
§Objective response rates ([CR + PR] ÷ n} × 100) are based on confirmed responses only, with confidence intervals calculated using the Clopper-Pearson method.
** Progression-free survival rate was the proportion of patients who did not progress, and were alive at 24 weeks, calculated by the Kaplan-Meier methodology, with confidence intervals using the Greenwood method
Individual patient responses were adjudicated per RECIST v1.0 with modification (see study protocol in Brahmer et al. (2012) N. Engl. J. Med. (submitted) for additional information).

TABLE 8

Duration of Objective Responses to BMS-936559*

| Tumor Type | Dose (mg/kg) | No. of Patients with OR | Duration of Response (months)† |
|---|---|---|---|
| MEL | 1 | 1 | 6.9 |
|  | 3 | 5 | 23.5+, 22.9+, 16.2+, 4.1+, 3.5 |
|  | 10 | 4 | 24.6+, 23.9+, 18.0+, 17.0 |
| NSCLC | 1 | 0 | 9.2+ |
|  | 3 | 1 | 2.3+ |
|  | 10 | 4 | 16.6+, 12.6+, 9.8, 3.5 |
| RCC | 10 | 2 | 17, 4 |
| OV | 10 | 1 | 1.3+ |

*MEL denotes melanoma, NSCLC non-small cell lung cancer, RCC renal cell cancer, OV ovarian cancer.
†Time from first response to time of documented progression, death, or for censored data Denoted by +), time to last tumor assessment.

Sequence Listing Summary

| SEQ ID NO: | Description |
|---|---|
| 1 | $V_H$ amino acid sequence of 17D8 |
| 2 | $V_H$ amino acid sequence of 2D3 |
| 3 | $V_H$ amino acid sequence of 4H1 |
| 4 | $V_H$ amino acid sequence of 5C4 |
| 5 | $V_H$ amino acid sequence of 4A11 |
| 6 | $V_H$ amino acid sequence of 7D3 |
| 7 | $V_H$ amino acid sequence of 5F4 |
| 8 | $V_L$ amino acid sequence of 17D8 |
| 9 | $V_L$ amino acid sequence of 2D3 |
| 10 | $V_L$ amino acid sequence of 4H1 |
| 11 | $V_L$ amino acid sequence of 5C4 |
| 12 | $V_L$ amino acid sequence of 4A11 |
| 13 | $V_L$ amino acid sequence of 7D3 |
| 14 | $V_L$ amino acid sequence of 5F4 |
| 15 | $V_H$ amino acid sequence of 3G10 |
| 16 | $V_H$ amino acid sequence of 12A4 |
| 17 | $V_H$ amino acid sequence of 10A5 |
| 18 | $V_H$ amino acid sequence of 5F8 |
| 19 | $V_H$ amino acid sequence of 10H10 |
| 20 | $V_H$ amino acid sequence of 1B12 |
| 21 | $V_H$ amino acid sequence of 7H1 |
| 22 | $V_H$ amino acid sequence of 11E6 |
| 23 | $V_H$ amino acid sequence of 12B7 |
| 24 | $V_H$ amino acid sequence of 13G4 |
| 25 | $V_L$ amino acid sequence of 3G10 |
| 26 | $V_L$ amino acid sequence of 12A4 |
| 27 | $V_L$ amino acid sequence of 10A5 |
| 28 | $V_L$ amino acid sequence of 5F8 |
| 29 | $V_L$ amino acid sequence of 10H10 |
| 30 | $V_L$ amino acid sequence of 1B12 |
| 31 | $V_L$ amino acid sequence of 7H1 |
| 32 | $V_L$ amino acid sequence of 11E6 |
| 33 | $V_L$ amino acid sequence of 12B7 |
| 34 | $V_L$ amino acid sequence of 13G4 |
| 35 | $V_H$ amino acid sequence of 28-8 |
| 36 | $V_L$ amino acid sequence of 28-8 |

REFERENCES

Baitsch et al. (2012) *PloS One* 7(2):e30852.
Barbas et al. (1994) *J Am Chem Soc* 116:2161-62.
Barbas et al. (1995) *Proc Natl Acad Sci USA* 92:2529-33.
Beck et al. (2006) *J Clin Oncol* 24:2283-89.
Beiboer et al. (2000) *J Mol Biol* 296:833-49.
Berezov et al. (2001) *BIAjournal* 8:Scientific Review 8.
Blank et al. (2005) *Cancer Immunol Immunother* 54:307-14.
Bordeaux et al. (2010) *BioTechniques* 48:197-209.
Bourgeois et al. (1998) *J Virol* 72:807-10.
Brahmer et al. (2010) *J Clin Oncol* 28:3167-75.
Brahmer et al. (2012) *N Engl J Med* 366:2455-65.
Butte et al. (2007) *Immunity* 27:111-22.
Butte et al. (2008) *Mol Immunol* 45:3567-72.
Cheang et al. (2006) *J Clin Oncol* 24:5637-44.
Condeelis et al. (2010) *Cold Spring Harb Perspect Biol* 2010; 2:a003848.
Clinical Trials Website, http://www.clinicaltrials.gov, last accessed Mar. 14, 2013.
McDermott et al. (2013), submitted.
Ditzel et al. (1996) *J Immunol* 157:739-49.
Dong et al. (2002) *Nat Med* 8:793-800.
Dong et al. (2003) *J Mol Med* 81:281-87.
Dong et al. (2004) *Immunity* 20:327-36.
Epitomics (2013) http://www.epitomics.com/services/7point.php#, last accessed Mar. 14, 2013.
Fife et al. (2009) *Nat Immunol* 10:1185-92.
Fischer et al. (2008) *PloS One* 3(12):e4069.
Flaherty et al. (2010) *N Engl J Med* 363:809-19.
Flies et al. (2011) *Yale J Biol Med* 84:409-21.
Gadiot et al. (2011) *Cancer* 117:2192-201.
Garbe et al. (2012) *Eur J Cancer* 48:2375-90.
Gridelli et al. (2008) *J Thorac Oncol* 3:430-40.
Freeman et al. (2000) *J Exp Med* 192:1027-34.
Gajewski et al. (2010) *Cancer J* 16:399-403.
Hamanishi et al. (2007) *Proc Natl Acad Sci USA* 104:3360-65.
Hanna et al. (2004) *J Clin Oncol* 22:1589-97.
He et al. (2004) *J Immunol* 173:4919-28.
Hino et al. (2010) *Cancer* 116:1757-66.
Hodi et al. (2010) *N Engl J Med* 363:711-23.
Hollinger et al. (2005) *Nature Biotech* 23(9):1126-36.
Holt et al. (2011) *Therapy* 8:43-54.
Hutson et al. (2012) *Ann Oncol* 23 (Suppl. 9): ixe14, Abstr LBA22 PR.
Igarashi et al. (1995) *J Biochem* (Tokyo) 117:452-7.
Iwai et al. (2002) *Proc Natl Acad Sci USA* 99:12293-97.
Kim et al. (2010) *Curr Opin Immunol* 22:223-30.
Klimka et al. (2000) *Br J Cancer* 83(2):252-60.
Konishi et al. (2004) *Clin. Cancer Res.* 10:5094-100.
Latchman et al. (2001) *Nat Immunol* 2:261-8.
Lebbe et al. (2012) *Ann Oncol* 23 (Suppl 9):ix363, Abstr 116PD.
Levi et al. (1993) *Proc Natl Acad Sci USA* 90:4374-78.
Lipson et al. (2013) *Clin Cancer Res* 19:462-68.
McCabe et al. (2010) *Cancer Biother Radiopharm* 25(3): 253-61.
McDermott et al. (2006) *Semin Oncol* 33:583-87.
Mellman et al. (2011) *Nature* 480:480-489.
Miller (2006) *Semin Oncol* 33:S25-S31.
Motzer et al. (2008) *Lancet* 372:449-56.
Motzer et al. (2010) *Cancer* 116:4256-65.
Mulders (2009) *BJU Int* 104:1585-89.
NCCN GUIDELINES® (2013) http://www.nccn.org/professionals/physician_gls/f_guidelines.asp#site, last accessed Mar. 14, 2013.
Nishimura et al. (1999) *Immunity* 11:141-51.
Olafsen et al. (2010) *Semin Nucl Med* 40(3):167-81.
Pardoll (2012) *Nat Rev Cancer* 12:252-64.
Park et al. (2010) *Blood* 116:1291-98.
Paterson et al. (2011) *J Immunol* 187:1097-105.
Phan et al. (2003) *Proc Natl Acad Sci USA* 100:8372-77.
Polymenis et al. (1994) *J Immunol* 152:5218-29.
Rader et al. (1998) *Proc Natl Acad Sci USA* 95:8910-15.
Ribas et al. (2005) *J Clin Oncol* 23:8968-77.
Robert et al. (2011) *N Engl J Med* 364:2517-26.
Rossi et al. (2005) *Am J Clin Pathol* 124:295-302.
Scagliotti et al. (2011) *J Thorac Oncol* 6:64-70.
Sharma et al. (2011) *Nat Rev Cancer* 11:805-12.

Shepherd et al. (2000) *J Clin Oncol* 18:2095-103.
Shepherd et al. (2005) *N Engl J Med* 353:123-32.
Sjoblom et al. (2006) *Science* 314:268-74.
Sosman et al. (2012) *N Engl J Med* 366:707-14.
Sompuram et al. (2006) *Am J Clin Pathol* 125:82-90.
Taube et al. (2012) *Sci Transl Med* 4:127ra37.
Thompson et al. (2006) *Cancer Res* 66:3381-85.
Tivol et al. (1995) *Immunity* 3:541-47.
Topalian et al. (2011) *J Clin Oncol* 29:4828-36.
Topalian et al. (2012a) *Curr Opin Immunol* 24:1-6.
Topalian et al. (2012b)*N Engl J Med* 366:2443-54.
Topalian et al. (2012c) *Curr Opin Immunol* 24:207-12.
U.S. Pat. No. 7,488,802, issued Feb. 10, 2009 to Collins et al.
U.S. Pat. No. 7,635,757, issued Dec. 22, 2009 to Freeman et al.
U.S. Pat. No. 7,943,743, issued May 17, 2011 to Korman et al.
U.S. Pat. No. 8,008,449, issued Aug. 30, 2011 to Korman et al.
U.S. Pat. No. 8,168,757, issued May 1, 2012 to Finnefrock et al.
U.S. Pat. No. 8,217,149, issued Jul. 10, 2012 to Irving et al.
U.S. Publication No. 2009/0317368, published Dec. 24, 2009 by Chen et al.
Weber et al. (2013), submitted to *N Engl J Med*.
Wolchok et al. (2009) *Clin Cancer Res* 15:7412-20.
Wolchok et al. (2013), submitted to *N Engl J Med*.
Xu and Davis (2000) *Immunity* 13: 37-45.
Yang et al. (2011) *J Immunol* 187:1113-19.
Zou et al. (2008) *Nat Rev Immunol* 8:467-77.

What is claimed is:

1. A method of treating a tumor in a human subject in need thereof, comprising administering to the subject a therapeutically effective amount of an anti-PD-L1 antibody; wherein the anti-PD-L1 antibody is administered intravenously over 60 minutes infusion; wherein the tumor is derived from a cancer of the urethra; and wherein the tumor is refractory to a platinum based chemotherapy.

2. The method of claim 1, wherein the tumor is advanced.

3. The method of claim 1, wherein the tumor is locally advanced.

4. The method of claim 1, wherein the tumor is metastatic.

5. The method of claim 1, wherein the therapeutically effective amount of the anti-PD-L1 antibody is administered once every 3 weeks.

6. The method of claim 1, wherein the anti-PD-L1 antibody is formulated in a pharmaceutical composition.

7. The method of claim 6, wherein the pharmaceutical composition further comprises a pharmaceutically acceptable salt, an anti-oxidant, an aqueous carrier, a non-aqueous carrier, or any combination thereof.

8. The method of claim 7, wherein the salt comprises a sodium salt.

9. The method of claim 7, wherein the salt comprises sodium chloride.

10. The method of claim 1, wherein at least 1% of tumor cells exhibit membrane PD-L1 expression.

11. The method of claim 1, wherein at least 5% of tumor cells exhibit membrane PD-L1 expression.

12. The method of claim 1, further comprising administering an anti-cancer agent.

13. The method of claim 2, further comprising administering an anti-cancer agent.

14. The method of claim 3, further comprising administering an anti-cancer agent.

15. The method of claim 4, further comprising administering an anti-cancer agent.

16. The method of claim 10, further comprising administering an anti-cancer agent.

17. The method of claim 12, wherein the anti-cancer agent is a chemotherapy.

18. The method of claim 12, wherein the anti-cancer agent is a radiotherapy.

19. The method of claim 13, wherein the anti-cancer agent is a chemotherapy.

20. The method of claim 13, wherein the anti-cancer agent is a radiotherapy.

21. The method of claim 14, wherein the anti-cancer agent is a chemotherapy.

22. The method of claim 14, wherein the anti-cancer agent is a radiotherapy.

23. The method of claim 1, wherein the platinum-based chemotherapy comprises cisplatin, carboplatin, or both.

24. The method of claim 1, wherein the subject is further administered a corticosteroid.

25. A method of treating a tumor in a human subject in need thereof, comprising administering to the subject a therapeutically effective amount of an anti-PD-L1 antibody once every 3 weeks;
wherein the anti-PD-L1 antibody is administered intravenously over 60 minutes infusion;
wherein the tumor is derived from a cancer of the urethra;
wherein the tumor is advanced or metastatic; and
wherein the tumor is refractory to a platinum based chemotherapy.

26. The method of claim 1, wherein the subject is administered an antihistamine prior to the anti-PD-L1 antibody.

27. The method of claim 25, wherein the subject is administered an antihistamine prior to the anti-PD-L1 antibody.

28. A method of treating a tumor in a human subject in need thereof, comprising administering to the subject about 10 mg/kg of an anti-PD-L1 antibody once every 2 weeks, wherein the anti-PD-L1 antibody is administered intravenously over 60 minutes infusion; wherein the tumor is derived from a cancer of the urethra; and wherein the tumor is refractory to a platinum based chemotherapy.

29. The method of claim 28, wherein the tumor is locally advanced or metastatic.

30. The method of claim 28, wherein at least 1% of tumor cells exhibit membrane PD-L1 expression.

* * * * *

SEQUENCE LISTING

<160> NUMBER OF SEQ ID NOS: 36

<210> SEQ ID NO 1
<211> LENGTH: 113
<212> TYPE: PRT
<213> ORGANISM: Homo sapiens

<400> SEQUENCE: 1

Gln Val Gln Leu Val Glu Ser Gly Gly Asp Val Val Gln Pro Gly Gly
1               5                   10                  15

Ser Leu Arg Leu Ser Cys Ala Ala Ser Gly Val Ala Phe Ser Asn Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Met Leu Tyr
65                  70                  75                  80

Leu Gln Met Asn Ser Leu Arg Ala Glu Asp Thr Ala Met Tyr Tyr Cys
                85                  90                  95

Ala Arg Asn Asp Asp Tyr Trp Gly Gln Gly Thr Leu Val Thr Val Ser
            100                 105                 110

Ser

<210> SEQ ID NO 2
<211> LENGTH: 113
<212> TYPE: PRT
<213> ORGANISM: Homo sapiens

<400> SEQUENCE: 2

Gln Val Gln Leu Val Glu Ser Gly Gly Asp Val Val Gln Pro Gly Arg
1               5                   10                  15

Ser Leu Arg Leu Ser Cys Ala Ala Ser Gly Leu Thr Phe Thr Asn Tyr
            20                  25                  30

Gly Phe His Trp Val Arg Gln Ala Pro Gly Lys Gly Leu Glu Trp Val
        35                  40                  45

Ala Val Ile Trp Tyr Asp Gly Ser Lys Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Asn Leu Arg Ala Glu Asp Thr Ala Val Tyr Tyr Cys
                85                  90                  95

-continued

```
Ala Thr Gly Asp Asp Tyr Trp Gly Gln Gly Thr Leu Val Thr Val Ser
            100                 105                 110
Ser

<210> SEQ ID NO 3
<211> LENGTH: 113
<212> TYPE: PRT
<213> ORGANISM: Homo sapiens

<400> SEQUENCE: 3

Gln Val Tyr Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Leu Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Thr Ser Leu Arg Val Glu Asp Thr Ala Val Tyr Tyr Cys
                85                  90                  95

Ala Ser Asn Val Asp His Trp Gly Gln Gly Thr Leu Val Thr Val Ser
            100                 105                 110
Ser

<210> SEQ ID NO 4
<211> LENGTH: 113
<212> TYPE: PRT
<213> ORGANISM: Homo sapiens

<400> SEQUENCE: 4

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110
Ser

<210> SEQ ID NO 5
<211> LENGTH: 121
<212> TYPE: PRT
<213> ORGANISM: Homo sapiens

<400> SEQUENCE: 5

Gln Leu Gln Leu Gln Glu Ser Gly Pro Gly Leu Val Lys Pro Ser Glu
1               5                   10                  15
```

```
Thr Leu Ser Leu Thr Cys Thr Val Ser Gly Gly Ser Leu Ser Arg Ser
            20                  25                  30

Ser Phe Phe Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Val Arg Asp Tyr Asp Ile Leu Thr Gly Asp Glu Asp Tyr Trp Gly
            100                 105                 110

Gln Gly Thr Leu Val Thr Val Ser Ser
            115                 120
```

<210> SEQ ID NO 6
<211> LENGTH: 113
<212> TYPE: PRT
<213> ORGANISM: Homo sapiens

<400> SEQUENCE: 6

```
Gln Val Gln Leu Val Glu Ser Gly Gly Gly Val Val Gln Pro Gly Arg
1               5                   10                  15

Ser Leu Arg Leu Ser Cys Thr Thr Ser Gly Ile Thr Phe Ser Ser Tyr
            20                  25                  30

Gly Phe His Trp Val Arg Gln Ala Pro Gly Lys Gly Leu Glu Trp Val
        35                  40                  45

Ala Val Ile Trp Tyr Asp Gly Ser Lys Lys Tyr Tyr Ala Asp Ser Val
    50                  55                  60

Lys Gly Arg Phe Thr Leu Ser Arg Asp Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Thr Gly Asp Asp Tyr Trp Gly Gln Gly Thr Leu Val Thr Val Ser
            100                 105                 110

Ser
```

<210> SEQ ID NO 7
<211> LENGTH: 121
<212> TYPE: PRT
<213> ORGANISM: Homo sapiens

<400> SEQUENCE: 7

```
Gln Leu Gln Leu Gln Glu Ser Gly Pro Gly Leu Val Lys Pro Ser Glu
1               5                   10                  15

Thr Leu Ser Leu Thr Cys Ser Val Ser Gly Gly Ser Leu Ser Arg Ser
            20                  25                  30

Ser Tyr Phe Trp Gly Trp Ile Arg Gln Pro Pro Gly Lys Gly Leu Glu
        35                  40                  45

Trp Ile Ala Ser Ile Phe Tyr Ser Gly Glu Thr Tyr Phe Asn Pro Ser
    50                  55                  60

Leu Lys Ser Arg Val Thr Ile Ser Val Asp Thr Ser Arg Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Tyr Asp Ile Leu Thr Gly Asp Glu Asp Tyr Trp Gly
```

```
                100                 105                 110
Gln Gly Thr Leu Val Thr Val Ser Ser
        115                 120

<210> SEQ ID NO 8
<211> LENGTH: 107
<212> TYPE: PRT
<213> ORGANISM: Homo sapiens

<400> SEQUENCE: 8

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Ile Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 9
<211> LENGTH: 107
<212> TYPE: PRT
<213> ORGANISM: Homo sapiens

<400> SEQUENCE: 9

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Thr Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 10
<211> LENGTH: 107
<212> TYPE: PRT
<213> ORGANISM: Homo sapiens

<400> SEQUENCE: 10

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45
```

```
Tyr Asp Ala Ser Asn Arg Ala Thr Gly Ile Pro Ala Arg Phe Ser Gly
            50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Ser Asn Trp Pro Arg
                 85                  90                  95

Thr Phe Gly Gln Gly Thr Lys Val Glu Ile Lys
            100                 105

<210> SEQ ID NO 11
<211> LENGTH: 107
<212> TYPE: PRT
<213> ORGANISM: Homo sapiens

<400> SEQUENCE: 11

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Ser Asn Trp Pro Arg
                 85                  90                  95

Thr Phe Gly Gln Gly Thr Lys Val Glu Ile Lys
            100                 105

<210> SEQ ID NO 12
<211> LENGTH: 107
<212> TYPE: PRT
<213> ORGANISM: Homo sapiens

<400> SEQUENCE: 12

Asp Ile Gln Met Thr Gln Ser Pro Ser Ser Leu Ser Ala Ser Val Gly
  1               5                  10                  15

Asp Arg Val Ser Ile Thr Cys Arg Ala Ser Gln Gly Ile Ser Ser Trp
                 20                  25                  30

Leu Ala Trp Tyr Gln Gln Lys Pro Glu Lys Ala Pro Lys Ser Leu Ile
             35                  40                  45

Tyr Ala Ala Ser Asn Leu Arg Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Ser Tyr Pro Arg
                 85                  90                  95

Thr Phe Gly Gln Gly Thr Lys Val Glu Ile Lys
            100                 105

<210> SEQ ID NO 13
<211> LENGTH: 107
<212> TYPE: PRT
<213> ORGANISM: Homo sapiens

<400> SEQUENCE: 13
```

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105
```

<210> SEQ ID NO 14
<211> LENGTH: 107
<212> TYPE: PRT
<213> ORGANISM: Homo sapiens

<400> SEQUENCE: 14

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Tyr Pro Arg
                85                  90                  95

Thr Phe Gly Gln Gly Thr Lys Val Glu Ile Lys
            100                 105
```

<210> SEQ ID NO 15
<211> LENGTH: 117
<212> TYPE: PRT
<213> ORGANISM: Homo sapiens

<400> SEQUENCE: 15

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Gly Phe Ser Trp Val Arg Gln Ala Pro Gly Gln Gly Leu Glu Trp Met
            35                  40                  45

Gly Trp Ile Thr Ala Tyr Asn Gly Asn Thr Asn Tyr Ala Gln Lys Leu
    50                  55                  60

Gln Gly Arg Val Thr Met Thr Thr Asp Thr Ser Thr Ser Thr Val Tyr
65                  70                  75                  80

Met Glu Leu Arg Ser Leu Arg Ser Asp Thr Ala Val Tyr Tyr Cys
                85                  90                  95

Ala Arg Asp Tyr Phe Tyr Gly Met Asp Val Trp Gly Gln Gly Thr Thr
            100                 105                 110
```

```
Val Thr Val Ser Ser
        115
```

```
<210> SEQ ID NO 16
<211> LENGTH: 123
<212> TYPE: PRT
<213> ORGANISM: Homo sapiens

<400> SEQUENCE: 16

Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Thr Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Lys Ala His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Lys Phe His Phe Val Ser Gly Ser Pro Phe Gly Met Asp Val
            100                 105                 110

Trp Gly Gln Gly Thr Thr Val Thr Val Ser Ser
        115                 120
```

```
<210> SEQ ID NO 17
<211> LENGTH: 118
<212> TYPE: PRT
<213> ORGANISM: Homo sapiens

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Val His Trp Val Arg Gln Ala Pro Gly Gln Arg Leu Glu Trp Met
        35                  40                  45

Gly Trp Leu His Ala Asp Thr Gly Ile Thr Lys Phe Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Arg Ile Gln Leu Trp Phe Asp Tyr Trp Gly Gln Gly Thr
            100                 105                 110

Leu Val Thr Val Ser Ser
        115
```

```
<210> SEQ ID NO 18
<211> LENGTH: 120
<212> TYPE: PRT
<213> ORGANISM: Homo sapiens

<400> SEQUENCE: 18

Gln Val Gln Leu Val Gln Ser Gly Ala Glu Val Lys Lys Pro Gly Ser
1               5                   10                  15

Ser Val Lys Val Ser Cys Lys Val Ser Gly Gly Ile Phe Ser Thr Tyr
```

```
                    20                  25                  30
Ala Ile Asn Trp Val Arg Gln Ala Pro Gly Gln Gly Leu Glu Trp Met
                35                  40                  45

Gly Gly Ile Ile Pro Ile Phe Gly Thr Ala Asn His Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gln Gly Ile Ala Ala Leu Phe Asp Tyr Trp Gly Gln
                100                 105                 110

Gly Thr Leu Val Thr Val Ser Ser
                115                 120
```

<210> SEQ ID NO 19
<211> LENGTH: 113
<212> TYPE: PRT
<213> ORGANISM: Homo sapiens

<400> SEQUENCE: 19

```
Glu Val Gln Leu Val Glu Ser Gly Gly Gly Leu Val Gln Pro Gly Arg
1               5                   10                  15

Ser Leu Arg Leu Ser Cys Ala Val Ser Gly Phe Thr Phe Asp Asp Tyr
                20                  25                  30

Val Val His Trp Val Arg Gln Ala Pro Gly Lys Gly Leu Glu Trp Val
                35                  40                  45

Ser Gly Ile Ser Gly Asn Ser Gly Asn Ile Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Val Pro Phe Asp Tyr Trp Gly Gln Gly Thr Leu Val Thr Val Ser
                100                 105                 110

Ser
```

<210> SEQ ID NO 20
<211> LENGTH: 123
<212> TYPE: PRT
<213> ORGANISM: Homo sapiens

<400> SEQUENCE: 20

```
Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Ser Tyr
                20                  25                  30

Ala Ile Ser Trp Val Arg Gln Ala Pro Gly Gln Gly Leu Glu Trp Met
                35                  40                  45

Gly Gly Ile Ile Pro Ile Phe Gly Arg Ala His Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Lys Phe His Phe Val Ser Gly Ser Pro Phe Gly Met Asp Val
                100                 105                 110
```

```
Trp Gly Gln Gly Thr Thr Val Thr Val Ser Ser
        115                 120
```

<210> SEQ ID NO 21
<211> LENGTH: 123
<212> TYPE: PRT
<213> ORGANISM: Homo sapiens

<400> SEQUENCE: 21

```
Gln Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Lys Ala His Tyr Ala Gln Lys Phe
    50                  55                  60

Gln Gly Arg Val Thr Ile Thr Ala Asp Glu Ser Thr Thr Thr Ala Tyr
65                  70                  75                  80

Met Glu Leu Ser Ser Leu Arg Ser Glu Asp Thr Ala Val Tyr Tyr Cys
                85                  90                  95

Ala Arg Lys Tyr Asp Tyr Val Ser Gly Ser Pro Phe Gly Met Asp Val
            100                 105                 110

Trp Gly Gln Gly Thr Thr Val Thr Val Ser Ser
        115                 120
```

<210> SEQ ID NO 22
<211> LENGTH: 121
<212> TYPE: PRT
<213> ORGANISM: Homo sapiens

<400> SEQUENCE: 22

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Asn Trp Val Arg Gln Ala Pro Gly Gln Gly Leu Glu Trp Met
        35                  40                  45

Gly Gly Ile Ile Pro Ile Phe Gly Ser Ala Asn Tyr Ala Gln Lys Phe
    50                  55                  60

Gln Asp Arg Val Thr Ile Thr Ala Asp Glu Ser Thr Ser Ala Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Ser Gly Trp Ser Arg Tyr Tyr Met Asp Val Trp Gly
            100                 105                 110

Gln Gly Thr Thr Val Thr Val Ser Ser
        115                 120
```

<210> SEQ ID NO 23
<211> LENGTH: 123
<212> TYPE: PRT
<213> ORGANISM: Homo sapiens

<400> SEQUENCE: 23

```
Gln Val Gln Leu Val Gln Ser Gly Ala Glu Val Lys Glu Pro Gly Ser
1               5                   10                  15
```

Ser Val Lys Val Ser Cys Lys Ala Ser Gly Thr Phe Asn Ser Tyr
            20                  25                  30

Ala Ile Ser Trp Val Arg Gln Ala Pro Gly Gln Gly Leu Glu Trp Met
        35                  40                  45

Gly Gly Ile Ile Pro Leu Phe Gly Ile Ala His Tyr Ala Gln Lys Phe
    50                  55                  60

Gln Gly Arg Val Thr Ile Thr Ala Asp Glu Ser Thr Asn Thr Ala Tyr
65                  70                  75                  80

Met Asp Leu Ser Ser Leu Arg Ser Glu Asp Thr Ala Val Tyr Tyr Cys
                85                  90                  95

Ala Arg Lys Tyr Ser Tyr Val Ser Gly Ser Pro Phe Gly Met Asp Val
            100                 105                 110

Trp Gly Gln Gly Thr Thr Val Thr Val Ser Ser
            115                 120

<210> SEQ ID NO 24
<211> LENGTH: 121
<212> TYPE: PRT
<213> ORGANISM: Homo sapiens

<400> SEQUENCE: 24

Glu Val Gln Leu Val Glu Ser Gly Gly Gly Leu Val Gln Pro Gly Arg
1               5                   10                  15

Ser Leu Arg Leu Ser Cys Ala Ala Ser Gly Ile Thr Phe Asp Asp Tyr
            20                  25                  30

Gly Met His Trp Val Arg Gln Ala Pro Gly Lys Gly Leu Glu Trp Val
        35                  40                  45

Ser Gly Ile Ser Trp Asn Arg Gly Arg Ile Glu Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Gly Arg Phe Arg Tyr Phe Asp Trp Phe Leu Asp Tyr Trp Gly
            100                 105                 110

Gln Gly Thr Leu Val Thr Val Ser Ser
        115                 120

<210> SEQ ID NO 25
<211> LENGTH: 107
<212> TYPE: PRT
<213> ORGANISM: Homo sapiens

<400> SEQUENCE: 25

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Val Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Arg
                85                  90                  95

```
Thr Phe Gly Gln Gly Thr Lys Val Glu Ile Lys
            100                 105
```

<210> SEQ ID NO 26
<211> LENGTH: 106
<212> TYPE: PRT
<213> ORGANISM: Homo sapiens

<400> SEQUENCE: 26

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys
            100                 105
```

<210> SEQ ID NO 27
<211> LENGTH: 107
<212> TYPE: PRT
<213> ORGANISM: Homo sapiens

<400> SEQUENCE: 27

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys
            100                 105
```

<210> SEQ ID NO 28
<211> LENGTH: 108
<212> TYPE: PRT
<213> ORGANISM: Homo sapiens

<400> SEQUENCE: 28

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
```

```
                        50                  55                  60
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Trp Thr Phe Gly Gln Gly Thr Lys Val Glu Ile Lys
            100                 105
```

<210> SEQ ID NO 29
<211> LENGTH: 107
<212> TYPE: PRT
<213> ORGANISM: Homo sapiens

<400> SEQUENCE: 29

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Trp
                20                  25                  30

Leu Ala Trp Tyr Gln Gln Lys Pro Glu Lys Ala Pro Lys Ser Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Tyr
                 85                  90                  95

Thr Phe Gly Gln Gly Thr Lys Leu Glu Ile Lys
            100                 105
```

<210> SEQ ID NO 30
<211> LENGTH: 106
<212> TYPE: PRT
<213> ORGANISM: Homo sapiens

<400> SEQUENCE: 30

```
Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Thr
                 85                  90                  95

Phe Gly Gln Gly Thr Lys Val Glu Ile Lys
            100                 105
```

<210> SEQ ID NO 31
<211> LENGTH: 106
<212> TYPE: PRT
<213> ORGANISM: Homo sapiens

<400> SEQUENCE: 31

```
Glu Ile Val Leu Thr Gln Ser Pro Ala Thr Leu Ser Leu Ser Pro Gly
 1               5                  10                  15
```

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Thr
                 85                  90                  95

Phe Gly Gln Gly Thr Lys Val Glu Ile Lys
            100                 105

<210> SEQ ID NO 32
<211> LENGTH: 106
<212> TYPE: PRT
<213> ORGANISM: Homo sapiens

<400> SEQUENCE: 32

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Phe Gly Gly Gly Thr Lys Val Glu Ile Lys
            100                 105

<210> SEQ ID NO 33
<211> LENGTH: 106
<212> TYPE: PRT
<213> ORGANISM: Homo sapiens

<400> SEQUENCE: 33

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Thr
                 85                  90                  95

Phe Gly Gln Gly Thr Arg Leu Glu Ile Lys
            100                 105

<210> SEQ ID NO 34

```
<211> LENGTH: 107
<212> TYPE: PRT
<213> ORGANISM: Homo sapiens

<400> SEQUENCE: 34

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Phe
                85                  90                  95

Thr Phe Gly Pro Gly Thr Lys Val Asp Ile Lys
            100                 105

<210> SEQ ID NO 35
<211> LENGTH: 141
<212> TYPE: PRT
<213> ORGANISM: Oryctolagus cuniculus

<400> SEQUENCE: 35

Met Glu Thr Gly Leu Arg Trp Leu Leu Leu Val Ala Val Leu Lys Gly
1               5                   10                  15

Val Gln Cys Leu Ser Val Glu Glu Ser Gly Gly Arg Leu Val Thr Pro
            20                  25                  30

Gly Thr Pro Leu Thr Leu Thr Cys Thr Ala Ser Gly Phe Thr Ile Thr
        35                  40                  45

Asn Tyr His Met Phe Trp Val Arg Gln Ala Pro Gly Lys Gly Leu Glu
50                  55                  60

Trp Ile Gly Val Ile Thr Ser Ser Gly Ile Gly Ser Ser Thr Thr
65                  70                  75                  80

Tyr Tyr Ala Thr Trp Ala Lys Gly Arg Phe Thr Ile Ser Lys Thr Ser
                85                  90                  95

Thr Thr Val Asn Leu Arg Ile Thr Ser Pro Thr Thr Glu Asp Thr Ala
            100                 105                 110

Thr Tyr Phe Cys Ala Arg Asp Tyr Phe Thr Asn Thr Tyr Ala Leu
        115                 120                 125

Asp Ile Trp Gly Pro Gly Thr Leu Val Thr Val Ser Ser
130                 135                 140

<210> SEQ ID NO 36
<211> LENGTH: 116
<212> TYPE: PRT
<213> ORGANISM: Oryctolagus cuniculus

<400> SEQUENCE: 36

Met Asp Thr Arg Ala Pro Thr Gln Leu Leu Gly Leu Leu Leu Leu Trp
1               5                   10                  15

Leu Pro Gly Ala Arg Cys Ala Leu Val Met Thr Gln Thr Pro Ser Ser
            20                  25                  30

Thr Ser Thr Ala Val Gly Gly Thr Val Thr Ile Lys Cys Gln Ala Ser
        35                  40                  45
```

-continued

```
Gln Ser Ile Ser Val Tyr Leu Ala Trp Tyr Gln Gln Lys Pro Gly Gln
    50              55                  60

Pro Pro Lys Leu Leu Ile Tyr Ser Ala Ser Thr Leu Ala Ser Gly Val
65              70                  75                  80

Pro Ser Arg Phe Lys Gly Ser Arg Ser Gly Thr Glu Tyr Thr Leu Thr
                85                  90                  95

Ile Ser Gly Val Gln Arg Glu Asp Ala Ala Thr Tyr Tyr Cys Leu Gly
            100             105                 110

Ser Ala Gly Ser
        115
```